US007129264B2

(12) United States Patent
Smallheer et al.

(10) Patent No.: US 7,129,264 B2
(45) Date of Patent: Oct. 31, 2006

(54) BIARYLMETHYL INDOLINES AND INDOLES AS ANTITHROMBOEMBOLIC AGENTS

(75) Inventors: Joanne M. Smallheer, Yardley, PA (US); Mimi L. Quan, Yardley, PA (US); Shuaige Wang, West Chester, PA (US); Gregory S. Bisacchi, Ringoes, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 138 days.

(21) Appl. No.: 10/824,025

(22) Filed: Apr. 14, 2004

(65) Prior Publication Data

US 2004/0220206 A1 Nov. 4, 2004

Related U.S. Application Data

(60) Provisional application No. 60/463,452, filed on Apr. 16, 2003.

(51) Int. Cl.
*A61K 31/404* (2006.01)
*A61K 31/4045* (2006.01)
*C07D 209/18* (2006.01)
*C07D 209/14* (2006.01)
*C07D 209/10* (2006.01)

(52) U.S. Cl. ............... 514/419; 548/495; 548/505; 548/507

(58) Field of Classification Search ............... 548/469, 548/490, 419, 495, 505, 507
See application file for complete search history.

(56) References Cited

U.S. PATENT DOCUMENTS

| | | | |
|---|---|---|---|
| 5,886,191 | A | 3/1999 | Dominguez et al. |
| 6,100,238 | A | 8/2000 | Gyorkos et al. |
| 6,239,129 | B1 | 5/2001 | Lavielle et al. |
| 6,358,991 | B1 | 3/2002 | Jenkins |
| 6,376,486 | B1 | 4/2002 | Jenkins et al. |
| 6,429,205 | B1 | 8/2002 | Jacobson et al. |
| 6,534,535 | B1 | 3/2003 | Zhu et al. |
| 2003/0040533 | A1 | 2/2003 | Lesieur et al. |

FOREIGN PATENT DOCUMENTS

| | | |
|---|---|---|
| WO | WO 99/12903 | 3/1999 |
| WO | WO 99/12935 | 3/1999 |
| WO | WO 00/35886 | 6/2000 |
| WO | WO 01/12187 | 2/2001 |
| WO | WO 2001012600 A1 * | 2/2001 |
| WO | WO 01/57020 | 8/2001 |
| WO | WO 02/03986 | 1/2002 |
| WO | WO 02/03989 | 1/2002 |
| WO | WO 2004050637 | 6/2004 |
| WO | WO 2004062661 | 7/2004 |
| WO | WO 2004/080971 | 9/2004 |

OTHER PUBLICATIONS

Walsh, P.N., "Platelets and Factor XI Bypass the Contact System of Blood Coagulation", *Thromb. Haemostasis.* 82(2), pp. 234-242, 1999.

Coleman, R. Contact Activation Pathway: Inflammatory, Fibrinolytic, Anticoagulant, Antiadhesive, and Antiangiogenic Activities, *Hemostasis and thrombosis: basic principles and clinical practice*, Lippincott Williams & Wilkins, 2001, pp. 103-122.

Schmaier, A.H., "Contact Activation", *Thrombosis and Hemorrhage*, Williams & Wilkins, 1998, pp. 105-128.

Galiani, D., "Activation of Factor IX by Factor XIa", *Trends in Cardiovascular Medicine*, vol. 10, No. 5, 2000, pp. 198-204.

Bouma, B.N. et al., "Thrombin-Activatable Fibrinolysis Inhibitor (TAFI, Plasma Procarboxypeptidase B, Procarboxypeptidase R, Procarboxypeptidase U)", *Thrombosis. Research*, 2001, 101, pp. 329-354.

Gailani, D., "Gene Targeting in Hemostasis. Factor XI", *Frontiers in Bioscience*, 2001, 6, pp. d201-d207.

Gailani, D., et al., "A murine model of factor XI deficiency", *Blood Coagulation and Fibrinolysis*, 1997, vol. 8, pp. 134-144.

Minnema, M.C., et al., "Activation of Clotting Factors XI and IX in Patients with Acute Myocardial Infarction", *Arterioscler. Thromb. Vasc. Biol.*, 2000, 20, pp. 2489-2493.

(Continued)

*Primary Examiner*—Kamal A. Saeed
*Assistant Examiner*—Joseph R. Kosack
(74) *Attorney, Agent, or Firm*—Jing G. Sun

(57) ABSTRACT

The present invention provides compounds of Formula (I):

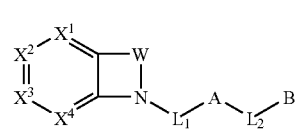

(I)

or a stereoisomer or pharmaceutically acceptable salt or hydrate form thereof, wherein the variables A, B, $L_1$, $L_2$, $X^1$, $X^2$, $X^3$, $X^4$ and W are as defined herein. The compounds of Formula (I) are useful as selective inhibitors of serine protease enzymes of the coagulation cascade and/or contact activation system; for example thrombin, factor Xa, factor XIa, factor IXa, factor VIIa and/or plasma kallikrein. In particular, it relates to compounds that are selective factor XIa inhibitors. This invention also relates to pharmaceutical compositions comprising these compounds and methods of treating thromboembolic and/or inflammatory disorders using the same.

30 Claims, No Drawings

OTHER PUBLICATIONS

Murakami, T., et al., "Evaluation of Factor XIa-$\alpha_1$-Antitrypsin in Plasma, a Contact Phase-Activated Coaguation Factor-Inhibitor Complex, in Patients With Coronary Artery Disease", *Arterioscler. Thromb. Vasc. Biol.*, 1995, 15, pp. 1107-1113.

Meijers, J.C.M., et al., "High Levels of Coagulation Factor XI as a Risk Factor for Venous Thrombosis", *N. Engl. J. Med.,* 2000, vol. 342, No. 10, pp. 696-701.

Yee et al., "A Novel Series of Selective Leukotriene Antagonists: Exploration and Optimization of the Acidic Region in 1,6-Disubstituted Indoles andIndazoles," J. Med. Chem., vol. 33, pp. 2437-2451, 1990.

U.S. Appl. No. 10/796,396, filed Mar. 9, 2004, Quan et al.

* cited by examiner

BIARYLMETHYL INDOLINES AND INDOLES AS ANTITHROMBOEMBOLIC AGENTS

CROSS-REFERENCE TO RELATED APPLICATIONS

The present application claims the priority benefit of U.S. Provisional Application No. 60/463,452, filed Apr. 16, 2003, which is expressly incorporated fully herein by reference.

FIELD OF THE INVENTION

The present invention relates generally to compounds that inhibit serine proteases. In particular it is directed to novel biarylmethyl indoline, indole and tetrahydroquinoline derivatives of Formula (I):

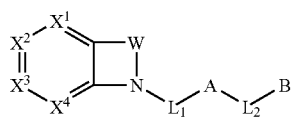

or a stereoisomer or pharmaceutically acceptable salt or hydrate form thereof, which are useful as selective inhibitors of serine protease enzymes of the coagulation cascade and/or contact activation system; for example thrombin, factor XIa, factor Xa, factor IXa, factor VIIa, and/or plasma kallikrein. In particular, it relates to compounds that are selective factor XIa inhibitors. This invention also relates to pharmaceutical compositions comprising these compounds and methods of using the same.

BACKGROUND OF THE INVENTION

Factor XIa is a plasma serine protease involved in the regulation of blood coagulation. While blood coagulation is a necessary and important part of the regulation of an organism's homeostasis, abnormal blood coagulation can also have deleterious effects. For instance, thrombosis is the formation or presence of a blood clot inside a blood vessel or cavity of the heart. Such a blood clot can lodge in a blood vessel blocking circulation and inducing a heart attack or stroke. Thromboembolic disorders are the largest cause of mortality and disability in the industrialized world.

Blood coagulation is initiated in vivo by the binding of tissue factor (TF) to Factor VII (FVII) to generate Factor VIIa (FVIIa). The resulting TF:FVIIa complex activates Factor IX (FIX) and Factor X (FX) which leads to the production of Factor Xa (FXa). The FXa that is generated catalyzes the transformation of prothrombin into small amounts of thrombin before this pathway is shut down by tissue factor pathway inhibitor (TFPI). The process of coagulation is then further propagated via the feedback activation of Factors V, VIII and XI by catalytic amounts of thrombin. (Walsh, P. N. *Thromb. Haemostasis.* 1999, 82, 234–242.) Factor XIa plays a key role in propagating this amplification loop and is thus an attractive target for antithrombotic therapy.

An alternative way of initiation of coagulation is operative when blood is exposed to artificial surfaces (e.g., during hemodialysis, 'on-pump' cardiovascular surgery, vessel grafts, bacterial sepsis). This process is also termed contact activation. Surface absorption of factor XII leads to a conformational change in the factor XII molecule, thereby facilitating activation to proteolytic active factor XII molecules (factor XIIa and factor XIIf). Factor XIIa (or XIIf) has a number of target proteins, including plasma prekallikrein and factor XI. Active plasma kallikrein further activates factor XII, leading to an amplification of contact activation. Contact activation is a surface mediated process responsible in part for the regulation of thrombosis and inflammation, and is mediated, at least in part, by fibrinolytic-, complement-, kininogen/kinin-, and other humoral and cellular pathways (for review, Coleman, R. *Contact Activation Pathway*, pages 103–122 in *Hemostasis and Thrombosis*, Lippincott Williams & Wilkins 2001; Schmaier A. H. *Contact Activation*, pages 105–128 in *Thrombosis and Hemorrhage*, 1998).

Factor XI is a zymogen of a trypsin-like serine protease and is present in plasma at a relatively low concentration. Proteolytic activation at an internal R369-I370 bond yields a heavy chain (369 amino acids) and a light chain (238 amino acids). The latter contains a typical trypsin-like catalytic triad (H413, D464, and S557). Activation of factor XI by thrombin is believed to occur on negatively charged surfaces, most likely on the surface of activated platelets. Platelets contain high affinity (0.8 nM) specific sites (130–500/platelet) for activated factor XI. After activation, factor XIa remains surface bound and recognizes factor IX as its normal macromolecular substrate. (Galiani, D. *Trends Cardiovasc. Med.* 2000, 10, 198–204.)

In addition to the feedback activation mechanisms described above, thrombin activates thrombin activated fibrinolysis inhibitor (TAFI), a plasma carboxypeptidase that cleaves C-terminal lysine and arginine residues on fibrin, reducing the ability of fibrin to enhance tissue-type plasminogen activator (tPA) dependent plasminogen activation. In the presence of antibodies to FXIa, clot lysis can occur more rapidly independent of plasma TAFI concentration. (Bouma, B. N. et al. *Thromb. Res.* 2001, 101, 329–354.) Thus, inhibitors of factor XIa are expected to be anticoagulant and profibrinolytic.

Genetic evidence indicates that factor XI is not required for normal homeostasis, implying a superior safety profile of the factor XI mechanism compared to competing antithrombotic mechanisms. In contrast to hemophilia A (factor VIII deficiency) or hemophilia B (factor IX deficiency), mutations of the factor XI gene causing factor XI deficiency (hemophilia C) result in only a mild to moderate bleeding diathesis characterized primarily by postoperative or posttraumatic, but rarely spontaneous hemorrhage. Postoperative bleeding occurs mostly in tissue with high concentrations of endogenous fibrinolytic activity (e.g., oral cavity, and urogenital system). The majority of the cases are fortuitously identified by preoperative prolongation of APTT (intrinsic system) without any prior bleeding history.

The increased safety of inhibition of XIa as an anticoagulation therapy is further supported by the fact that Factor XI knock-out mice, which have no detectable factor XI protein, undergo normal development, and have a normal life span. No evidence for spontaneous bleeding has been noted. The APTT (intrinsic system) is prolonged in a gene dose-dependent fashion. Interestingly, even after severe stimulation of the coagulation system (tail transaction), the bleeding time is not significantly prolonged compared to wild-type and heterozygous litter mates. (Gailani, D. *Frontiers in Bioscience* 2001, 6, 201–207; Gailani, D. et al. *Blood Coagulation and Fibrinolysis* 1997, 8, 134–144.) Taken together, these observations suggest that high levels of inhibition of factor XIa should be well tolerated. This is in contrast to gene targeting experiments with other coagulation factors.

In vivo activation of factor XI can be determined by complex formation with either C1 inhibitor or alpha 1 antitrypsin. In a study of 50 patients with acute myocardial infarction (AMI), approximately 25% of the patients had values above the upper normal range of the complex ELISA. This study can be viewed as evidence that at least in a subpopulation of patients with AMI, factor XI activation contributes to thrombin formation (Minnema, M. C. et al. *Arterioscler. Thromb. Vasc. Biol.* 2000, 20, 2489–2493). A second study establishes a positive correlation between the extent of coronary arteriosclerosis and factor XIa in complex with alpha 1 antitrypsin (Murakami, T. et al. *Arterioscler Thromb Vasc Biol* 1995, 15, 1107–1113.). In another study, Factor XI levels above the 90$^{th}$ percentile in patients were associated with a 2.2-fold increased risk for venous thrombosis (Meijers, J. C. M. et al. *N. Engl. J. Med.* 2000, 342, 696–701.).

Plasma kallikrein is a zymogen of a trypsin-like serine protease and is present in plasma at 35 to 50 μg/mL. The gene structure is similar to that of factor XI. Overall, the amino acid sequence of plasma kallikrein has 58% homology to factor XI. Proteolytic activation by factor XIIa at an internal I389-R390 bond yields a heavy chain (371 amino acids) and a light chain (248 amino acids). The active site of kallikrein is contained in the light chain. The light chain of plasma kallikrein reacts with protease inhibitors, including alpha 2 macroglobulin and C1-inhibitor. Interestingly, heparin significantly accelerates the inhibition of plasma kallikrein by antithrombin III in the presence of high molecular weight kininogen (HMWK). In blood, the majority of plasma kallikrein circulates in complex with HMWK. Kallikrein cleaves HMWK to liberate bradykinin. Bradykinin release results in increase of vascular permeability and vasodilation (for review, Coleman, R. *Contact Activation Pathway*, pages 103–122 in *Hemostasis and Thrombosis*, Lippincott Williams & Wilkins 2001; Schmaier A. H. *Contact Activation*, pages 105–128 in *Thrombosis and Hemorrhage*, 1998).

Proteins or peptides that reportedly inhibit Factor XIa are disclosed in WO 01/27079. There are advantages in using small organic compounds, however, in preparing pharmaceuticals, e.g., small compounds generally have better oral bioavailability and compatibility in making formulations to aid in delivery of the drug as compared with large proteins or peptides. Small molecule inhibitors of Factor XIa are disclosed in WO 99/12935 and WO 02/42273.

The present invention discloses novel biarylmethyl indoline, indole and tetrahydroquinoline derivatives that are selective, non-peptide inhibitors of coagulation Factor XIa and/or plasma kallikrein and as such are useful in the treatment of thromboembolic and/or inflammatory disorders.

In addition, it is also desirable to find new compounds with improved pharmacological characteristics compared with known serine protease inhibitors. For example, it is preferred to find new compounds with improved factor XIa inhibitory activity and selectivity for factor XIa versus other serine proteases. Also, it is preferred to find new compounds with improved plasma kallikrein inhibitory activity and selectivity for plasma kallikrein versus other serine proteases. It is also desirable and preferable to find compounds with advantageous and improved characteristics in one or more of the following categories, but are not limited to: (a) pharmaceutical properties; (b) dosage requirements; (c) factors which decrease blood concentration peak-to-trough characteristics; (d) factors that increase the concentration of active drug at the receptor; (e) factors that decrease the liability for clinical drug-drug interactions; (f) factors that decrease the potential for adverse side-effects; and (g) factors that improve manufacturing costs or feasibility.

SUMMARY OF THE INVENTION

Accordingly, the present invention provides novel biarylmethyl indoline, indole and tetrahydroquinoline derivatives, and analogues thereof, which are useful as selective inhibitors of serine protease enzymes, especially factor XIa and/or plasma kallikrein, or stereoisomers or pharmaceutically acceptable salts, hydrates, or prodrugs thereof.

The present invention also provides pharmaceutical compositions comprising a pharmaceutically acceptable carrier and a therapeutically effective amount of at least one of the compounds of the present invention or a pharmaceutically acceptable salt, hydrate or prodrug form thereof.

The present invention also provides a method for modulation of the coagulation cascade and/or the contact activation system comprising administering to a host in need of such treatment a therapeutically effective amount of at least one of the compounds of the present invention or a pharmaceutically acceptable salt, hydrate, or prodrug form thereof.

The present invention also provides a method for treating thromboembolic disorders comprising administering to a host in need of such treatment a therapeutically effective amount of at least one of the compounds of the present invention or a pharmaceutically acceptable salt, hydrate, or prodrug form thereof.

The present invention also provides a method for treating inflammatory diseases disorders comprising administering to a host in need of such treatment a therapeutically effective amount of at least one of the compounds of the present invention or a pharmaceutically acceptable sal, hydrate, or prodrug form thereof.

The present invention also provides novel biarylmethyl indoline, indole and tetrahydroquinoline derivatives, and analogues thereof, for use in therapy.

The present invention also provides the use of biarylmethyl indoline, indole and tetrahydroquinoline derivatives, and analogues thereof, for the manufacture of a medicament for the treatment of a thromboembolic disorder.

The present invention also provides the use of biarylmethyl indoline, indole and tetrahydroquinoline derivatives, and analogues thereof, for the manufacture of a medicament for the treatment of an inflammatory disorder.

These and other embodiments, which will become apparent during the following detailed description, have been achieved by the inventors' discovery that the presently claimed novel compounds of the present invention, or pharmaceutically acceptable salt or prodrug forms thereof, are effective factor XIa inhibitors and/or plasma kallikrein inhibitors.

DETAILED DESCRIPTION OF THE INVENTION

In a first aspect, the present invention provides, inter alia, compounds of Formula (I):

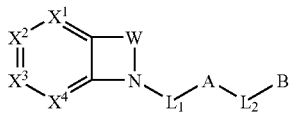

(I)

or a stereoisomer or pharmaceutically acceptable salts, hydrates, or prodrugs thereof, wherein:

W is —CH$_2$CH$_2$—, —CH$_2$CR$^4$R$^5$—, —CR$^4$R$^5$CH$_2$—, —CHR$^4$CHR$^5$—, —CH═CH—, —CR$^4$═CR$^5$—, —CR$^4$═N—, —CH$_2$CH$_2$CH$_2$—, or —CR$^4$R$^5$CH$_2$CH$_2$—;

L$_1$ is —CH$_2$—, —CH$_2$CH$_2$—, —CH$_2$S(O)$_p$—, or —CH$_2$C(O)—;

L$_2$ is a bond, —(CR$^6$R$^{6a}$)$_{1-2}$—, —O—, —NR$^7$—, —C(O)—, —S(O)$_p$—, —(CR$^6$R$^{6a}$)C(O)—, —C(O)(CR$^6$R$^{6a}$)—, —(CR$^6$R$^{6a}$)O—, —O(CR$^6$R$^{6a}$)—, —(CR$^6$R$^{6a}$)NR$^7$—, —NR$^7$(CR$^6$R$^{6a}$)—, —(CR$^6$R$^{6a}$)S(O)$_p$—, —S(O)$_p$(CR$^6$R$^{6a}$)—, —C(O)O—, —OC(O)—, —C(O)NR$^8$—, —NR$^8$C(O)—, —S(O)NR$^8$—, —S(O)$_2$NR$^8$—, —NR$^8$S(O)—, or —NR$^8$S(O)$_2$—;

A is C$_{3-10}$ carbocycle substituted with 0–3 R$^{11}$ and 0–1 R$^{12}$, or a 5–12 membered heterocycle consisting of: carbon atoms and 1–4 heteroatoms selected from the group consisting of N, O, and S(O)$_p$, and substituted 0–3 R$^{11}$ and 0–1 R$^{12}$;

B is C$_{1-6}$ alkyl substituted with 0–2 R$^{11}$ and 0–1 R$^{12}$, C$_{2-6}$ alkenyl substituted with 0–2 R$^{11}$ and 0–1 R$^{12}$, C$_{2-6}$ alkynyl substituted with 0–2 R$^{11}$ and 0–1 R$^{12}$, C$_{3-10}$ carbocycle substituted with 0–3 R$^{11}$ and 0–1 R$^{12}$, or a 5–12 membered heterocycle consisting of: carbon atoms and 1–4 heteroatoms selected from the group consisting of N, O, and S(O)$_p$, and substituted with 0–3 R$^{11}$ and 0–1 R$^{12}$;

X$^1$, X$^2$, X$^3$ and X$^4$ independently represent CR$^1$, CR$^2$, CR$^3$ or N;

R$^1$ is H, —NH$_2$, —NH(C$_{1-3}$ alkyl), —N(C$_{1-3}$ alkyl)$_2$, —C(═NH)NH$_2$, —NHC(═NH)NH$_2$, —C(O)NH$_2$, —CH$_2$NH$_2$, —CH$_2$NH(C$_{1-3}$ alkyl), —CH$_2$N(C$_{1-3}$ alkyl)$_2$, —CH$_2$CH$_2$NH$_2$, —CH$_2$CH$_2$NH(C$_{1-3}$ alkyl), —CH$_2$CH$_2$N(C$_{1-3}$ alkyl)$_2$, —C(═NR$^8$)NR$^7$R$^9$, —NHC(═NR$^8$)NR$^7$R$^9$, —ONHC(═NR$^8$)NR$^7$R$^9$, —NR$^8$CH(═NR$^7$), —C(═NR$^{8a}$)NR$^7$R$^9$, —NR$^8$CH(═NR$^{8a}$), —ONHC(═NR$^{8a}$)NR$^7$R$^8$, —NHC(═NR$^{8a}$)NR$^7$R$^9$, —NR$^7$R$^8$, —C(O)NR$^{7a}$R$^8$, —S(O)$_p$NR$^8$R$^9$, F, Cl, Br, I, OCF$_3$, CF$_3$, OR$^a$, SR$^a$, CN or C$_{1-6}$ alkyl substituted with 1 R$^{1a}$;

R$^{1a}$ is —C(═NR$^8$)NR$^7$R$^9$, —NHC(═NR$^8$)NR$^7$R$^9$, —ONHC(═NR$^8$)NR$^7$R$^9$, —C(═NR$^{8a}$)NR$^7$R$^9$, —NR$^8$CH(═NR$^{8a}$), —ONHC(═NR$^{8a}$)NR$^7$R$^8$, —NHC(═NR$^{8a}$)NR$^7$R$^9$, —NR$^8$CH(═NR$^7$), —NR$^7$R$^8$, —C(O)NR$^{7a}$R$^8$, —S(O)$_p$NR$^8$R$^9$, F, OCF$_3$, CF$_3$, OR$^a$, SR$^a$, or CN;

R$^2$ is H, F, Cl, Br, I, OCF$_3$, CF$_3$, OR$^a$, SR$^a$, CN, NO$_2$, —NR$^7$R$^8$, —C(O)NR$^{7a}$R$^8$, —NR$^{10}$C(O)R$^b$, —S(O)$_p$NR$^8$R$^9$, —S(O)R$^c$, —S(O)$_2$R$^c$, C$_{1-6}$ alkyl substituted with 0–2 R$^{2a}$, C$_{2-6}$ alkenyl substituted with 0–2 R$^{2a}$, C$_{2-6}$ alkynyl substituted with 0–2 R$^{2a}$, —(CH$_2$)$_r$—C$_{3-10}$ carbocycle substituted with 0–3 R$^{2b}$, or —(CH$_2$)$_r$-5–10 membered heterocycle consisting of: carbon atoms and 1–4 heteroatoms selected from the group consisting of N, O, and S(O)$_p$, and substituted with 0–3 R$^{2b}$;

each R$^{2a}$ is, independently at each occurrence, H, F, OCF$_3$, CF$_3$, OR$^a$, SR$^a$, CN, —NR$^7$R$^8$, —C(O)NR$^{7a}$R$^8$, —NR$^{10}$C(O)R$^b$, —S(O)$_p$NR$^8$R$^9$, —S(O)R$^c$, or —S(O)$_2$R$^c$;

each R$^{2b}$ is, independently at each occurrence, H, F, Cl, Br, I, OR$^a$, SR$^a$, CN, NO$_2$, CF$_3$, —SO$_2$R$^c$, —NR$^7$R$^8$, C$_{1-6}$ alkyl, C$_{2-6}$ alkenyl, C$_{2-6}$ alkynyl, C$_{3-6}$ cycloalkyl, C$_{1-4}$ haloalkyl, C$_{1-4}$ haloalkyloxy-, C$_{1-4}$ alkyloxy-, C$_{1-4}$ alkylthio-, C$_{1-4}$ alkyl-C(O)—, or C$_{1-4}$ alkyl-C(O)NH—;

alternately, when R$^1$ and R$^2$ are substituted on adjacent ring carbon atoms, they can be taken together with the ring carbon atoms to which they are attached to form a 5–7 membered carbocycle or heterocycle substituted with 0–2 R$^{2b}$;

R$^3$ is H, F, Cl, Br, I, OCF$_3$, CF$_3$, OR$^a$, SR$^a$, CN, NO$_2$, —NR$^7$R$^8$, —C(O)NR$^{7a}$R$^8$, —NR$^{10}$C(O)R$^b$, —S(O)$_p$NR$^8$R$^9$, —S(O)R$^c$, —S(O)$_2$R$^c$, C$_{1-6}$ alkyl substituted with 0–2 R$^{3a}$, C$_{2-6}$ alkenyl substituted with 0–2 R$^{3a}$, C$_{2-6}$ alkynyl substituted with 0–2 R$^{3a}$, —(CH$_2$)$_r$—C$_{3-10}$ carbocycle substituted with 0–3 R$^{3b}$, or —(CH$_2$)$_r$-5–10 membered heterocycle consisting of: carbon atoms and 1–4 heteroatoms selected from the group consisting of N, O, and S(O)$_p$, and substituted with 0–3 R$^{3b}$;

each R$^{3a}$ is, independently at each occurrence, H, F, OCF$_3$, CF$_3$, OR$^a$, SR$^a$, CN, —NR$^7$R$^8$, —C(O)NR$^{7a}$R$^8$, —NR$^{10}$C(O)R$^b$, —S(O)$_p$NR$^8$R$^9$, —S(O)R$^c$, or —S(O)$_2$R$^c$;

each R$^{3b}$ is, independently at each occurrence, H, F, Cl, Br, I, OR$^a$, SR$^a$, CN, NO$_2$, CF$_3$, —SO$_2$R$^c$, —NR$^7$R$^8$, C$_{1-6}$ alkyl, C$_{2-6}$ alkenyl, C$_{2-6}$ alkynyl, C$_{3-6}$ cycloalkyl, C$_{1-4}$ haloalkyl, C$_{1-4}$ haloalkyloxy-, C$_{1-4}$ alkyloxy-, C$_{1-4}$ alkylthio-, C$_{1-4}$ alkyl-C(O)—, or C$_{1-4}$ alkyl-C(O)NH—;

R$^4$ is H, F, OR$^a$, SR$^a$, —NR$^7$R$^8$, —NR$^{10}$C(O)NR$^{7a}$R$^8$, —NR$^{10}$SO$_2$R$^c$, —C(O)OR$^a$, —(CH$_2$)$_r$—C(O)NR$^{7a}$R$^8$, C$_{1-4}$ haloalkyl, C$_{1-6}$ alkyl substituted with 0–3 R$^{4a}$, C$_{2-6}$ alkenyl substituted with 0–3 R$^{4a}$, C$_{2-6}$ alkynyl substituted with 0–3 R$^{4a}$, —(CH$_2$)$_r$—C$_{3-10}$ carbocycle substituted with 0–3 R$^{4b}$, or —(CH$_2$)$_r$-5–10 membered heterocycle consisting of: carbon atoms and 1–4 heteroatoms selected from the group consisting of N, O, and S(O)$_p$, and substituted with 0–3 R$^{4b}$;

each R$^{4a}$ is, independently at each occurrence, H, C$_{1-4}$ alkyl, OR$^a$, F, ═O, CF$_3$, CN, —C(O)R$^a$, —C(O)OR$^a$, —C(O)NR$^{7a}$R$^8$, —NR$^{10}$COR$^c$, or —S(O)$_p$R$^b$;

each R$^{4b}$ is, independently at each occurrence, H, OH, Cl, F, Br, I, CN, NO$_2$, CF$_3$, —C(O)OR$^a$, —SO$_2$R$^c$, —NR$^7$R$^8$, C$_{1-6}$ alkyl, C$_{2-6}$ alkenyl, C$_{2-6}$ alkynyl, C$_{3-6}$ cycloalkyl, C$_{1-4}$ haloalkyl, C$_{1-4}$ haloalkyloxy-, C$_{1-4}$ alkyloxy-, C$_{1-4}$ alkylthio-, C$_{1-4}$ alkyl-C(O)—, C$_{1-4}$ alkyl-C(O)NH—, —C(O)NR$^{7a}$R$^8$, —NR$^{10}$C(O)R$^c$, —NR$^{10}$S(O)$_2$NR$^8$R$^9$, or —S(O)$_2$NR$^8$R$^9$;

R$^5$ is H, F, C$_{1-4}$ haloalkyl, C$_{1-6}$ alkyl substituted with 0–3 R$^{5a}$, C$_{2-6}$ alkenyl substituted with 0–3 R$^{5a}$, C$_{2-6}$ alkynyl substituted with 0–3 R$^{5a}$, —(CH$_2$)$_r$—C$_{3-10}$ carbocycle substituted with 0–3 R$^{5b}$, or —(CH$_2$)$_r$-5–10 membered heterocycle consisting of: carbon atoms and 1–4 heteroatoms selected from the group consisting of N, O, and S(O)$_p$, and substituted with 0–3 R$^{5b}$;

each R$^{5a}$ is, independently at each occurrence, H, C$_{1-4}$ alkyl, OR$^a$, F, ═O, CF$_3$, CN, —C(O)R$^a$, —C(O)OR$^a$, —C(O)NR$^{7a}$R$^8$, or —S(O)$_p$R$^c$;

each R$^{5b}$ is, independently at each occurrence, H, OH, Cl, F, Br, I, CN, NO$_2$, CF$_3$, —C(O)OR$^a$, —SO$_2$R$^c$, —NR$^7$R$^8$, C$_{1-6}$ alkyl, C$_{2-6}$ alkenyl, C$_{2-6}$ alkynyl, C$_{3-6}$ cycloalkyl, C$_{1-4}$ haloalkyl, C$_{1-4}$ haloalkyloxy-, C$_{1-4}$ alkyloxy-, C$_{1-4}$ alkylthio-, C$_{1-4}$ alkyl-C(O)—, or C$_{1-4}$ alkyl-C(O)NH—;

each R$^7$ is, independently at each occurrence, H, C$_{1-6}$ alkyl, —(CH$_2$)$_n$-phenyl, (C$_{1-6}$ alkyl)C(O)—, (C$_{6-10}$ aryl)—C$_{0-4}$ alkyl-C(O)—, (C$_{3-6}$ cycloalkyl)—C$_{0-4}$ alkyl-C(O)—, (5–10 membered heteroaryl)—C$_{0-4}$ alkyl-C(O)—, (C$_{1-4}$ alkyl)OC(O)—, (C$_{6-10}$ aryl)—C$_{1-4}$ alkyl-OC(O)—, (C$_{1-4}$ alkyl)—C(O)O—(C$_{1-4}$ alkyl)—OC(O)—, (C$_{6-10}$ aryl)—C(O)O—(C$_{1-4}$ alkyl)—OC(O)—, (5–10 membered heteroaryl)—CH$_2$—OC(O)—, (C$_{1-6}$ alkyl)—NHC(O)—, (C$_{6-10}$ aryl)—C$_{0-4}$ alkyl-NHC(O)—, (5–10 membered heteroaryl)—C$_{0-4}$ alkyl-NHC(O)—, (C$_{1-6}$ alkyl)—S(O)$_2$—, ($C_{6-10}$ aryl)—($C_{0-4}$ alkyl)—$S(O)_2$—, (5–10 membered heteroaryl)—$C_{0-4}$ alkyl-$S(O)_2$—, ($C_{1-6}$ alkyl)$_2$NC(O)—, phenyl-NHC(O)—, or (phenyl)($C_{1-6}$ alkyl)NHC(O)—, wherein said phenyl, aryl and heteroaryl are substituted with 0–2 $R^f$;

each $R^{7a}$ is, independently at each occurrence, H, $C_{1-4}$ alkyl substituted with 0–2 $R^{7b}$ and/or 0–2 $R^{7c}$, —($CH_2$)$_r$—$C_{3-10}$ carbocycle substituted with 0–3 $R^f$, or a —($CH_2$)$_r$-5–12 membered heterocycle consisting of: carbon atoms and 1–4 heteroatoms selected from the group consisting of N, O, and $S(O)_p$, and substituted 0–3 $R^f$;

each $R^{7b}$ is, independently at each occurrence, =O, $OR^g$, F, CN, $NO_2$, —$NR^7R^8$, —$C(O)R^g$, —$C(O)OR^g$, —$NR^8C(O)R^g$, —$C(O)NR^8R^9$, —$NR^8C(O)NR^8R^9$, —$SO_2NR^8R^9$, —$NR^8SO_2NR^8R^9$, —$NR^8SO_2$—$C_{1-4}$ alkyl, —$NR^8SO_2CF_3$, —$NR^8SO_2$-phenyl, —$S(O)_2CF_3$, —$S(O)_p$—$C_{1-4}$ alkyl, —$S(O)_p$-phenyl, or —$(CF_2)_rCF_3$;

each $R^{7c}$ is, independently at each occurrence, $C_{3-10}$ carbocycle substituted with 0–3 $R^f$; or a 5–12 membered heterocycle consisting of: carbon atoms and 1–4 heteroatoms selected from the group consisting of N, O, and $S(O)_p$, and substituted 0–3 $R^f$;

each $R^8$ is, independently at each occurrence, H, $C_{1-6}$ alkyl, or —($CH_2$)$_n$-phenyl;

each $R^{8a}$ is, independently at each occurrence, H, OH, $C_{1-6}$ alkyl, $C_{1-4}$ alkoxy, ($C_{6-10}$ aryl)—$C_{1-4}$ alkoxy, —($CH_2$)$_n$-phenyl, ($C_{1-6}$ alkyl)C(O)—, ($C_{6-10}$ aryl)—$C_{0-4}$ alkyl-C(O)—, ($C_{3-6}$ cycloalkyl)—$C_{0-4}$ alkyl-C(O)—, (5–10 membered heteroaryl)—$C_{0-4}$ alkyl-C(O)—, ($C_{1-4}$ alkyl)OC(O)—, ($C_{6-10}$ aryl)—$C_{1-4}$ alkyl-OC(O)—, ($C_{1-4}$ alkyl)—C(O)O—($C_{1-4}$ alkyl)—OC(O)—, ($C_{6-10}$ aryl)—C(O)O—($C_{1-4}$ alkyl)—OC(O)—, (5–10 membered heteroaryl)—$C_{0-4}$ alkyl-OC(O)—, $C_{1-4}$ alkoxy, ($C_{1-4}$ alkyl)C(O)O—, or ($C_{6-10}$ aryl)—($C_{0-4}$ alkyl)—C(O)O—; wherein said phenyl, aryl and heteroaryl are substituted with 0–2 $R^f$;

alternatively, $R^7$ and $R^8$, or $R^{7a}$ and $R^8$, when attached to the same nitrogen, combine to form a 5–10 membered heterocyclic ring consisting of carbon atoms and 0–2 additional heteroatoms selected from the group consisting of N, O, and $S(O)_p$, and optionally substituted with 0–2 $R^d$;

each $R^9$ is, independently at each occurrence, H, $C_{1-6}$ alkyl, or —($CH_2$)$_n$-phenyl;

each $R^{10}$ is, independently at each occurrence, H, $C_{1-6}$ alkyl substituted with 0–2 $R^{10a}$, $C_{2-6}$ alkenyl substituted with 0–2 $R^{10a}$, $C_{2-6}$ alkynyl substituted with 0–2 $R^{10a}$, —($CH_2$)$_r$—$C_{3-10}$ carbocycle substituted with 0–3 $R^d$, or —($CH_2$)$_r$-5–10 membered heterocycle consisting of carbon atoms and 1–4 heteroatoms selected from the group consisting of N, O, and $S(O)_p$, and substituted with 0–3 $R^d$;

each $R^{10a}$ is, independently at each occurrence, H, $C_{1-4}$ alkyl, $OR^a$, F, =O, $CF_3$, CN, $NO_2$, —$C(O)R^a$, —$C(O)OR^a$, —$C(O)NR^{7a}R^8$, or —$S(O)_pR^c$;

each $R^{11}$ is, independently at each occurrence, H, =O, —($CH_2$)$_r$—$OR^a$, F, Cl, Br, I, $CF_3$, CN, $NO_2$, —($CH_2$)$_r$—$NR^7R^8$, —($CH_2$)$_r$—C(=$NR^8$)$NR^7R^9$, —$C(O)R^a$, —C(O)$OR^a$, —($CH_2$)$_r$—$NR^8C(O)R^a$, —$NR^8C(O)OR^c$, —$NR^8CO(CH_2)_rCO_2R^a$, —$C(O)NR^{7a}R^8$, —$NR^8C(O)NR^8R^{10}$, —$SO_2NR^8R^{10}$, —$NR^8SO_2NR^8R^{10}$, —$NR^8SO_2$—$C_{1-4}$ alkyl, —$NR^8SO_2CF_3$, —$NR^8SO_2$-phenyl, —$S(O)_2CF_3$, —$S(O)_p$—$C_{1-4}$ alkyl, —$S(O)_p$-phenyl, —$(CF_2)_rCF_3$, $C_{1-6}$ alkyl substituted with 0–2 $R^{11a}$, $C_{2-6}$ alkenyl substituted with 0–2 $R^{11a}$, $C_{2-6}$ alkynyl substituted with 0–2 $R^{11a}$, $C_{1-6}$ alkyl substituted with 0–2 $R^{11b}$, $C_{2-6}$ alkenyl substituted with 0–2 $R^{11b}$, $C_{2-6}$ alkynyl substituted with 0–2 $R^{11b}$, phenyl substituted with 0–3 $R^c$ and/or 0–3 $R^d$, or a 5–7 membered heterocycle consisting of carbon atoms and 1–4 heteroatoms selected from the group consisting of N, O, and $S(O)_p$, and substituted with 0–3 $R^c$ and/or 0–3 $R^d$;

each $R^{11a}$ is, independently at each occurrence, =O, $OR^a$, F, Cl, Br, I, CN, $NO_2$, —$NR^7R^8$, —$C(O)R^a$, —$C(O)OR^a$, —$NR^8C(O)R^a$, —$C(O)NR^{7a}R^8$, —$NR^8C(O)NR^8R^{1o}$, —$SO_2NR^8R^{10}$, —$NR^8SO_2NR^8R^{10}$, —$NR^8SO_2$—$C_{1-4}$ alkyl, —$NR^8SO_2CF_3$, —$NR^8SO_2$-phenyl, —$S(O)_2CF_3$, —$S(O)_p$—$C_{1-4}$ alkyl, —$S(O)_p$-phenyl, or —$(CF_2)_rCF_3$;

each $R^{11b}$ is, independently at each occurrence, $C_{3-10}$ carbocycle substituted with 0–3 $R^d$, or a 5–12 membered heterocycle consisting of: carbon atoms and 1–4 heteroatoms selected from the group consisting of N, O, and $S(O)_p$, and substituted 0–3 $R^d$;

each $R^{12}$ is, independently at each occurrence, $OR^{12a}$, —$CH_2OR^{12a}$, —$C(O)NR^{7a}R^8$, —($CH_2$)$_r$$CO_2R^{12a}$, —($CH_2$)$_r$ $SO_3H$, —$OSO_3H$, —($CH_2$)$_r$$PO_3H$, —$OPO_3H_2$, —$PO_3H_2$, —$NHCOCF_3$, —$NHSO_2CF_3$, —$CONHNHSO_2CF_3$, —$C(CF_3)_2OH$, —$SO_2NHR^{12a}$, —$CONHSO_2NHR^{12a}$, —$SO_2NHCOR^{12a}$, —$SO_2NHCO_2R^{12a}$, —$CONHSO_2R^{12b}$, —$NHSO_2R^{12b}$, —$CONHOR^{12b}$,

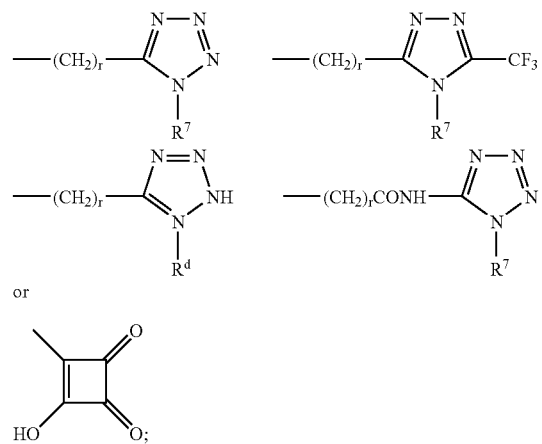

or each $R^{12a}$ is, independently at each occurrence, H, $C_{1-6}$ alkyl, —($CH_2$)$_r$—$C_{3-10}$ carbocycle substituted with 0–3 $R^d$, or —($CH_2$)$_r$-5–10 membered heterocycle consisting of carbon atoms and 1–4 heteroatoms selected from the group consisting of N, O, and $S(O)_p$, and substituted with 0–3 $R^d$;

each $R^{12b}$ is, independently at each occurrence, $C_{1-6}$ alkyl substituted with 0–2 $R^{12c}$, $C_{2-6}$ alkenyl substituted with 0–2 $R^{12c}$, $C_{2-6}$ alkynyl substituted with 0–2 $R^{12c}$, —($CH_2$)$_r$—$C_{3-10}$ carbocycle substituted with 0–3 $R^{12c}$, or —($CH_2$)$_r$-5–10 membered heterocycle consisting of: carbon atoms and 1–4 heteroatoms selected from the group consisting of N, O, and $S(O)_p$, and substituted with 0–3 $R^{12c}$;

each $R^{12c}$ is, independently at each occurrence, H, F, Cl, Br, I, $CF_3$, $OCF_3$, CN, $NO_2$, $OR^a$, —$CO_2R^a$, —$NR^7R^8$, —$SO_2R^c$, $C_{1-6}$ alkyl, $C_{2-6}$ alkenyl, $C_{2-6}$ alkynyl, —($CH_2$)$_r$—$C_{3-10}$ carbocycle substituted with 0–3 $R^d$, or —($CH_2$)$_r$-5–10 membered heterocycle consisting of carbon atoms and 1–4 heteroatoms selected from the group consisting of N, O, and $S(O)_p$, and substituted with 0–3 $R^d$;

each $R^a$ is, independently at each occurrence, H, $C_{1-4}$ alkyl, —($CH_2$)$_r$—$C_{3-7}$ cycloalkyl, —($CH_2$)$_r$—$C_{6-10}$ aryl, or —($CH_2$)$_r$-5–10 membered heteroaryl, wherein said aryl or heteroaryl groups are optionally substituted with 0–2 $R^f$;

each $R^b$ is, independently at each occurrence, $CF_3$, OH, $C_{1-4}$ alkoxy, $C_{1-6}$ alkyl, —($CH_2$)$_r$—$C_{3-10}$ carbocycle substituted with 0–2 $R^d$, or —($CH_2$)$_r$-5–10 membered heterocycle containing from 1–4 heteroatoms selected from the group consisting of N, O, and $S(O)_p$ and substituted with 0–2 $R^d$;

each $R^c$ is, independently at each occurrence, $C_{1-4}$ alkyl, $C_{6-10}$ aryl, 5–10 membered heteroaryl, ($C_{6-10}$ aryl)—$C_{1-4}$ alkyl, or (5–10 membered heteroaryl)—$C_{1-4}$ alkyl, wherein said aryl and heteroaryl groups are substituted with 0–2 $R^d$;

each $R^d$ is, independently at each occurrence, H, =O, $OR^a$, F, Cl, Br, I, CN, $NO_2$, —$NR^7R^8$, —$C(O)R^a$, —$C(O)OR^a$, —$NR^8C(O)R^a$, —$C(O)NR^{7a}R^8$, —$SO_2NR^8R^9$, —$NR^8SO_2NR^8R^9$, —$NR^8SO_2$—$C_{1-4}$ alkyl, —$NR^8SO_2CF_3$, —$NR^8SO_2$-phenyl, —$S(O)_2CF_3$, —$S(O)_p$—$C_{1-4}$ alkyl, —$S(O)_p$-phenyl, —$(CF_2)_rCF_3$, $C_{1-6}$ alkyl substituted with 0–2 $R^e$, $C_{2-6}$ alkenyl substituted with 0–2 $R^e$, or $C_{2-6}$ alkynyl substituted with 0–2 $R^e$;

each $R^e$ is, independently at each occurrence, =O, $OR^a$, F, Cl, Br, I, CN, $NO_2$, —$NR^8R^9$, —$C(O)R^a$, —$C(O)OR^a$, —$NR^8C(O)R^a$, —$C(O)NR^{7a}R^8$, —$SO_2NR^8R^9$, —$NR^8SO_2NR^8R^9$, —$NR^8SO_2$—$C_{1-4}$ alkyl, —$NR^8SO_2CF_3$, —$NR^8SO_2$-phenyl, —$S(O)_2CF_3$, —$S(O)_p$—$C_{1-4}$ alkyl, —$S(O)_p$-phenyl, or —$(CF_2)_rCF_3$;

each $R^f$ is, independently at each occurrence, H, =O, —$(CH_2)_r$—$OR^g$, F, Cl, Br, I, CN, $NO_2$, —$NR^8R^9$, —$C(O)R^g$, —$C(O)OR^g$, —$NR^8C(O)R^g$, —$C(O)NR^8R^9$, —$SO_2NR^8R^9$, —$NR^8SO_2NR^8R^9$, —$NR^8SO_2$—$C_{1-4}$ alkyl, —$NR^8SO_2CF_3$, —$NR^8SO_2$-phenyl, —$S(O)_2CF_3$, —$S(O)_p$—$C_{1-4}$ alkyl, —$S(O)_p$-phenyl, —$(CF_2)_rCF_3$, $C_{1-6}$ alkyl, $C_{2-6}$ alkenyl, or $C_{2-6}$ alkynyl;

each $R^g$ is, independently at each occurrence, H, $C_{1-6}$ alkyl, or —$(CH_2)_n$-phenyl;

n, at each occurrence, is selected from 0, 1, 2, 3, and 4;
p, at each occurrence, is selected from 0, 1, and 2; and
r, at each occurrence, is selected from 0, 1, 2, 3, and 4.

In some embodiments according to the first aspect, the present invention includes compounds of Formula (I) W is —$CH_2CH_2$—, —$CR^4R^5CH_2$—, —CH=CH—, —$CR^4$=CH—, —$CR^4$=N—, —$CH_2CH_2CH_2$—, or —$CR^4R^5CH_2CH_2$—. In other embodiments, the present invention includes compounds of Formula (I) where W is —$CH_2CH_2$—, —CH=CH—, —$C(C_{1-4}$ alkyl)=CH—, —C(benzyl)=CH—, —C(3-pyridylmethyl)=CH—, —CH=N—, —$C(C_{1-4}$ alkyl)=N—, —C(benzyl)=N—, —CH(benzyl)$CH_2$—, —CH(phenyl)$CH_2$ $CH_2$—, —C(Me)(phenyl)$CH_2CH_2$—, —C(3,5-diMe-benzyl)=CH—, —C($CH_2OH$)=CH—, —C(CONHMe)=CH—, —C(CONHPh)=CH—, —C(4-$CO_2H$-benzyl)=CH—, or —C($CH_2CONHMe$)=CH—. In other embodiments, the present invention includes compounds of Formula (I) where W is —$CH_2CH_2$—, —CH=CH—, —$C(C_{1-4}$ alkyl)=CH—, —C(benzyl)=CH—, —CH=N—, —C(ethyl)=N—, —C(benzyl)=N—, or —CH(benzyl)$CH_2$—. In other embodiments, the present invention includes compounds of Formula (I) where W is —$CH_2CH_2$—, —CH=CH—, —C(ethyl)=CH—, or —C(benzyl)=CH—.

In some embodiments according to the first aspect, the present invention includes compounds of Formula (I) where $L_1$ is —$CH_2$—, —$CH_2CH_2$—, or —$CH_2C(O)$—. In other embodiments, the present invention includes compounds of Formula (I) where $L_1$ is —$CH_2$—.

In some embodiments according to the first aspect, the present invention includes compounds of Formula (I) where $L_2$ is a bond, —$(CH_2)_{1-2}$—, —O—, —$NR^7$—, —C(O)—, —$S(O)_p$—, —$(CH_2)C(O)$—, —$C(O)(CH_2)$—, —$(CH_2)$ O—, —$O(CH_2)$—, —$(CH_2)NR^7$—, —$NR^7(CH_2)$—, —$(CH_2)S(O)_p$—, —$S(O)_p(CH_2)$—, —C(O)O—, —OC(O)—, —$C(O)NR^8$—, —$NR^8C(O)$—, —$S(O)NR^8$—, —$S(O)_2NR^8$—, —$NR^8S(O)$—, or —$NR^8S(O)_2$—. In other embodiments, the present invention includes compounds of Formula (I) where $L_2$ is a bond, —$(CH_2)_{1-2}$—, —O—, —$NR^7$—, —C(O)—, —$S(O)_p$—, —$(CH_2) C(O)$—, —$C(O)(CH_2)$—, —$(CH_2)O$—, —$O(CH_2)$—, —$(CH_2)NR^7$—, —$NR^7(CH_2)$—, —C(O)$NR^8$—, —$NR^8C(O)$—, —$S(O)_2NR^8$—, or —$NR^8S(O)_2$—. In other embodiments, the present invention includes compounds of Formula (I) where $L_2$ is a bond, —$(CH_2)_{1-2}$—, —O—, —$NR^{10}$—, —$(CH_2)$ O—, —$O(CH_2)$—, —$(CH_2)NR^{10}$—, —$NR^{10}(CH_2)$—, —CONH—, or —NHCO—. In other embodiments, the present invention includes compounds of Formula (I) where $L_2$ is a bond, —$CH_2$—, —O—, —CONH—, —NHCO—, —$(CH_2)O$—, or —$O(CH_2)$—.

In some embodiments according to the first aspect, the present invention includes compounds of Formula (I) where A is phenyl substituted with 0–2 $R^{11}$ and 0–1 $R^{12}$, or a 5–12 membered heterocycle consisting of: carbon atoms and 1–4 heteroatoms selected from the group consisting of N, O, and $S(O)_p$, and substituted 0–2 $R^{11}$ and 0–1 $R^{12}$. In other embodiments, the present invention includes compounds of Formula (I) where A is phenyl substituted with 0–2 $R^{11}$, or pyridyl substituted with 0–2 $R^{11}$. In other embodiments, the present invention includes compounds of Formula (I) where A is 1,2-phenylene, 3-carboxy-1,2-phenylene, 4-methyl-1,2-phenylene, 4-methoxy-1,2-phenylene, 4-aminomethyl-1,2-phenylene, 4-amidino-1,2-phenylene, 4-amidinomethyl-1,2-phenylene, 4-acetoamidomethyl-1,2-phenylene, 5-(N,N-dimethylaminoethylcarbamoyl)-1,2-phenylene, 5-carboxy-1,2-phenylene, 5-hydroxymethyl-1,2-phenylene, 5-acetylamino-1,2-phenylene, 5-propionylamino-1,2-phenylene, 5-butyrylamino-1,2-phenylene, 5-(3-methylbutyrylamino)-1,2-phenylene, 5-(2,2-dimethylpropionylamino)-1,2-phenylene, 5-benzylcarbonylamino-1,2-phenylene, 4-methoxy-5-hydroxy-1,2-phenylene, 5-carbamoyl-1,2-phenylene, 5-methylcarbamoyl-1,2-phenylene, 5-ethylcarbamoyl-1,2-phenylene, 5-propylcarbamoyl-1,2-phenylene, 5-isopropylcarbamoyl-1,2-phenylene, 5-isobutylcarbamoyl-1,2-phenylene, 5-t-butylcarbamoyl-1,2-phenylene, 5-isoamylcarbamoyl-1,2-phenylene, 5-(carboxymethyl)carbamoyl-1,2-phenylene, 5-(2-carboxyethyl)carbamoyl-1,2-phenylene, 5-(3-hydroxypropyl)carbamoyl-1,2-phenylene, 5-(3-carboxypropyl)carbamoyl-1,2-phenylene, 5-(cyclopropylmethyl)carbamoyl-1,2-phenylene, 5-(cyclohexylmethyl)carbamoyl-1,2-phenylene, 5-phenylcarbamoyl-1,2-phenylene, 5-benzylcarbamoyl-1,2-phenylene, 5-(1-phenylethyl)carbamoyl-1,2-phenylene, 5-phenethylcarbamoyl-1,2-phenylene, 5-(3-phenylpropyl-carbamoyl)-1,2-phenylene, 5-(4-methoxybenzyl)carbamoyl-1,2-phenylene, 5-(3,5,dimethoxybenzyl)carbamoyl-1,2-phenylene, 5-(4-chlorobenzyl)carbamoyl-1,2-phenylene, 5-[2-(3-chloropheny)ethyl]carbamoyl-1,2-phenylene, 5-(2-pyridylmethyl)carbamoyl-1,2-phenylene, 5-(3-pyridylmethyl)carbamoyl-1,2-phenylene, 5-[2-(2-pyridyl)ethyl]carbamoyl-1,2-phenylene, 5-(4-tetrahydropyranyl)methylcarbamoyl-1,2-phenylene, 5-(morpholine-4-carbonyl)-1,2-phenylene, 5-[4-(2-hydroxyethyl)-piperdine-1-carbonyl]-1,2-phenylene, 5-[4-(2-methoxyethyl)-piperdine-1-carbonyl]-1,2-phenylene, 5-[4-(ethoxycarbonylmethyl)-piperdine-1-carbonyl]-1,2-phenylene, 5-(1-naphthyl)carbamoyl-1,2-phenylene, 5-(1-indanyl)carbamoyl-1,2-phenylene, 1,3-phenylene, 5-amino-1,3-phenylene, 5-acetylamino-1,3-phenylene, 5-propionylamino-1,3-phenylene, 5-butyrylamino-1,3-phenylene, 5-(3-methylbutyrylamino)-1,2-phenylene, 5-(2,2-dimethylpropionylamino)-1,2-phenylene, or 6-amino-2,3-pyridylene; wherein the attachment to $L_2$ is at carbon 1 of said phenylene rings.

In some embodiments according to the first aspect, the present invention includes compounds of Formula (I) where B is phenyl substituted with 0–2 $R^{11}$ and 0–1 $R^{12}$, or a 5–7 membered heterocycle consisting of: carbon atoms and 1–4 heteroatoms selected from the group consisting of N, O, and $S(O)_p$, and substituted with 0–2 $R^{11}$ and 0–1 $R^{12}$. In other embodiments, the present invention includes compounds of Formula (I) where B is phenyl substituted with 0–2 $R^{11}$ and 0–1 $R^{12}$, or pyridyl substituted with 0–2 $R^{11}$ and 0–1 $R^{12}$. In other embodiments, the present invention includes compounds of Formula (I) where B is 2-carboxy-phenyl, 2-aminosulfonyl-phenyl, 3-carboxymethyl-phenyl, 2,4-dicarboxy-phenyl, 2,4-dimethoxycarbonyl-phenyl, 2,4-dicarbamoyl-phenyl, 2-carboxy-4-methoxycarbonyl-phenyl, 2-carboxy-4-methyl-phenyl, 2-carboxy-4-methoxy-phenyl, 2-carboxy-4-ethoxy-phenyl, 2-carboxy-4-fluoro-phenyl, 2-carboxy-4-amino-phenyl, 2-carboxy-4-cyano-phenyl, 2-carboxy-4-acetylamino-phenyl, 2-carboxy-4-carbamoyl-phenyl, 2,5-dicarboxy-phenyl, 2,5-dicarboxy-4-methoxy-phenyl, 2-carboxy-4,5-dimethoxy-phenyl, 2-carboxy-4-triflouromethyl-phenyl, 5-carboxy-4-methoxy-phenyl, 3-carboxy-4-pyridyl, or 2-carboxy-6-methoxy-3-pyridyl.

In some embodiments according to the first aspect, the present invention includes compounds of Formula (I) where $R^1$ is H, F, Cl, —$NH_2$, —$NH(C_{1-3}$ alkyl), —$N(C_{1-3}$ alkyl)$_2$, —C(=NH)$NH_2$, —NHC(=NH)$NH_2$, —C(O)$NH_2$, —$CH_2NH_2$, —$CH_2NH(C_{1-3}$ alkyl), —$CH_2N(C_{1-3}$ alkyl)$_2$, —C(=$NR^8$)$NR^7R^9$, —NHC(=$NR^8$)$NR^7R^9$, —$NR^8$CH(=$NR^7$), —C(=$NR^{8a}$)$NR^7R^9$, —NHC(=$NR^{8a}$)$NR^7R^9$, —$NR^7R^8$, —C(O)$NR^{7a}R^8$, —$S(O)_pNR^8R^9$, $OR^a$, or CN. In other embodiments, the present invention includes compounds of Formula (I) where $R^1$ is H, F, Cl, $NH_2$, —C(=NH)$NH_2$, —C(=$NR^{8a}$)$NH_2$, —C(=O)$NH_2$, —$CH_2NH_2$, —C(O)$NR^{7a}R^8$, OMe, or CN. In other embodiments, the present invention includes compounds of Formula (I) where $R^1$ is —C(=NH)$NH_2$, —C(=NOH)$NH_2$—, —C(=$NCO_2Et$)$NH_2$—, —$CH_2NH_2$, —C(=O)$NH_2$, H, F, Cl, $NH_2$ or OMe.

In some embodiments according to the first aspect, the present invention includes compounds of Formula (I) where $R^2$ is H, F, $OR^a$, CN, —$NR^7R^8$, —C(O)$NR^{7a}R^8$, —$NR^{10}C(O)R^b$, —$S(O)_pNR^8R^9$, —$S(O)R^c$, —$S(O)_2R^c$, $C_{1-6}$ alkyl substituted with 0–2 $R^{2a}$, —$(CH_2)_r$—$C_{3-7}$ carbocycle substituted with 0–2 $R^{2b}$, or —$(CH_2)_r$-5–7 membered heterocycle consisting of: carbon atoms and 1–4 heteroatoms selected from the group consisting of N, O, and $S(O)_p$, and substituted with 0–2 $R^{2b}$. In other embodiments, the present invention includes compounds of Formula (I) where $R^2$ is H, F, $OR^a$, CN, —$NR^7R^8$, —C(O)$NR^{7a}R^8$, —$NR^{10}C(O)R^b$, —$S(O)_pNR^8R^9$, or $C_{1-6}$ alkyl substituted with 0–1 $R^{2a}$. In other embodiments, the present invention includes compounds of Formula (I) where $R^2$ is H, F, OMe, OEt, CN, —$NH_2$, —C(O)$NH_2$, or $C_{1-6}$ alkyl.

In some embodiments according to the first aspect, the present invention includes compounds of Formula (I) where $R^3$ is H, F, $OR^a$, CN, —$NR^7R^8$, —C(O)$NR^{7a}R^8$, —$NR^{10}C(O)R^b$, —$S(O)_pNR^8R^9$, —$S(O)R^c$, —$S(O)_2R^c$, $C_{1-6}$ alkyl substituted with 0–2 $R^{3a}$, —$(CH_2)_r$—$C_{3-7}$ carbocycle substituted with 0–2 $R^{3b}$, or —$(CH_2)_r$-5–7 membered heterocycle consisting of: carbon atoms and 1–4 heteroatoms selected from the group consisting of N, O, and $S(O)_p$, and substituted with 0–2 $R^{3b}$. In other embodiments, the present invention includes compounds of Formula (I) where $R^3$ is H, F, $OR^a$, CN, —$NR^7R^8$, —C(O)$NR^{7a}R^8$, —$NR^{10}C(O)R^b$, —$S(O)_pNR^8R^9$, or $C_{1-6}$ alkyl substituted with 0–1 $R^{3a}$. In other embodiments, the present invention includes compounds of Formula (I) where $R^3$ is H, F, OMe, OEt, CN, —$NH_2$, —C(O)$NH_2$, or $C_{1-6}$ alkyl.

In some embodiments according to the first aspect, the present invention includes compounds of Formula (I) where $R^4$ is H, F, $C_{1-4}$ haloalkyl, —$(CH_2)_r$—C(O)$NR^{7a}R^8$, $C_{1-6}$ alkyl substituted with 0–2 $R^{4a}$, $C_{2-6}$ alkenyl substituted with 0–2 $R^{4a}$, $C_{2-6}$ alkynyl substituted with 0–2 $R^{4a}$, —$(CH_2)_r$—$C_{3-8}$ carbocycle substituted with 0–3 $R^{4b}$, or —$(CH_2)_r$-5–6 membered heterocycle consisting of: carbon atoms and 1–4 heteroatoms selected from the group consisting of N, O, and $S(O)_p$, and substituted with 0–3 $R^{4b}$. In other embodiments, the present invention includes compounds of Formula (I) where $R^4$ is H, $C_{1-4}$ haloalkyl, —$(CH_2)_r$—C(O)$NR^{7a}R^8$, $C_{1-4}$ alkyl substituted with 0–2 $R^{4a}$, $C_{2-4}$ alkenyl substituted with 0–2 $R^{4a}$, $C_{2-4}$ alkynyl substituted with 0–2 $R^{4a}$, —$(CH_2)_r$—$C_{3-7}$ carbocycle substituted with 0–3 $R^{4b}$, or —$(CH_2)_r$-5–6 membered heterocycle consisting of: carbon atoms and 1–4 heteroatoms selected from the group consisting of N, O, and $S(O)_p$, and substituted with 0–3 $R^{4b}$. In other embodiments, the present invention includes compounds of Formula (I) where $R^4$ is H, —$(CH_2)_r$—C(O)$NR^{7a}R^8$, $C_{1-4}$ haloalkyl, $C_{1-4}$ alkyl, $C_{2-4}$ alkenyl, $C_{2-4}$ alkynyl, —$(CH_2)_r$—$C_{3-6}$ cycloalkyl, phenyl or benzyl. In other embodiments, the present invention includes compounds of Formula (I) where $R^4$ is H, Me, Et, Pr, phenyl, cyclopropylmethyl, 3-pyridylmethyl, —$CH_2CONR^{7a}R^8$, or benzyl.

In some embodiments according to the first aspect, the present invention includes compounds of Formula (I) where $R^5$ is H, F, $C_{1-4}$ haloalkyl, $C_{1-4}$ alkyl substituted with 0–1 $R^{5a}$, $C_{2-4}$ alkenyl substituted with 0–1 $R^{5a}$, $C_{2-4}$ alkynyl substituted with 0–1 $R^{5a}$, —$(CH_2)_r$—$C_{3-7}$ cycloalkyl substituted with 0–2 $R^{5b}$, or —$(CH_2)_r$-phenyl substituted with 0–2 $R^{5b}$. In other embodiments, the present invention includes compounds of Formula (I) where $R^5$ is H, F, $C_{1-4}$ haloalkyl, or $C_{1-4}$ alkyl substituted with 0–2 $R^{5a}$. In other embodiments, the present invention includes compounds of Formula (I) where $R^5$ is H, F, $C_{1-4}$ haloalkyl, or $C_{1-4}$ alkyl. In other embodiments, the present invention includes compounds of Formula (I) where $R^5$ is H or $C_{1-3}$ alkyl. In other embodiments, the present invention includes compounds of Formula (I) where $R^5$ is H, Me, Et, or Pr.

In some embodiments according to the first aspect, the present invention includes compounds of Formula (I) where $R^6$ is H or $C_{1-4}$ alkyl. In other embodiments, the present invention includes compounds of Formula (I) where $R^6$ is H, Me, Et, or Pr. In other embodiments, the present invention includes compounds of Formula (I) wherein $R^6$ is H.

In some embodiments according to the first aspect, the present invention includes compounds of Formula (I) where $R^{6a}$ is H, Me, Et, or Pr. In other embodiments, the present invention includes compounds of Formula (I) where $R^{6a}$ is H.

In some embodiments according to the first aspect, the present invention includes compounds of Formula (I) where $R^7$ is H, $C_{1-6}$ alkyl, —$(CH_2)_n$-phenyl, ($C_{1-6}$ alkyl)C(O)—, ($C_{6-10}$ aryl)—$CH_2$—C(O)—, ($C_{1-6}$ alkyl)—NHC(O)—, ($C_{6-10}$ aryl)—NHC(O)—, (5–10 membered heteroaryl)—NHC(O)—, (5–10 membered heteroaryl)—C(O)—, or ($C_{6-10}$ aryl)—($C_{1-4}$ alkyl)—C(O)—, wherein said phenyl, aryl and heteroaryl are substituted with 0–2 $R^f$. In other embodiments, the present invention includes compounds of Formula (I) where $R^7$ is H, $C_{1-6}$ alkyl, or —$(CH_2)_n$-phenyl. In other embodiments, the present invention includes compounds of Formula (I) where $R^7$ is H, $C_{1-4}$ alkyl, or benzyl. In other embodiments, the present invention includes compounds of Formula (I) where $R^7$ is H.

In some embodiments according to the first aspect, the present invention includes compounds of Formula (I) where $R^{7a}$ is H, $C_{1-6}$ alkyl substituted with 0–1 $R^{7b}$ or 0–1 $R^{7c}$, —(CH$_2$)$_r$—C$_{3-7}$ cycloalkyl substituted with 0–2 R$^f$, —(CH$_2$)$_r$-phenyl substituted with 0–3 R$^f$, or a —(CH$_2$)$_r$-5–6 membered heterocycle consisting of: carbon atoms and 1–4 heteroatoms selected from the group consisting of N, O, and S(O)$_p$, and substituted 0–3 R$^f$. In other embodiments, the present invention includes compounds of Formula (I) where R$^{7a}$ is H, C$_{1-6}$ alkyl, —(CH$_2$)$_2$N(Me)$_2$, —CH$_2$CO$_2$H, —(CH$_2$)$_2$CO$_2$H, —(CH$_2$)$_3$CO$_2$H, —(CH$_2$)$_3$OH, cyclopropylmethyl, cyclohexylmethyl, phenyl, benzyl, —CH(Me)phenyl, 4-methoxy-benzyl, 3,5-dimethoxy-benzyl, 4-chlorobenzyl, phenethyl, 3-chloro-phenethyl, phenylpropyl, (2-pyridyl)methyl, (3-pyridyl)methyl, (2-pyridyl)ethyl, (4-tetrahydropyranyl)methyl, 1-indanyl, or 1-naphthyl.

In some embodiments according to the first aspect, the present invention includes compounds of Formula (I) where R$^{7a}$ and R$^8$ are taken together with the nitrogen to which they are attached to form a 5–7 membered hetercyclic ring consisting of N,O and S(O)$_p$ optionally substituted with R$^{7a}$. In other embodiments, the present invention includes compounds of Formula (I) where R$^{7a}$ and R$^8$ together with the nitrogen to which they are attached form a morpholine or piperazine ring.

In some embodiments according to the first aspect, the present invention includes compounds of Formula (I) where R$^8$ is H, C$_{1-6}$ alkyl, or benzyl. In other embodiments, the present invention includes compounds of Formula (I) where R$^8$ is H or C$_{1-4}$ alkyl. In other embodiments, the present invention includes compounds of Formula (I) where R$^8$ is H.

In some embodiments according to the first aspect, the present invention includes compounds of Formula (I) where R$^{8a}$ is H, OH, benzyl, (C$_{1-6}$ alkyl)C(O)—, phenylC(O)—, (5–10 membered heteroaryl)—(C$_{0-4}$ alkyl)—C(O)—, (C$_{6-10}$ aryl)—(C$_{0-4}$ alkyl)—OC(O)—, C$_{1-4}$ alkoxy, (C$_{6-10}$ aryl)—(C$_{0-4}$ alkyl)—O—, or (C$_{6-10}$ aryl)—(C$_{0-4}$ alkyl)—C(O)—, wherein said phenyl, aryl and heteroaryl are substituted with 0–2 R$^f$. In other embodiments, the present invention includes compounds of Formula (I) where R$^{8a}$ is H, benzyl, OH, benzyloxy, OMe, —OC(O)Me, —C(O)OEt, —C(O)OMe, —C(O)Obenzyl, —COphenyl, (C$_{1-4}$ alkyl)OC(O)—, or (C$_{1-4}$ alkyl)C(O)—. In other embodiments, the present invention includes compounds of Formula (I) where R$^{8a}$ is H, OH or —C(O)OEt.

In some embodiments according to the first aspect, the present invention includes compounds of Formula (I) where R$^9$ is H, C$_{1-6}$ alkyl, or benzyl. In other embodiments, the present invention includes compounds of Formula (I) where R$^9$ is H or C$_{1-4}$ alkyl. In other embodiments, the present invention includes compounds of Formula (I) where R$^9$ is H.

In some embodiments according to the first aspect, the present invention includes compounds of Formula (I) where R$^{10}$ is H, C$_{1-6}$ alkyl substituted with 0–1 R$^{10a}$, C$_{2-6}$ alkenyl substituted with 0–1 R$^{10a}$, or C$_{2-6}$ alkynyl substituted with 0–1 R$^{10a}$. In other embodiments, the present invention includes compounds of Formula (I) where R$^{10}$ is H, C$_{1-6}$ alkyl, C$_{2-6}$ alkenyl, or C$_{2-6}$ alkynyl. In other embodiments, the present invention includes compounds of Formula (I) where R$^{10}$ is H or C$_{1-4}$ alkyl. In other embodiments, the present invention includes compounds of Formula (I) where R$^{10}$ is H.

In some embodiments according to the first aspect, the present invention includes compounds of Formula (I) where R$^{11}$ is H, —(CH$_2$)$_r$—OR$^a$, F, Cl, Br, CF$_3$, CN, NO$_2$, —(CH$_2$)$_r$—NR$^7$R$^8$, —(CH$_2$)$_r$—C(=NR$^8$)NR$^7$R$^9$, —C(O)R$^a$, —C(O)OR$^a$, —NR$^8$C(O)R$^c$, —NR$^8$C(O)OR$^c$, —C(O)NR$^{7a}$R$^8$, —NR$^8$C(O)NR$^8$R$^{10}$, —SO$_2$NR$^8$R$^{10}$, —NR$_8$SO$_2$—C$_{1-4}$ alkyl, —NR$^8$SO$_2$-phenyl, —S(O)$_2$CF$_3$, —S(O)$_p$—C$_{1-4}$ alkyl, —S(O)$_p$-phenyl, C$_{1-6}$ alkyl substituted with 0–1 R$^{11a}$, C$_{2-6}$ alkenyl substituted with 0–2 R$^{11a}$, C$_{2-6}$ alkynyl substituted with 0–1 R$^{11a}$, C$_{1-6}$ alkyl substituted with 0–1 R$^{11b}$, C$_{2-6}$ alkenyl substituted with 0–1 R$^{11b}$, or C$_{2-6}$ alkynyl substituted with 0–1 R$^{11b}$. In other embodiments, the present invention includes compounds of Formula (I) where R$^{11}$ is H, F, Cl, CF$_3$, C$_{1-6}$ alkyl, —(CH$_2$)$_r$—OR$^a$, CN, —(CH$_2$)$_r$—NR$^7$R$^8$, —(CH$_2$)$_r$—C(=NR$^8$)NR$^7$R$^9$, —C(O)R$^a$, —C(O)OR$^a$, —(CH$_2$)$_r$—NR$^8$C(O)R$^a$, —NR$^8$C(O)OR$^a$, —C(O)NR$^{7a}$R$^8$, —NR$^8$C(O)NR$^8$R$^9$, —SO$_2$NR$^8$R$^9$, or —NR$_8$SO$_2$—C$_{1-4}$ alkyl. In other embodiments, the present invention includes compounds of Formula (I) where R$^{11}$ is H, F, CF$_3$, C$_{1-4}$ alkyl, OH, —CH$_2$OH, OMe, OEt, CN, —NH$_2$, —CH$_2$NH$_2$, —CH$_2$NMe$_2$, —C(=NH)NH$_2$, —CH$_2$NHAc, —CO$_2$H, —CO$_2$Me, —NHAc, —NHCOEt, —NHCOPr, —NHC(O)(i-Bu), —NHCO(phenyl), —NHCO(benzyl), —NHCO(tetrazol-5-yl), —NHCOCH$_2$(tetrazol-5-yl), —NHCO(CH$_2$)$_2$(tetrazol-5-yl), —CO(1-morpholino), —CO [4-(2-OH-ethyl)-1-piperdinyl], —CO [4-(2-OMe-ethyl)-1-piperdinyl], —CO [4-(2-CO$_2$Et-ethyl)-1-piperdinyl], —C(O)NH$_2$, —C(O)NHMe, —C(O)NHEt, —C(O)NHPr, —C(O)NH(i-Bu), —C(O)NHisoamyl, —C(O)NH(CH$_2$CH$_2$N(Me)$_2$), —CONHCH$_2$CO$_2$H, —CONH(CH$_2$)$_2$CO$_2$H, —CONH(CH$_2$)$_3$CO$_2$H, —CONH(CH$_2$)$_3$OH, —CONHcyclopropylmethyl, —CONHcyclohexylmethyl, —CONHphenyl, —CONH(benzyl), —CONHCH(Me)phenyl, —CONH(4-OMe-benzyl), —CONH(3,5-diOMe-benzyl), —CONH(4-Cl-benzyl), —CONH(phenethyl), —CONH(3-Cl-phenethyl), —CONH(phenylpropyl), —CONH[(2-pyridyl)-methyl], —CONH[(3-pyridyl)-methyl], —CONH[2-(2-pyridyl)-ethyl], —CONHCH$_2$(4-tetrahydropyranyl), —CONHCH$_2$(1-indanyl), —CONH(1-naphthyl), —NHSO$_2$Me, or —NHSO$_2$Et.

In some embodiments according to the first aspect, the present invention includes compounds of Formula (I) where R$^{12}$ is OR$^{12a}$, —CH$_2$OR$^{12a}$, —C(O)NR$^{7a}$R$^8$, —(CH$_2$)$_r$CO$_2$R$^{12a}$, —(CH$_2$)$_r$SO$_3$H, —OSO$_3$H, —(CH$_2$)$_r$PO$_3$H, —OPO$_3$H$_2$, —PO$_3$H$_2$, —NHCOCF$_3$, —NHSO$_2$CF$_3$, —C(CF$_3$)$_2$OH, —SO$_2$NHR$^{12a}$, —SO$_2$NHCOR$^{12a}$, —SO$_2$NHCO$_2$R$^{12a}$, —CONHSO$_2$R$^{12b}$, —NHSO$_2$R$^{12b}$, or —(CH$_2$)$_r$-5-tetrazolyl. In other embodiments, the present invention includes compounds of Formula (Ia) where R$^{12}$ is OR$^{12a}$, —CH$_2$OR$^{12a}$, —C(O)NR$^{7a}$R$^8$, —(CH$_2$)$_r$CO$_2$R$^{12a}$, —SO$_2$NHR$^{12a}$, —SO$_2$NHCOR$^{12a}$, —SO$_2$NHCO$_2$R$^{12a}$, —CONHSO$_2$R$^{12b}$, —NHSO$_2$R$^{12b}$, or —(CH$_2$)$_r$-5-tetrazolyl. In other embodiments, the present invention includes compounds of Formula (I) where R$^{12}$ is OH, —CH$_2$OH, —CO$_2$R$^{12a}$, —CH$_2$CO$_2$R$^{12a}$, —SO$_2$NHR$^{12a}$, or —CONH$_2$. In other embodiments, the present invention includes compounds of Formula (I) where R$^{12}$ is —CO$_2$H, —CH$_2$CO$_2$H, —CO$_2$Me, —CH$_2$OH, —SO$_2$NH$_2$, or —CONH$_2$.

In a second aspect, the present invention includes compounds of Formula (Ia):

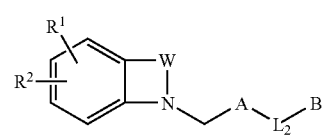

(Ia)

or a stereoisomer or pharmaceutically acceptable salts, hydrates, or prodrugs thereof, wherein:

W is —CH$_2$CH$_2$—, —CH$_2$CR$^4$R$^5$—, —CR$^4$R$^5$CH$_2$—, —CR$^4$=CH—, —CH$_2$CH$_2$CH$_2$—, or —CR$^4$R$^5$CH$_2$CH$_2$—;

L$_2$ is a bond, —(CR$^6$R$^{6a}$)$_{1-2}$—, —O—, —NR$^7$—, —C(O)—, —S(O)$_p$—, —(CR$^6$R$^{6a}$)C(O)—, —C(O)(CR$^6$R$^{6a}$)—, —(CR$^6$R$^{6a}$)O—, —O(CR$^6$R$^{6a}$)—, —(CR$^6$R$^{6a}$)NR$^7$—, —NR$^7$(CR$^6$R$^{6a}$)—, —(CR$^6$R$^{6a}$)S(O)$_p$—, —S(O)$_p$(CR$^6$R$^{6a}$)—, —C(O) O—, —OC(O)—, —C(O)NR$^8$—, —NR$^8$C(O)—, —S(O)NR$^8$—, —S(O)$_2$NR$^8$—, —NR$^8$S(O)—, or —NR$^8$S(O)$_2$—;

A is phenyl substituted with 0–2 R$^{11}$ and 0–1 R$^{12}$, or a 5–12 membered heterocycle consisting of: carbon atoms and 1–4 heteroatoms selected from the group consisting of N, O, and S(O)$_p$, and substituted 0–2 R$^{11}$ and 0–1 R$^{12}$;

B is phenyl substituted with 0–2 R$^{11}$ and 0–1 R$^{12}$, or a 5–12 membered heterocycle consisting of: carbon atoms and 1–4 heteroatoms selected from the group consisting of N, O, and S(O)$_p$, and substituted with 0–2 R$^{11}$ and 0–1 R$^{12}$;

R$^1$ is H, —NH$_2$, —NH(C$_{1-3}$ alkyl), —N(C$_{1-3}$ alkyl)$_2$, —C(=NH)NH$_2$, —NHC(=NH)NH$_2$, —C(O)NH$_2$, —CH$_2$NH$_2$, —CH$_2$NH(C$_{1-3}$ alkyl), —CH$_2$N(C$_{1-3}$ alkyl)$_2$, —CH$_2$CH$_2$NH$_2$, —CH$_2$CH$_2$NH(C$_{1-3}$ alkyl), —CH$_2$CH$_2$N(C$_{1-3}$ alkyl)$_2$, —C(=NR$^8$)NR$^7$R$^9$, —NHC(=NR$^8$)NR$^7$R$^9$, —ONHC(=NR$^8$)NR$^7$R$^9$, —NR$^8$CH(=NR$^7$), —C(=NR$^{8a}$)NR$^7$R$^9$, —NHC(=NR$^{8a}$)NR$^7$R$^9$, —ONHC(=NR$^{8a}$)NR$^7$R$^9$, —NHC(=NR$^{8a}$)NR$^7$R$^9$, —NR$^8$CH(=NR$^{8a}$), —NR$^7$R$^8$, —C(O)NR$^{7a}$R$^8$, —S(O)$_p$NR$^8$R$^9$, F, Cl, Br, I, OCF$_3$, CF$_3$, OR$^a$, SR$^a$, CN or C$_{1-6}$ alkyl substituted with 1 R$^{1a}$;

R$^{1a}$ is —C(=NR$^8$)NR$^7$R$^9$, —NHC(=NR$^8$)NR$^7$R$^9$, —ONHC(=NR$^8$)NR$^7$R$^9$, —NR$^8$CH(=NR$^7$), —C(=NR$^{8a}$)NR$^7$R$^9$, —NHC(=NR$^{8a}$)NR$^7$R$^9$, —ONHC(=NR$^{8a}$)NR$^7$R$^9$, —NR$^8$CH(=NR$^{8a}$), —NR$^7$R$^8$, —C(O)NR$^{7a}$R$^8$, —S(O)$_p$NR$^8$R$^9$, F, Cl, Br, I, OCF$_3$, CF$_3$, OR$^a$, SR$^a$, or CN;

R$^2$ is H, F, OR$^a$, CN, —NR$^7$R$^8$, —C(O)NR$^{7a}$R$^8$, —NR$^{10}$C(O)R$^b$, —S(O)$_p$NR$^8$R$^9$, —S(O)R$^c$, —S(O)$_2$R$^c$, C$_{1-6}$ alkyl substituted with 0–2 R$^{2a}$, —(CH$_2$)$_r$—C$_{3-7}$ carbocycle substituted with 0–2 R$^{2b}$, or —(CH$_2$)$_r$-5–7 membered heterocycle consisting of: carbon atoms and 1–4 heteroatoms selected from the group consisting of N, O, and S(O)$_p$, and substituted with 0–2 R$^{2b}$;

each R$^{2a}$ is, independently at each occurrence, H, F, OCF$_3$, CF$_3$, OR$^a$, SR$^a$, CN, —NR$^7$R$^8$, —C(O)NR$^{7a}$R$^8$, —S(O)$_p$NR$^8$R$^9$, —NR$^{10}$C(O)R$^b$, —S(O)$_p$NR$^8$R$^9$, —S(O)R$^c$, or —S(O)$_2$R$^c$;

each R$^{2b}$ is, independently at each occurrence, H, F, OR$^a$, SR$^a$, CN, NO$_2$, CF$_3$, —SO$_2$R$^c$, —NR$^7$R$^8$, C$_{1-6}$ alkyl, C$_{2-6}$ alkenyl, C$_{2-6}$ alkynyl, C$_{3-6}$ cycloalkyl, C$_{1-4}$ haloalkyl, C$_{1-4}$ haloalkyloxy-, C$_{1-4}$ alkyloxy-, C$_{1-4}$ alkylthio-, C$_{1-4}$ alkyl-C(O)—, or C$_{1-4}$ alkyl-C(O)NH—;

alternately, when R$^1$ and R$^2$ are substituted on adjacent ring carbon atoms, they can be taken together with the ring carbon atoms to which they are attached to form a 5–7 membered carbocycle or heterocycle substituted with 0–2 R$^{2b}$;

R$^4$ is H, F, C$_{1-4}$ haloalkyl, —(CH$_2$)$_r$—C(O)NR$^{7a}$R$^8$, C$_{1-6}$ alkyl substituted with 0–3 R$^{4a}$, C$_{2-6}$ alkenyl substituted with 0–3 R$^{4a}$, C$_{2-6}$ alkynyl substituted with 0–3 R$^{4a}$, —(CH$_2$)$_r$—C$_{3-8}$ carbocycle substituted with 0–3 R$^{4b}$, or —(CH$_2$)$_r$-5–6 membered heterocycle consisting of: carbon atoms and 1–4 heteroatoms selected from the group consisting of N, O, and S(O)$_p$, and substituted with 0–3 R$^{4b}$;

each R$^{4a}$ is, independently at each occurrence, H, C$_{1-4}$ alkyl, OR$^a$, F, =O, CF$_3$, CN, —C(O)R$^a$, —C(O)OR$^a$, —C(O)NR$^{7a}$R$^8$, —NR$^{10}$COR$^c$, or —S(O)$_p$R$^b$;

each R$^{4b}$ is, independently at each occurrence, H, OH, Cl, F, Cl, Br, CN, NO$_2$, CF$_3$, —C(O)OR$^a$, —SO$_2$R$^c$, —NR$^7$R$^8$, C$_{1-6}$ alkyl, C$_{2-6}$ alkenyl, C$_{2-6}$ alkynyl, C$_{3-6}$ cycloalkyl, C$_{1-4}$ haloalkyl, C$_{1-4}$ haloalkyloxy-, C$_{1-4}$ alkyloxy-, C$_{1-4}$ alkylthio-, C$_{1-4}$ alkyl-C(O)—, C$_{1-4}$ alkyl-C(O)NH—, —C(O)NR$^{7a}$R$^8$, —NR$^{10}$C(O)R$^c$, —NR$^{10}$S(O)$_2$NR$^8$R$^9$, or —S(O)$_2$R$^8$R$^9$;

each R$^5$ is, independently at each occurrence, H, F, C$_{1-4}$ haloalkyl, C$_{1-6}$ alkyl substituted with 0–2 R$^{5a}$, C$_{2-6}$ alkenyl substituted with 0–2 R$^{5a}$, C$_{2-6}$ alkynyl substituted with 0–2 R$^{5a}$, —(CH$_2$)$_r$—C$_{3-7}$ cycloalkyl substituted with 0–2 R$^{5b}$, —(CH$_2$)$_r$-phenyl substituted with 0–2 R$^{5b}$, or —(CH$_2$)$_r$-5–6 membered heterocycle consisting of: carbon atoms and 1–4 heteroatoms selected from the group consisting of N, O, and S(O)$_p$, and substituted with 0–2 R$^{5b}$;

each R$^{5a}$ is, independently at each occurrence, H, C$_{1-4}$ alkyl, OR$^a$, F, =O, CF$_3$, CN, —C(O)R$^a$, —C(O)OR$^a$, —C(O)NR$^{7a}$R$^8$, or —S(O)$_p$R$^c$;

each R$^{5b}$ is, independently at each occurrence, H, OH, Cl, F, Br, CN, NO$_2$, CF$_3$, —C(O)OR$^a$, —SO$_2$R$^c$, —NR$^7$R$^8$, C$_{1-6}$ alkyl, C$_{2-6}$ alkenyl, C$_{2-6}$ alkynyl, C$_{3-6}$ cycloalkyl, C$_{1-4}$ haloalkyl, C$_{1-4}$ haloalkyloxy-, C$_{1-4}$ alkyloxy-, C$_{1-4}$ alkylthio-, C$_{1-4}$ alkyl-C(O)—, or C$_{1-4}$ alkyl-C(O)NH—;

each R$^7$ is, independently at each occurrence, H, C$_{1-6}$ alkyl, —(CH$_2$)$_n$-phenyl, (C$_{1-6}$ alkyl)C(O)—, (C$_{6-10}$ aryl)—C$_{0-4}$ alkyl-C(O)—, (C$_{3-6}$ cycloalkyl)—C$_{0-4}$ alkyl-C(O)—, (5–10 membered heteroaryl)—C$_{0-4}$ alkyl-C(O)—, (C$_{1-4}$ alkyl)OC(O)—, (C$_{6-10}$ aryl)—C$_{1-4}$ alkyl-OC(O)—, (C$_{1-4}$ alkyl)—C(O)O—(C$_{1-4}$ alkyl)—OC(O)—, (C$_{6-10}$ aryl)—C(O)O—(C$_{1-4}$ alkyl)—OC(O)—, (5–10 membered heteroaryl)—CH$_2$—OC(O)—, (C$_{1-6}$ alkyl)—NHC(O)—, (C$_{6-10}$ aryl)—C$_{0-4}$ alkyl-NHC(O)—, (5–10 membered heteroaryl)—C$_{0-4}$ alkyl-NHC(O)—, (C$_{1-6}$ alkyl)—S(O)$_2$—, (C$_{6-10}$ aryl)—(C$_{0-4}$ alkyl)—S(O)$_2$—, (5–10 membered heteroaryl)—C$_{0-4}$ alkyl-S(O)$_2$—, (C$_{1-6}$ alkyl)$_2$NC(O)—, phenyl-NHC(O)—, benzyl-NHC(O)—, or (phenyl)(C$_{1-6}$ alkyl)NC(O)—, wherein said phenyl, aryl and heteroaryl are substituted with 0–2 R$^f$;

each R$^{7a}$ is, independently at each occurrence, H, C$_{1-4}$ alkyl substituted with 0–1 R$^{7b}$ or 0–1 R$^c$, C$_{3-7}$ cycloalkyl substituted with 0–2 R$^d$, phenyl substituted with 0–3 R$^f$, or a 5–6 membered heterocycle consisting of: carbon atoms and 1–4 heteroatoms selected from the group consisting of N, O, and S(O)$_p$, and substituted 0–3 R$^f$;

each R$^{7b}$ is, independently at each occurrence, =O, OR$^g$, F, Cl, Br, I, CN, NO$_2$, —NR$^7$R$^8$, —C(O)R$^g$, —C(O)OR$^g$, —NR$^8$C(O)R$^g$, —C(O)NR$^8$R$^9$, —NR$^8$C(O)NR$^8$R$^9$, —SO$_2$NR$^8$R$^9$, —NR$^8$SO$_2$NR$^8$R$^9$, —NR$^8$SO$_2$—C$_{1-4}$ alkyl, —NR$^8$SO$_2$CF$_3$, —NR$^8$SO$_2$-phenyl, —S(O)$_2$CF$_3$, —S(O)$_p$—C$_{1-4}$ alkyl, —S(O)$_p$-phenyl, or —(CF$_2$)$_r$CF$_3$;

each R$^{7c}$ is, independently at each occurrence, C$_{3-10}$ carbocycle substituted with 0–3 R$^f$; or a 5–12 membered heterocycle consisting of: carbon atoms and 1–4 heteroatoms selected from the group consisting of N, O, and S(O)$_p$, and substituted 0–3 R$^f$;

each R$^8$ is, independently at each occurrence, H, C$_{1-6}$ alkyl, or —(CH$_2$)$_n$-phenyl;

each R$^{8a}$ is, independently at each occurrence, H, OH, C$_{1-6}$ alkyl, —(CH$_2$)$_n$-phenyl, (C$_{1-6}$ alkyl)C(O)—, (C$_{6-10}$ aryl)—C$_{1-4}$ alkyl-C(O)—, (C$_{3-6}$ cycloalkyl)—C$_{0-4}$ alkyl-C(O)—, (5–10 membered heteroaryl)—C$_{0-4}$ alkyl-C(O)—, (C$_{1-4}$ alkyl)OC(O)—, (C$_{6-10}$ aryl)—C$_{0-4}$ alkyl-OC(O)—, (C$_{1-4}$ alkyl)—C(O)O—(C$_{1-4}$ alkyl)—OC(O)—, C$_{1-4}$ alkoxy, (C$_{6-10}$ aryl)—C$_{1-4}$ alkoxy, (C$_{1-4}$ alkyl)C(O)O—, or (C$_{6-10}$ aryl)—(C$_{0-4}$ alkyl)—C(O)O—; wherein said phenyl, aryl and heteroaryl are substituted with 0–2 R$^f$;

alternatively, R$^7$ and R$^8$, or R$^{7a}$ and R$^8$, when attached to the same nitrogen, combine to form a 5–10 membered heterocyclic ring consisting of carbon atoms and 0–2 additional heteroatoms selected from the group consisting of N, O, and S(O)$_p$;

each $R^9$ is, independently at each occurrence, H, $C_{1-6}$ alkyl, or —$(CH_2)_n$-phenyl;

each $R^{10}$ is, independently at each occurrence, H, $C_{1-6}$ alkyl substituted with 0–2 $R^{10a}$, $C_{2-6}$ alkenyl substituted with 0–2 $R^{10a}$, $C_{2-6}$ alkynyl substituted with 0–2 $R^{10a}$, ($C_{1-6}$ alkyl)C(O)—, ($C_{3-6}$ cycloalkyl)$C_{1-3}$ alkyl-C(O)—, ($C_{3-6}$ cycloalkyl)C(O)—, phenyl-C(O)—, benzyl-C(O)—, benzyl-S(O)$_2$—, ($C_{1-6}$ alkyl)NHC(O)—, ($C_{1-6}$ alkyl)$_2$NC(O)—, phenyl-NHC(O)—, benzyl-NHC(O)—, (phenyl)($C_{1-6}$ alkyl)NC(O)—, (benzyl)($C_{1-6}$ alkyl)NC(O)—, ($C_{1-6}$ alkyl)—S(O)$_2$—, phenyl-S(O)$_2$—, —$(CH_2)_r$—$C_{3-10}$ carbocycle substituted with 0–3 $R^d$, or —$(CH_2)_r$-5–10 membered heterocycle consisting of carbon atoms and 1–4 heteroatoms selected from the group consisting of N, O, and S(O)$_p$, and substituted with 0–3 $R^d$;

each $R^{10a}$ is, independently at each occurrence, H, $C_{1-4}$ alkyl, $OR^a$, Cl, F, Cl, Br, I, =O, $CF_3$, CN, $NO_2$, —C(O)$R^a$, —C(O)$OR^a$, —C(O)$NR^{7a}R^8$, or —S(O)$_pR^c$;

each $R^{11}$ is, independently at each occurrence, H, =O, —$(CH_2)_r$—$OR^a$, F, Cl, Br, I, $CF_3$, CN, $NO_2$, —$(CH_2)_r$—$NR^7R^8$, —$(CH_2)_r$—C(=$NR^8$) $NR^7R^9$, —C(O)$R^a$, —C(O)$OR^a$, —$(CH_2)_r$—$NR^8C(O)R^a$, —NHC(O)($CH_2)_rC(O)OR^a$, —$NR^8C(O)OR^c$, —C(O)$NR^{7a}R^8$, —$NR^8C(O)NR^8R^{10}$, —$SO_2NR^8R^{10}$, —$NR^8SO_2NR^8R^{10}$, —$NR^8SO_2$—$C_{1-4}$ alkyl, —$NR^8SO_2CF_3$, —$NR^8SO_2$-phenyl, —S(O)$_2CF_3$, —S(O)$_p$—$C_{1-4}$ alkyl, —S(O)$_p$-phenyl, —$(CF_2)_rCF_3$, $C_{1-6}$ alkyl substituted with 0–2 $R^{11a}$, $C_{2-6}$ alkenyl substituted with 0–2 $R^{11a}$, $C_{2-6}$ alkynyl substituted with 0–2 $R^{11a}$, $C_{1-6}$ alkyl substituted with 0–2 $R^{11b}$, $C_{2-6}$ alkenyl substituted with 0–2 $R^{11b}$, or $C_{2-6}$ alkynyl substituted with 0–2 $R^{11b}$;

each $R^{11a}$ is, independently at each occurrence, =O, $OR^a$, F, Cl, Br, I, CN, $NO_2$, —$NR^7R^8$, —C(O)$R^a$, —C(O)$OR^a$, —$NR^8C(O)R^a$, —C(O)$NR^{7a}R^8$, —$NR^8C(O)NR^8R^{10}$, —$SO_2NR^8R^{10}$, —$NR^8SO_2NR^8R^{10}$, —$NR^8SO_2$—$C_{1-4}$ alkyl, —$NR^8SO_2CF_3$, —$NR^8SO_2$-phenyl, —S(O)$_2CF_3$, —S(O)$_p$—$C_{1-4}$ alkyl, —S(O)$_p$-phenyl, or —$(CF_2)_rCF_3$;

each $R^{11b}$ is, independently at each occurrence, $C_{3-10}$ carbocycle substituted with 0–3 $R^d$, or a 5–12 membered heterocycle consisting of: carbon atoms and 1–4 heteroatoms selected from the group consisting of N, O, and S(O)$_p$, and substituted 0–3 $R^d$;

each $R^{12}$ is, independently at each occurrence, $OR^{12a}$, —$CH_2OR^{12a}$, —C(O)$NR^{7a}R^8$, —$(CH_2)_rCO_2R^{12a}$, —$(CH_2)_r$ $SO_3H$, —$OSO_3H$, —$(CH_2)_rPO_3H$, —$OPO_3H_2$, —$PO_3H_2$, —$NHCOCF_3$, —$NHSO_2CF_3$, —$CONHNHSO_2CF_3$, —C($CF_3)_2OH$, —$SO_2NHR^{12a}$, —$CONHSO_2NHR^{12a}$, —$SO_2NHCOR^{12a}$, —$SO_2NHCO_2R^{12a}$, —$CONHSO_2R^{12b}$, —$NHSO_2R^{12b}$, —$CONHOR^{12b}$,

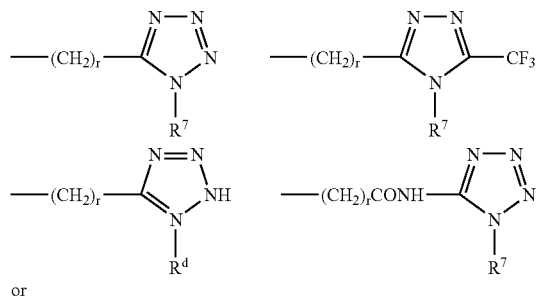

or

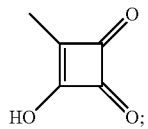

each $R^{12a}$ is, independently at each occurrence, H, $C_{1-6}$ alkyl, —$(CH_2)_r$—$C_{3-10}$ carbocycle substituted with 0–3 $R^d$, or —$(CH_2)_r$-5–10 membered heterocycle consisting of carbon atoms and 1–4 heteroatoms selected from the group consisting of N, O, and S(O)$_p$, and substituted with 0–3 $R^d$;

each $R^{12b}$ is, independently at each occurrence, $C_{1-6}$ alkyl substituted with 0–2 $R^{12c}$ $C_{2-6}$ alkenyl substituted with 0–2 $R^{12c}$ $C_{2-6}$ alkynyl substituted with 0–2 $R^{12c}$, —$(CH_2)_r$—$C_{3-10}$ carbocycle substituted with 0–3 $R^{12c}$, or —$(CH_2)_r$-5–10 membered heterocycle consisting of: carbon atoms and 1–4 heteroatoms selected from the group consisting of N, O, and S(O)$_p$, and substituted with 0–3 $R^{12c}$;

each $R^{12c}$ is, independently at each occurrence, H, F, Cl, Br, I, $CF_3$, $OCF_3$, CN, $NO_2$, $OR^a$, —$CO_2R^a$, —$NR^7R^8$, —$SO_2R^c$, $C_{1-6}$ alkyl, $C_{2-6}$ alkenyl, $C_{2-6}$ alkynyl, —$(CH_2)_r$—$C_{3-10}$ carbocycle substituted with 0–3 $R^d$, or —$(CH_2)_r$-5–10 membered heterocycle consisting of carbon atoms and 1–4 heteroatoms selected from the group consisting of N, O, and S(O)$_p$, and substituted with 0–3 $R^d$;

each $R^a$ is, independently at each occurrence, H, $C_{1-4}$ alkyl, —$(CH_2)_r$—$C_{3-7}$ cycloalkyl, —$(CH_2)_r$—$C_{6-10}$ aryl, or —$(CH_2)_r$-5–10 membered heteroaryl, wherein said aryl or heteroaryl groups are optionally substituted with 0–2 $R^f$;

each $R^b$ is, independently at each occurrence, $CF_3$, OH, $C_{1-4}$ alkoxy, $C_{1-6}$ alkyl, —$(CH_2)_r$—$C_{3-10}$ carbocycle substituted with 0–2 $R^d$, or —$(CH_2)_r$-5–10 membered heterocycle containing from 1–4 heteroatoms selected from the group consisting of N, O, and S(O)$_p$ and substituted with 0–2 $R^d$;

each $R^c$ is, independently at each occurrence, $C_{1-4}$ alkyl, $C_{6-10}$ aryl, 5–10 membered heteroaryl, ($C_{6-10}$ aryl)—$C_{1-4}$ alkyl, or (5–10 membered heteroaryl)—$C_{1-4}$ alkyl, wherein said aryl and heteroaryl groups are substituted with 0–2 $R^d$;

each $R^d$ is, independently at each occurrence, H, =O, $OR^a$, F, Cl, Br, I, CN, $NO_2$, —$NR^7R^8$, —C(O)$R^a$, —C(O)$OR^a$, —$NR^8C(O)R^a$, —C(O)$NR^{7a}R^8$, —$SO_2NR^8R^9$, —$NR^8SO_2NR^8R^9$, —$NR^8SO_2$—$C_{1-4}$ alkyl, —$NR^8SO_2CF_3$, —$NR^8SO_2$-phenyl, —S(O)$_2CF_3$, —S(O)$_p$—$C_{1-4}$ alkyl, —S(O)$_p$-phenyl, —$(CF_2)_rCF_3$, $C_{1-6}$ alkyl substituted with 0–2 $R^e$, $C_{2-6}$ alkenyl substituted with 0–2 $R^e$, or $C_{2-6}$ alkynyl substituted with 0–2 $R^e$;

each $R^e$ is, independently at each occurrence, =O, $OR^a$, F, Cl, Br, I, CN, $NO_2$, —$NR^8R^9$, —C(O)$R^a$, —C(O)$OR^a$, —$NR^8C(O)R^a$, —C(O)$NR^{7a}R^8$, —$SO_2NR^8R^9$, —$NR^8SO_2NR^8R^9$, —$NR^8SO_2$—$C_{1-4}$ alkyl, —$NR^8SO_2CF_3$, —$NR^8SO_2$-phenyl, —S(O)$_2CF_3$, —S(O)$_p$—$C_{1-4}$ alkyl, —S(O)$_p$-phenyl, or —$(CF_2)_rCF_3$;

each $R^f$ is, independently at each occurrence, H, =O, —$(CH_2)_r$—$OR^9$, F, Cl. Br, I, CN, $NO_2$, —$NR^8R^9$, —C(O)$R^g$, —C(O)$OR^9$, —$NR^8C(O)R^g$, —C(O) $NR^8R^9$, —$SO_2NR^8R^9$, —$NR^8SO_2NR^8R^9$, —$NR^8SO_2$—$C_{1-4}$ alkyl, —$NR^8SO_2CF_3$, —$NR^8SO_2$-phenyl, —S(O)$_2CF_3$, —S(O)$_p$—$C_{1-4}$ alkyl, —S(O)$_p$-phenyl, —$(CF_2)_rCF_3$, $C_{1-6}$ alkyl, $C_{2-6}$ alkenyl, or $C_{2-6}$ alkynyl;

each $R^g$ is, independently at each occurrence, H, $C_{1-6}$ alkyl, or —$(CH_2)_n$-phenyl;

n, at each occurrence, is selected from 0, 1, 2, 3, and 4;

p, at each occurrence, is selected from 0, 1, and 2; and r, at each occurrence, is selected from 0, 1, 2, 3, and 4.

In some embodiments according to the second aspect, the present invention includes compounds of Formula (Ia) W is —$CH_2CH_2$—, —CH=CH—, —$C(C_{1-4}$ alkyl)=CH—, —C(benzyl)=CH—, —CH=N—, —$C(C_{1-4}$ alkyl)=NH—, —C(benzyl)=N—, —$CH(benzyl)CH_2$—, —$C(Me)(phenyl)CH_2CH_2$—, or —$CH(phenyl)CH_2CH_2$—. In other embodiments, the present invention includes compounds of Formula (Ia) where W is —$CH_2CH_2$—, —CH=CH—, —$C(C_{1-4}$ alkyl)=NH—, or —C(benzyl)=CH—.

In some embodiments according to the second aspect, the present invention includes compounds of Formula (Ia) where $L_2$ is a bond, —$(CH_2)_{1-2}$—, —O—, —$NR^{10}$—, —C(O)—, —$S(O)_p$—, —$(CH_2)C(O)$—, —$C(O)(CH_2)$—, —$(CH_2)O$—, —$O(CH_2)$—, —$(CH_2)NR^{10}$—, —$NR^{10}(CH_2)$—, —$(CH_2)S(O)_p$—, —$S(O)_p(CH_2)$—, —C(O)O—, —OC(O)—, —$C(O)NR^8$—, —$NR^8C(O)$—, —$S(O)NR^8$—, —$S(O)_2NR^8$—, —$NR^8S(O)$—, or —$NR^8S(O)_2$—. In other embodiments, the present invention includes compounds of Formula (Ia) where $L_2$ is a bond, —$(CH_2)_{1-2}$—, —O—, —$NR^7$—, —C(O)—, —$S(O)_p$—, —$(CH_2)C(O)$—, —$C(O)(CH_2)$—, —$(CH_2)O$—, —$O(CH_2)$—, —$(CH_2)NR^7$—, —$NR^7(CH_2)$—, —$C(O)NR^8$—, —$NR^8C(O)$—, —$S(O)_2NR^8$—, or —$NR^8S(O)_2$—. In other embodiments, the present invention includes compounds of Formula (Ia) where $L_2$ is a bond, —$(CH_2)_{1-2}$—, —O—, —$NR^7$—, —$(CH_2)O$—, —$O(CH_2)$—, —$(CH_2)NR^7$—, —$NR^7(CH_2)$—, —CONH—, or —NHCO—. In other embodiments, the present invention includes compounds of Formula (Ia) where $L_2$ is a bond, —$CH_2$—, —O—, —CONH—, —NHCO—, —$(CH_2)O$—, or —$O(CH_2)$—.

In some embodiments according to the second aspect, the present invention includes compounds of Formula (Ia) where A is phenyl substituted with 0–2 $R^{11}$, or pyridyl substituted with 0–2 $R^{11}$. In other embodiments, the present invention includes compounds of Formula (Ia) where A is 1,2-phenylene, 3-carboxy-1,2-phenylene, 4-methyl-1,2-phenylene, 4-methoxy-1,2-phenylene, 4-aminomethyl-1,2-phenylene, 4-amidino-1,2-phenylene, 4-amidinomethyl-1,2-phenylene, 4-acetoamidomethyl-1,2-phenylene, 5-(N,N-dimethylaminoethylcarbamoyl)-1,2-phenylene, 5-carboxy-1,2-phenylene, 5-hydroxymethyl-1,2-phenylene, 5-acetylamino-1,2-phenylene, 5-propionylamino-1,2-phenylene, 5-butyrylamino-1,2-phenylene, 5-(3-methylbutyrylamino)-1,2-phenylene, 5-(2,2-dimethylpropionylamino)-1,2-phenylene, 5-benzylcarbonylamino-1,2-phenylene, 4-methoxy-5-hydroxy-1,2-phenylene, 5-carbamoyl-1,2-phenylene, 5-methylcarbamoyl-1,2-phenylene, 5-ethylcarbamoyl-1,2-phenylene, 5-propylcarbamoyl-1,2-phenylene, 5-isopropylcarbamoyl-1,2-phenylene, 5-isobutylcarbamoyl-1,2-phenylene, 5-t-butylcarbamoyl-1,2-phenylene, 5-isoamylcarbamoyl-1,2-phenylene, 5-carboxymethylcarbamoyl-1,2-phenylene, 5-(2-carboxyethyl)carbamoyl-1,2-phenylene, 5-(3-hydroxypropyl)carbamoyl-1,2-phenylene, 5-(3-carboxypropyl)carbamoyl-1,2-phenylene, 5-(cyclopropylmethyl)carbamoyl-1,2-phenylene, 5-(cyclohexylmethyl)carbamoyl-1,2-phenylene, 5-phenylcarbamoyl-1,2-phenylene, 5-benzylcarbamoyl-1,2-phenylene, 5-(1-phenylethyl)carbamoyl-1,2-phenylene, 5-phenethylcarbamoyl-1,2-phenylene, 5-(3-phenylpropyl-carbamoyl)-1,2-phenylene, 5-(4-methoxybenzyl)carbamoyl-1,2-phenylene, 5-(3,5,dimethoxybenzyl)carbamoyl-1,2-phenylene, 5-(4-chlorobenzyl)carbamoyl-1,2-phenylene, 5-[2-(3-chloropheny)ethyl]carbamoyl-1,2-phenylene, 5-(2-pyridylmethyl)carbamoyl-1,2-phenylene, 5-(3-pyridylmethyl)carbamoyl-1,2-phenylene, 5-[2-(2-pyridyl)ethyl]carbamoyl-1,2-phenylene, 5-(4-tetrahydropyranyl)methylcarbamoyl-1,2-phenylene, 5-(morpholine-4-carbonyl)-1,2-phenylene, 5-[4-(2-hydroxyethyl)-piperdine-1-carbonyl]-1,2-phenylene, 5-[4-(2-methoxyethyl)-piperdine-1-carbonyl]-1,2-phenylene, 5-[4-(ethoxycarbonylmethyl)-piperdine-1-carbonyl]-1,2-phenylene, 5-(1-naphthyl)carbamoyl-1,2-phenylene, 5-(1-indanyl)carbamoyl-1,2-phenylene, 1,3-phenylene, 5-amino-1,3-phenylene, 5-acetylamino-1,3-phenylene, 5-propionylamino-1,3-phenylene, 5-butyrylamino-1,3-phenylene, 5-(3-methylbutyrylamino)-1,2-phenylene, 5-(2,2-dimethylpropionylamino)-1,2-phenylene, or 6-amino-2,3-pyridylene; wherein the attachment to $L_2$ is at carbon 1 of said phenylene rings.

In some embodiments according to the second aspect, the present invention includes compounds of Formula (Ia) where B is phenyl substituted with 0–1 $R^{11}$ and $R^{12}$. In other embodiments, the present invention includes compounds of Formula (Ia) where B is 2-carboxy-phenyl, 2-aminosulfonyl-phenyl, 3-carboxymethyl-phenyl, 2,4-dicarboxy-phenyl, 2,4-dimethoxycarbonyl-phenyl, 2,4-dicarbamoyl-phenyl, 2-carboxy-4-methoxycarbonyl-phenyl, 2-carboxy-4-methyl-phenyl, 2-carboxy-4-methoxy-phenyl, 2-carboxy-4-ethoxy-phenyl, 2-carboxy-4-flouro-phenyl, 2-carboxy-4-amino-phenyl, 2-carboxy-4-cyano-phenyl, 2-carboxy-4-acetylamino-phenyl, 2-carboxy-4-carbamoyl-phenyl, 2,5-dicarboxy-phenyl, 2,5-dicarboxy-4-methoxy-phenyl, 2-carboxy-4,5-dimethoxy-phenyl, 2-carboxy-4-triflouromethyl-phenyl, 5-carboxy-4-methoxy-phenyl, 3-carboxy-4-pyridyl, or 2-carboxy-6-methoxy-3-pyridyl.

In some embodiments according to the second aspect, the present invention includes compounds of Formula (Ia) where $R^1$ is H, F, Cl, —$NH_2$, —$NH(C_{1-3}$ alkyl), —$N(C_{1-3}$ alkyl)$_2$, —C(=NH)$NH_2$, —NHC(=NH)$NH_2$, —C(O)$NH_2$, —$CH_2NH_2$, —$CH_2NH(C_{1-3}$ alkyl), —$CH_2N(C_{1-3}$ alkyl)$_2$, —$C(=NR^8)$ $NR^7R^9$, —NHC(=$NR^8$)$NR^7R^9$, —$NR^8$CH(=$NR^7$), —C(=$NR^{8a}$)$NR^7R^9$, —NHC(=$NR^{8a}$)$NR^7R^9$, —$NR^7R^8$, —C(O)$NR^{7a}R^8$, —$S(O)_pNR^8R^9$, $OR^a$, or CN. In other embodiments, the present invention includes compounds of Formula (Ia) where $R^1$ is H, F, Cl, —$NH_2$, —C(=NH)$NH_2$, —C(=O)$NH_2$, —$CH_2NH_2$, —C(O)$NR^{7a}R^8$, OMe, or CN. In other embodiments, the present invention includes compounds of Formula (Ia) where $R^1$ is H, F, —$NH_2$, —C(=NH)$NH_2$, —C(=O)$NH_2$, —$CH_2NH_2$, Cl, or OMe.

In some embodiments according to the second aspect, the present invention includes compounds of Formula (Ia) where $R^2$ is H, F, $OR^a$, CN, —$NR^7R^8$, —C(O)$NR^{7a}R^8$, —$NR^{10}C(O)R^b$, —$S(O)_pNR^8R^9$, or $C_{1-6}$ alkyl substituted with 0–1 $R^{2a}$. In other embodiments, the present invention includes compounds of Formula (Ia) where $R^2$ is H, F, OMe, OEt, CN, —$NH_2$, —C(O)$NH_2$, or $C_{1-6}$ alkyl.

In some embodiments according to the second aspect, the present invention includes compounds of Formula (Ia) where $R^4$ is H, $C_{1-4}$ haloalkyl, —$(CH_2)_r$—C(O)$NR^{7a}R^8$, $C_{1-6}$ alkyl substituted with 0–2 $R^{4a}$, $C_{2-6}$ alkenyl substituted with 0–2 $R^{4a}$, $C_{2-6}$ alkynyl substituted with 0–2 $R^{4a}$, —$(CH_2)_r$—$C_{3-8}$ carbocycle substituted with 0–3 $R^{4b}$, or —$(CH_2)_r$-5–6 membered heterocycle consisting of: carbon atoms and 1–4 heteroatoms selected from the group consisting of N, O, and $S(O)_p$, and substituted with 0–3 $R^{4b}$. In other embodiments, the present invention includes compounds of Formula (Ia) where $R^4$ is H, $C_{1-4}$ haloalkyl, —$(CH_2)_r$—C(O)$NR^{7a}R^8$, $C_{1-4}$ alkyl substituted with 0–2 $R^{4a}$, $C_{2-4}$ alkenyl substituted with 0–2 $R^{4a}$, $C_{2-4}$ alkynyl substituted with 0–2 $R^{4a}$, —$(CH_2)_r$—$C_{3-7}$ carbocycle substituted with 0–3 $R^{4b}$, or —$(CH_2)_r$-5–6 membered heterocycle consisting of: carbon atoms and 1–4 heteroatoms selected from the group consisting of N, O, and $S(O)_p$, and substituted with 0–3 $R^{4b}$. In other embodiments, the present invention includes compounds of Formula (Ia) where $R^4$ is H, $-(CH_2)_r-C(O)NR^{7a}R^8$, $C_{1-4}$ haloalkyl, $C_{1-4}$ alkyl, $C_{2-4}$ alkenyl, $C_{2-4}$ alkynyl, $-(CH_2)_r-C_{3-6}$ cycloalkyl, phenyl or benzyl. In other embodiments, the present invention includes compounds of Formula (Ia) where $R^4$ is H, Me, Et, Pr, phenyl, cyclopropylmethyl, 3-pyridylmethyl, $-CH_2CONR^{7a}R^8$, $C_{3-6}$ cycloalkyl, or benzyl.

In some embodiments according to the second aspect, the present invention includes compounds of Formula (Ia) where $R^5$ is H, F, $C_{1-4}$ haloalkyl, or $C_{1-4}$ alkyl. In other embodiments, the present invention includes compounds of Formula (Ia) where $R^5$ is H or $C_{1-3}$ alkyl. In other embodiments, the present invention includes compounds of Formula (Ia) where $R^5$ is H, Me, Et, or Pr.

In some embodiments according to the second aspect, the present invention includes compounds of Formula (Ia) where $R^6$ is H or $C_{1-4}$ alkyl. In other embodiments, the present invention includes compounds of Formula (Ia) where $R^6$ is H, Me, Et, or Pr. In other embodiments, the present invention includes compounds of Formula (Ia) wherein $R^6$ is H.

In some embodiments according to the second aspect, the present invention includes compounds of Formula (Ia) where $R^{6a}$ is H, Me, Et, or Pr. In other embodiments, the present invention includes compounds of Formula (Ia) where $R^{6a}$ is H.

In some embodiments according to the second aspect, the present invention includes compounds of Formula (Ia) where $R^7$ is H, $C_{1-6}$ alkyl, $(C_{1-6}$ alkyl$)C(O)-$, $-(CH_2)_n$-phenyl, $(C_{6-10}$ aryl$)-CH_2-C(O)-$, $(C_{1-6}$ alkyl$)-NHC(O)-$, $(C_{6-10}$ aryl$)-NHC(O)-$, (5–10 membered heteroaryl)$-NHC(O)-$, (5–10 membered heteroaryl)$-C(O)-$, or $(C_{6-10}$ aryl$)-(C_{1-4}$ alkyl$)-C(O)-$, wherein said phenyl, aryl and heteroaryl are substituted with 0–2 $R^f$. In other embodiments, the present invention includes compounds of Formula (Ia) where $R^7$ is H, $C_{1-6}$ alkyl, or $-(CH_2)_n$-phenyl. In other embodiments, the present invention includes compounds of Formula (Ia) where $R^7$ is H, $C_{1-4}$ alkyl, or benzyl. In other embodiments, the present invention includes compounds of Formula (Ia) where $R^7$ is H.

In some embodiments according to the second, the present invention includes compounds of Formula (Ia) where $R^{7a}$ is H, $C_{1-6}$ alkyl substituted with 0–1 $R^{7b}$ or 0–1 $R^{7c}$, $-(CH_2)_r-C_{3-7}$ cycloalkyl substituted with 0–2 $R^f$, $-(CH_2)_r$-phenyl substituted with 0–3 $R^f$, or a $-(CH_2)_r$-5–6 membered heterocycle consisting of: carbon atoms and 1–4 heteroatoms selected from the group consisting of N, O, and $S(O)_p$, and substituted 0–3 $R^f$. In other embodiments, the present invention includes compounds of Formula (Ia) where $R^{7a}$ is H, $C_{1-6}$ alkyl, $-(CH_2)_2N(Me)_2$, $-CH_2CO_2H$, $-(CH_2)_2CO_2H$, $-(CH_2)_3CO_2H$, $-(CH_2)_3OH$, cyclopropylmethyl, cyclohexylmethyl, phenyl, benzyl, $-CH(Me)$phenyl, 4-methoxy-benzyl, 3,5-dimethoxy-benzyl, 4-chlorobenzyl, phenethyl, 3-chloro-phenethyl, phenylpropyl, (2-pyridyl)methyl, (3-pyridyl)methyl, (2-pyridyl)ethyl, (4-tetrahydropyranyl)methyl, 1-indanyl, or 1-naphthyl.

In some embodiments according to the first aspect, the present invention includes compounds of Formula (Ia) where $R^{7a}$ and $R^8$ are taken together with the nitrogen to which they are attached to form a 5–7 membered hetercyclic ring consisting of N,O and $S(O)_p$ optionally substituted with $R^{7a}$. In other embodiments, the present invention includes compounds of Formula (Ia) where $R^{7a}$ and $R^8$ together with the nitrogen to which they are attached form a morpholine or piperazine ring.

In some embodiments according to the second aspect the present invention includes compounds of Formula (Ia) where $R^8$ is H, $C_{1-6}$ alkyl, or benzyl. In other embodiments, the present invention includes compounds of Formula (Ia) where $R^8$ is H or $C_{1-4}$ alkyl. In other embodiments, the present invention includes compounds of Formula (Ia) where $R^8$ is H.

In some embodiments according to the first aspect, the present invention includes compounds of Formula (I) where $R^{8a}$ is H, OH, benzyl, $(C_{1-6}$ alkyl$)C(O)-$, phenyl$C(O)-$, (5–10 membered heteroaryl)$-(C_{0-4}$ alkyl$)-C(O)-$, $(C_{6-10}$ aryl$)-(C_{0-4}$ alkyl$)-OC(O)-$, $C_{1-4}$ alkoxy, $(C_{6-10}$ aryl$)-(C_{0-4}$ alkyl$)-O-$, or $(C_{6-10}$ aryl$)-(C_{0-4}$ alkyl$)-C(O)-$, wherein said phenyl, aryl and heteroaryl are substituted with 0–2 $R^f$. In other embodiments, the present invention includes compounds of Formula (I) where $R^{8a}$ is H, benzyl, OH, benzyloxy, OMe, $-OC(O)Me$, $-C(O)OEt$, $-C(O)OMe$, $-C(O)Obenzyl$, $-COphenyl$, $(C_{1-4}$ alkyl$)OC(O)-$, or $(C_{1-4}$ alkyl$)C(O)-$. In other embodiments, the present invention includes compounds of Formula (I) where $R^{8a}$ is H, OH or $-C(O)OEt$.

In some embodiments according to the second aspect, the present invention includes compounds of Formula (Ia) where $R^9$ is H, $C_{1-6}$ alkyl, or benzyl. In other embodiments, the present invention includes compounds of Formula (Ia) where $R^9$ is H or $C_{1-4}$ alkyl. In other embodiments, the present invention includes compounds of Formula (Ia) where $R^9$ is H.

In some embodiments according to the second aspect, the present invention includes compounds of Formula (Ia) where $R^{10}$ is H, $C_{1-6}$ alkyl substituted with 0–1 $R^{10a}$, $C_{2-6}$ alkenyl substituted with 0–1 $R^{10a}$, $C_{2-6}$ alkynyl substituted with 0–1 $R^{10a}$, $(C_{1-6}$ alkyl$)C(O)-$, phenyl-$C(O)-$, benzyl-$C(O)-$, benzyl-$S(O)_2-$, $(C_{1-6}$ alkyl$)-S(O)_2-$, or phenyl-$S(O)_2-$. In other embodiments, the present invention includes compounds of Formula (Ia) where $R^{10}$ is H, $C_{1-6}$ alkyl, $C_{2-6}$ alkenyl, $C_{2-6}$ alkynyl, $(C_{1-6}$ alkyl$)C(O)-$, benzyl-$C(O)-$, benzyl-$S(O)_2-$, or $(C_{1-6}$ alkyl$)-S(O)_2-$. In other embodiments, the present invention includes compounds of Formula (Ia) where $R^{10}$ is H or $C_{1-6}$ alkyl, $(C_{1-6}$ alkyl$)C(O)-$, benzyl-$C(O)-$, benzyl-$S(O)_2-$, or $(C_{1-6}$ alkyl$)-S(O)_2-$. In other embodiments, the present invention includes compounds of Formula (Ia) where $R^{10}$ is H or $C_{1-4}$ alkyl. In other embodiments, the present invention includes compounds of Formula (Ia) where $R^{10}$ is H.

In some embodiments according to the second aspect, the present invention includes compounds of Formula (Ia) where $R^{11}$ is H, $-(CH_2)_r-OR^a$, F, Cl, Br, $CF_3$, CN, $NO_2$, $-(CH_2)_r-NR^7R^8$, $-(CH_2)_r-C(=NR^8)NR^7R^9$, $-C(O)R^a$, $-C(O)OR^a$, $-NR^8C(O)R^c$, $-NR^8C(O)OR^c$, $-C(O)NR^{7a}R^8$, $-NR^8C(O)NR^8R^{10}$, $-SO_2NR^8R^{10}$, $-NR_8SO_2-C_{1-4}$ alkyl, $-NR^8SO_2$-phenyl, $-S(O)_2CF_3$, $-S(O)_p-C_{1-4}$ alkyl, $-S(O)_p$-phenyl, $C_{1-6}$ alkyl substituted with 0–1 $R^{11a}$, $C_{2-6}$ alkenyl substituted with 0–2 $R^{11a}$, $C_{2-6}$ alkynyl substituted with 0–1 $R^{11a}$, $C_{1-6}$ alkyl substituted with 0–1 $R^{11b}$, $C_{2-6}$ alkenyl substituted with 0–1 $R^{11b}$, or $C_{2-6}$ alkynyl substituted with 0–1 $R^{11b}$. In other embodiments, the present invention includes compounds of Formula (Ia) where $R^{11}$ is H, $-(CH_2)_r-OR^a$, CN, $-(CH_2)_r-OH$, $-(CH_2)_r-NR^{7a}R^8$, $-C(O)OR^a$, $-NR^8C(O)R^a$, $-NR^8C(O)OR^a$, $-C(O)NR^7R^8$, $-NR^8C(O)NR^8R^9$, $-SO_2NR^8R^9$, or $-NR_8SO_2-C_{1-4}$ alkyl. In other embodiments, the present invention includes compounds of Formula (Ia) where $R^{11}$ is H, F, Cl, $CF_3$, $C_{1-6}$ alkyl, $-(CH_2)_r-OR^a$, CN, $-(CH_2)_r-NR^7R^8$, $-(CH_2)_r-C(=NR^8)NR^7R^9$, $-C(O)R^a$, $-C(O)OR^a$, $-(CH_2)_r-NR^8C(O)R^a$, $-NR^8C(O)OR^a$, $-C(O)NR^{7a}R^8$, $-NR^8C(O)NR^8R^9$, $-SO_2NR^8R^9$, or —NR$^8$SO$_2$—C$_{1-4}$ alkyl. In other embodiments, the present invention includes compounds of Formula (Ia) where R$^{11}$ is H, F, CF$_3$, C$_{1-4}$ alkyl, OH, —CH$_2$OH, OMe, OEt, CN, —NH$_2$, —CH$_2$NH$_2$, —CH$_2$NMe$_2$, —C(=NH)NH$_2$, —CH$_2$NHAc, —CO$_2$H, —CO$_2$Me, —NHAc, —NHCOEt, —NHCOPr, —NHC(O)(i-Bu), —NHCO(phenyl), —NHCO(benzyl), —NHCO(tetrazol-5-yl), —NHCOCH$_2$ (tetrazol-5-yl), —NHCO(CH$_2$)$_2$(tetrazol-5-yl), —CO(1-morpholino), —CO [4-(2-OH-ethyl)-1-piperdinyl], —CO [4-(2-OMe-ethyl)-1-piperdinyl], —CO [4-(2-CO$_2$Et-ethyl)-1-piperdinyl], —C(O)NH$_2$, —C(O)NHMe, —C(O)NHEt, —C(O)NHPr, —C(O)NH(i-Bu), —C(O)NHisoamyl, —C(O)NH(CH$_2$CH$_2$N(Me)$_2$), —CONHCH$_2$CO$_2$H, —CONH(CH$_2$)$_2$CO$_2$H, —CONH(CH$_2$)$_3$CO$_2$H, —CONH (CH$_2$)$_3$OH, —CONHcyclopropylmethyl, —CONHcyclohexylmethyl, —CONHphenyl, —CONH(benzyl), —CONHCH(Me)phenyl, —CONH(4-OMe-benzyl), —CONH(3,5-diOMe-benzyl), —CONH(4-Cl-benzyl), —CONH (phenethyl), —CONH(3-Cl-phenethyl), —CONH (phenylpropyl), —CONH[(2-pyridyl)-methyl], —CONH [(3-pyridyl)-methyl], —CONH[2-(2-pyridyl)-ethyl], —CONHCH$_2$(4-tetrahydropyranyl), —CONHCH$_2$(1-indanyl), —CONH(1-naphthyl), —NHSO$_2$Me, or —NHSO$_2$Et.

In some embodiments according to the second aspect, the present invention includes compounds of Formula (Ia) where R$^{12}$ is OR$^{12a}$, —CH$_2$OR$^{12a}$, —C(O)NR$^{7a}$R$^8$, —(CH$_2$)$_r$CO$_2$R$^{12a}$, —(CH$_2$)$_r$SO$_3$H, —OSO$_3$H, —(CH$_2$)$_r$PO$_3$H, —OPO$_3$H$_2$, —PO$_3$H$_2$, —NHCOCF$_3$, —NHSO$_2$CF$_3$, —C(CF$_3$)$_2$OH, —SO$_2$NHR$^{12a}$, —SO$_2$NHCOR$^{12a}$, —SO$_2$NHCO$_2$R$^{12a}$, —CONHSO$_2$R$^{12b}$, —NHSO$_2$R$^{12b}$, or —(CH$_2$)$_r$-5-tetrazolyl. In other embodiments, the present invention includes compounds of Formula (Ia) where R$^{12}$ is OR$^{12a}$, —CH$_2$OR$^{12a}$, —C(O)NR$^{7a}$R$^8$, —(CH$_2$)$_r$CO$_2$R$^{12a}$, —SO$_2$NHR$^{12a}$, —SO$_2$NHCOR$^{12a}$, —SO$_2$NHCO$_2$R$^{12a}$, —CONHSO$_2$R$^{12b}$, —NHSO$_2$R$^{12b}$, or —(CH$_2$)$_r$-5-tetrazolyl. In other embodiments, the present invention includes compounds of Formula (Ia) where R$^{12}$ is OH, —CH$_2$OH, —CO$_2$R$^{12a}$, —CH$_2$CO$_2$R$^{12a}$, —SO$_2$NHR$^{12a}$, or —CONH$_2$. In other embodiments, the present invention includes compounds of Formula (Ia) where R$^{12}$ is —CO$_2$H, OH, —CH$_2$ (CO$_2$H), —CO$_2$Me, —CH$_2$OH, —SO$_2$NH$_2$, or —CONH$_2$.

In a third aspect, the present invention includes compounds of Formula (Ib):

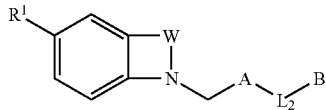

(Ib)

or a stereoisomer or pharmaceutically acceptable salts, hydrates, or prodrugs thereof, wherein:

W is —CH$_2$CH$_2$—, —CH=CH—, —C(benzyl)=CH—, —C(C$_{1-4}$ alkyl)=CH—, —CH=N—, —C(C$_{1-4}$ alkyl)=NH—, —C(benzyl)=N—, —CH(benzyl)CH$_2$—, —CH (phenyl)CH$_2$CH$_2$—, —C(Me)(phenyl)CH$_2$CH$_2$—, —C(3,5-diMe-benzyl)=CH—, —C(CH$_2$OH)=CH, —C(CONHMe)=CH—, —C(CONHPh)=CH—, —C(4-CO$_2$H-benzyl)=CH—, or —C(CH$_2$CONHMe)=CH—;

L$_2$ is a bond, —(CH$_2$)$_{1-2}$—, —O—, —NH—, —(CH$_2$) O—, —O(CH$_2$)—, —(CH$_2$)N —NH(CH$_2$)—, —CONH—, or —NHCO—;

A is phenyl substituted with 0–2 R$^{11}$, or pyridyl substituted with 0–2 R$^{11}$;

B is phenyl substituted with 0–2 R$^{11}$ and 0–1 R$^{12}$, or pyridyl substituted with 0–2 R$^{11}$ and 0–1 R$^{12}$;

R$^1$ is —C(=NH)NH$_2$, —C(=O)NH$_2$, —CH$_2$NH$_2$, —C(O)NR$^{7a}$R$^8$, OMe, Cl, H, F, NH$_2$ or CN;

each R$^7$ is, independently at each occurrence, H, C$_{1-6}$ alkyl, or benzyl;

each R$^{7a}$ is, independently at each occurrence, H, C$_{1-4}$ alkyl substituted with 0–1 R$^{7b}$ or 0–1 R$^c$, C$_{3-7}$ cycloalkyl substituted with 0–2 R$^d$, phenyl substituted with 0–3 R$^f$, or a 5–6 membered heterocycle consisting of: carbon atoms and 1–4 heteroatoms selected from the group consisting of N, O, and S(O)$_p$, and substituted 0–3 R$^f$;

each R$^{7b}$ is, independently at each occurrence, =O, OR$^9$, F, Cl, Br, I, CN, NO$_2$, —NR$^7$R$^8$, —C(O)R$^g$, —C(O)OR$^g$, —NR$^8$C(O)R$^g$, —C(O)NR$^8$R$^9$, —NR$^8$C(O)NR$^8$R$^9$, —SO$_2$NR$^8$R$^9$, —NR$^8$SO$_2$NR$^8$R$^9$, —NR$^8$SO$_2$—C 4 alkyl, —NR$^8$SO$_2$CF$_3$, —NR$^8$SO$_2$-phenyl, —S(O)$_2$CF$_3$, —S(O)$_p$—C$_{1-4}$ alkyl, —S(O)$_p$-phenyl, or —(CF$_2$)$_r$CF$_3$;

each R$^{7c}$ is, independently at each occurrence, C$_{3-10}$ carbocycle substituted with 0–3 R$^f$; or a 5–12 membered heterocycle consisting of: carbon atoms and 1–4 heteroatoms selected from the group consisting of N, O, and S(O)$_p$, and substituted 0–3 R$^f$;

each R$^8$ is, independently at each occurrence, H, C$_{1-6}$ alkyl, or benzyl;

each R$^9$ is, independently at each occurrence, H, C$_{1-6}$ alkyl, or benzyl;

each R$^{11}$ is, independently at each occurrence, H, F, Cl, CF$_3$, C$_{1-6}$ alkyl, —(CH$_2$)$_r$—OR$^a$, CN, —(CH$_2$)$_r$—NR$^7$R$^8$, —(CH$_2$)$_r$—C (=NR$^8$)NR$^7$R$^9$, —C(O)R$^a$, —C(O)OR$^a$, —(CH$_2$)$_r$—NR$^8$C(O)R$^a$, —NR$^8$C(O)OR$^c$, —C(O)NR$^{7a}$R$^8$, —NR$^8$C(O)NR$^8$R$^{10}$, —SO$_2$NR$^8$R$^{10}$, —NR$^8$SO$_2$NR$^8$R$^{10}$, or —NR$^8$SO$_2$—C$_{1-4}$ alkyl;

R$^{12}$ is —C(O)NR$^{7a}$R$^8$, —(CH$_2$)$_r$CO$_2$R$^{12a}$, —CH$_2$OR$^{12a}$, —SO$_2$NHR$^{12a}$, —SO$_2$NHCOR$^{12a}$, —SO$_2$NHCO$_2$R$^{12a}$, —CONHSO$_2$R$^{12b}$, —NHSO$_2$R$^{12b}$, or —(CH$_2$)$_r$-5-tetrazolyl;

each R$^{12a}$ is, independently at each occurrence, H or C$_{1-6}$ alkyl;

each R$^{12b}$ is, independently at each occurrence, C$_{1-4}$ alkyl substituted with 0–1 R$^{12c}$, C$_{2-4}$ alkenyl substituted with 0–1 R$^{12c}$, C$_{2-4}$ alkynyl substituted with 0–1 R$^{12c}$, —(CH$_2$)$_r$—C$_{3-7}$ carbocycle substituted with 0–2 R$^{12c}$, or —(CH$_2$)$_r$-5–6 membered heterocycle consisting of: carbon atoms and 1–4 heteroatoms selected from the group consisting of N, O, and S(O)$_p$, and substituted with 0–2 R$^{12c}$;

each R$^{12c}$ is, independently at each occurrence, H, F, Cl, Br, I, CF$_3$, OCF$_3$, CN, NO$_2$, OR$^a$, —CO$_2$R$^a$, —NR$^7$R$^8$, —SO$_2$R$^c$, C$_{1-6}$ alkyl, C$_{2-6}$ alkenyl, C$_{2-6}$ alkynyl, —(CH$_2$)$_r$—C$_{3-10}$ carbocycle substituted with 0–3 R$^d$; or —(CH$_2$)$_r$-5–10 membered heterocycle consisting of carbon atoms and 1–4 heteroatoms selected from the group consisting of N, O, and S(O)$_p$, and substituted with 0–3 R$^d$;

each R$^a$ is, independently at each occurrence, H, C$_{1-4}$ alkyl, —(CH$_2$)$_r$—C$_{3-7}$ cycloalkyl, —(CH$_2$)$_r$—C$_{6-10}$ aryl, or —(CH$_2$)$_r$-5–10 membered heteroaryl, wherein said aryl or heteroaryl groups are optionally substituted with 0–2 R$^f$;

each R$^c$ is, independently at each occurrence, C$_{1-4}$ alkyl, phenyl or benzyl;

each R$^f$ is, independently at each occurrence, H, =O, —(CH$_2$)$_r$—OR$^g$, F, Cl, Br, CF$_3$, CN, NO$_2$, —NR$^8$R$^9$, —C(O)R$^g$, —C(O)OR$^9$, —NR$^8$C(O)R$^g$, —C(O)NR$^8$R$^9$, —SO$_2$NR$^8$R$^9$, —NR$^8$SO$_2$—C$_{1-4}$ alkyl, —NR$^8$SO$_2$CF$_3$, —S(O)$_2$CF$_3$, —S(O)$_p$—C$_{1-4}$ alkyl, C$_1$–C$_6$ alkyl, C$_2$–C$_6$ alkenyl, or C$_2$–C$_6$ alkynyl;

each R$^g$ is, independently at each occurrence, H or C$_{1-4}$ alkyl;

p, at each occurrence, is selected from 0, 1, and 2; and
r, at each occurrence, is selected from 0, 1, 2, 3, and 4.

In a fourth aspect, the present invention includes compounds of Formula (Ib) or a stereoisomer or pharmaceutically acceptable salts, hydrates, or prodrugs thereof, wherein:

W is —CH$_2$CH$_2$—, —CH=CH—, —C(benzyl)=CH—, —C(C$_{1-4}$ alkyl)=CH—, —CH=N—, —CH(benzyl)CH$_2$—, —CH(phenyl)CH$_2$CH$_2$—, —C(Me)(phenyl)CH$_2$CH$_2$—, —C(3,5-diMe-benzyl)=CH—, —C(CH$_2$OH)=CH, —C(CONHMe)=CH—, —C(CONHPh)=CH—, —C(4-CO$_2$H-benzyl)=CH—, or —C(CH$_2$CONHMe)=CH—;

L$_2$ is a bond, —CH$_2$—, —O—, —CONH—, —NHCO—, —(CH$_2$)O—, or —OCH$_2$—;

A is phenyl substituted with 0–2 R$^{11}$, or pyridyl substituted with 0–2 R$^{11}$;

B is phenyl substituted with 0–2 R$^{11}$ and 0–1 R$^{12}$, or pyridyl substituted with 0–2 R$^{11}$ and 0–1 R$^{12}$;

R$^1$ is —C(=NH)NH$_2$, —C(=O)NH$_2$, —CH$_2$NH$_2$, H, F, Cl, or OMe;

each R$^{11}$ is, independently at each occurrence, H, F, CF$_3$, C$_{1-4}$ alkyl, OH, —CH$_2$OH, OMe, OEt, CN, —NH$_2$, —CH$_2$NH$_2$, —CH$_2$NMe$_2$, —C(=NH)NH$_2$, —CH$_2$C(=NH)NH$_2$, —CH$_2$NHAc, —CO$_2$H, —CO$_2$Me, —NHAc, —NHCOEt, —NHCOPr, —NHCO(i-Pr), —NHC(O)(i-Bu), —NHCO(phenyl), —NHCO(benzyl), —NHCO(tetrazol-5-yl), —NHCOCH$_2$(tetrazol-5-yl), —NHCO(CH$_2$)$_2$(tetrazol-5-yl), —CO(1-morpholino), —CO [4-(2-OH-ethyl)-1-piperdinyl], —CO [4-(2-OMe-ethyl)-1-piperdinyl], —CO [4-(2-CO$_2$Et-ethyl)-1-piperdinyl], —C(O)NH$_2$, —C(O)NHMe, —C(O)NHEt, —C(O)NHPr, —C(O)NH(i-Bu), —C(O)NHisoamyl, —C(O)NH(CH$_2$CH$_2$N(Me)$_2$), —CONHCH$_2$CO$_2$H, —CONH(CH$_2$)$_2$CO$_2$H, —CONH(CH$_2$)$_3$CO$_2$H, —CONH(CH$_2$)$_3$OH, —CONHcyclopropylmethyl, —CONHcyclohexylmethyl, —CONHphenyl, —CONH(benzyl), —CONHCH(Me)phenyl, —CONH(4-OMe-benzyl), —CONH(3,5-diOMe-benzyl), —CONH(4-Cl-benzyl), —CONH(phenethyl), —CONH(3-Cl-phenethyl), —CONH(phenylpropyl), —CONH[(2-pyridyl)-methyl], —CONH[(3-pyridyl)-methyl], —CONH[2-(2-pyridyl)-ethyl], —CONHCH$_2$(4-tetrahydropyranyl), —CONHCH$_2$(1-indanyl), —CONH(1-naphthyl), —NHSO$_2$Me, or —NHSO$_2$Et; and R$^{12}$ is OH, —CH$_2$OH, —CO$_2$H, —CH$_2$(CO$_2$H), —CO$_2$Me, —SO$_2$NH$_2$, or —CONH$_2$.

In a fifth aspect, the present invention includes compounds of Formula (Ib) or a stereoisomer or pharmaceutically acceptable salt or hydrate form thereof, wherein:

W is —CH$_2$CH$_2$—, —CH=CH—, —C(benzyl)=CH—, —CH(benzyl)CH$_2$—, or —C(C$_{1-4}$ alkyl)=CH—;

L$_2$ is a bond, —CONH—, —NHCO—, —(CH$_2$)O—, or —OCH$_2$—;

A is 1,2-phenylene, 3-carboxy-1,2-phenylene, 4-methyl-1,2-phenylene, 4-methoxy-1,2-phenylene, 4-aminomethyl-1,2-phenylene, 4-amidino-1,2-phenylene, 4-amidinomethyl-1,2-phenylene, 4-acetoamidomethyl-1,2-phenylene, 5-(N,N-dimethylaminoethylcarbamoyl)-1,2-phenylene, 5-carboxy-1,2-phenylene, 5-hydroxymethyl-1,2-phenylene, 5-acetylamino-1,2-phenylene, 5-propionylamino-1,2-phenylene, 5-butyrylamino-1,2-phenylene, 5-(3-methylbutyrylamino)-1,2-phenylene, 5-(2,2-dimethylpropionylamino)-1,2-phenylene, 5-benzylcarbonylamino-1,2-phenylene, 4-methoxy-5-hydroxy-1,2-phenylene, 5-carbamoyl-1,2-phenylene, 5-methylcarbamoyl-1,2-phenylene, 5-ethylcarbamoyl-1,2-phenylene, 5-propylcarbamoyl-1,2-phenylene, 5-isopropylcarbamoyl-1,2-phenylene, 5-isobutylcarbamoyl-1,2-phenylene, 5-t-butylcarbamoyl-1,2-phenylene, 5-isoamylcarbamoyl-1,2-phenylene, 5-carboxymethylcarbamoyl-1,2-phenylene, 5-(2-carboxyethyl)carbamoyl-1,2-phenylene, 5-(3-hydroxypropyl)carbamoyl-1,2-phenylene, 5-(3-carboxypropyl)carbamoyl-1,2-phenylene, 5-cyclopropylmethylcarbamoyl-1,2-phenylene, 5-cyclohexylmethylcarbamoyl-1,2-phenylene, 5-phenylcarbamoyl-1,2-phenylene, 5-benzylcarbamoyl-1,2-phenylene, 5-(1-phenylethyl)carbamoyl-1,2-phenylene, 5-phenethylcarbamoyl-1,2-phenylene, 5-(3-phenylpropylcarbamoyl)-1,2-phenylene, 5-(4-methoxybenzyl)carbamoyl-1,2-phenylene, 5-(3,5-dimethoxybenzyl)carbamoyl-1,2-phenylene, 5-(4-chlorobenzyl)carbamoyl-1,2-phenylene, 5-[2-(3-chloropheny)ethyl] carbamoyl-1,2-phenylene, 5-(2-pyridylmethyl)carbamoyl-1,2-phenylene, 5-(3-pyridylmethyl)carbamoyl-1,2-phenylene, 5-[2-(2-pyridyl)ethyl]carbamoyl-1,2-phenylene, 5-(4-tetrahydropyranyl)methylcarbamoyl-1,2-phenylene, 5-(morpholine-4-carbonyl)-1,2-phenylene, 5-[4-(2-hydroxyethyl)-piperdine-1-carbonyl]-1,2-phenylene, 5-[4-(2-methoxyethyl)-piperdine-1-carbonyl]-1,2-phenylene, 5-[4-(ethoxycarbonylmethyl)-piperdine-1-carbonyl]-1,2-phenylene, 5-(1-naphthyl)carbamoyl-1,2-phenylene, 5-(1-indanyl)carbamoyl-1,2-phenylene, 1,3-phenylene, 5-amino-1,3-phenylene, 5-acetylamino-1,3-phenylene, 5-propionylamino-1,3-phenylene, 5-butyrylamino-1,3-phenylene, 5-(3-methylbutyrylamino)-1,2-phenylene, 5-(2,2-dimethylpropionylamino)-1,2-phenylene, or 6-amino-2,3-pyridylene; wherein the attachment to L$_2$ is at carbon 1 of said phenylene rings;

B is 2-carboxy-phenyl, 2-aminosulfonyl-phenyl, 3-carboxymethyl-phenyl, 2,4-dicarboxy-phenyl, 2,4-dimethoxycarbonyl-phenyl, 2,4-dicarbamoyl-phenyl, 2-carboxy-4-methoxycarbonyl-phenyl, 2-carboxy-4-methyl-phenyl, 2-carboxy-4-methoxy-phenyl, 2-carboxy-4-ethoxy-phenyl, 2-carboxy-4-flouro-phenyl, 2-carboxy-4-amino-phenyl, 2-carboxy-4-cyano-phenyl, 2-carboxy-4-acetylamino-phenyl, 2-carboxy-4-carbamoyl-phenyl, 2,5-dicarboxy-phenyl, 2,5-dicarboxy-4-methoxy-phenyl, 2-carboxy-4,5-dimethoxy-phenyl, 2-carboxy-4-triflouromethyl-phenyl, 5-carboxy-4-methoxy-phenyl, 3-carboxy-4-pyridyl, or 2-carboxy-6-methoxy-3-pyridyl; and R$^1$ is —C(=NH)NH$_2$, —C(=O)NH$_2$, —NH$_2$, —CH$_2$NH$_2$, F, H, Cl, or OMe.

In a sixth aspect, the present invention provides a compound selected from Examples 1–115 or a stereoisomer or pharmaceutically acceptable salts, hydrates, or prodrugs thereof.

In another embodiment, the present invention provides a novel pharmaceutical composition, comprising: a pharmaceutically acceptable carrier and a therapeutically effective amount of a compound of the present invention or a stereoisomer or a pharmaceutically acceptable salt, hydrate or prodrug form thereof.

In another embodiment the present invention provides a method for modulation of the coagulation cascade and/or contact activation system comprising administering to a patient in need of such treatment a therapeutically effective amount of at least one of the compounds of the present invention or a pharmaceutically acceptable salt, hydrate or prodrug form thereof.

In another embodiment, the present invention provides a novel method for treating thromboembolic disorders comprising: administering to a patient in need of such treatment a therapeutically effective amount of at least one of the compounds of the present invention or a pharmaceutically acceptable salt, hydrate or prodrug form thereof.

In another embodiment, the present invention provides a novel method, wherein the thromboembolic disorder is selected from the group consisting of arterial cardiovascular thromboembolic disorders, venous cardiovascular thromboembolic disorders, arterial cerebrovascular thromboembolic disorders, and venous cerebrovascular thromboembolic disorders.

In another embodiment, the present invention provides a novel method, wherein the thromboembolic disorder is selected unstable angina, first myocardial infarction, recurrent myocardial infarction, ischemic sudden death, transient ischemic attack, stroke, atherosclerosis, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, and (f) other procedures in which blood is exposed to an artificial surface that promotes thrombosis.

In another embodiment, the present invention provides a method for treating inflammatory disorders comprising: administering to a patient in need of such treatment a therapeutically effective amount of at least one of the compounds of the present invention or a pharmaceutically acceptable salt or prodrug form thereof.

In another embodiment, the present invention provides a method, wherein the inflammatory disorder is selected from the group consisting of sepsis, acute respiratory dystress syndrome, and systemic inflammatory response syndrome.

In another embodiment, the present invention provides a novel method of treating a patient in need of thromboembolic disorder treatment, comprising: administering a compound of the present invention or a pharmaceutically acceptable salt or hydrate form thereof in an amount effective to treat a thromboembolic disorder.

In another embodiment, the present invention provides a method of treating a patient in need of inflammatory disorder treatment, comprising: administering a compound of the present invention or a pharmaceutically acceptable salt form thereof in an amount effective to treat an inflammatory disorder.

In another embodiment, the present invention provides a pharmaceutical composition further comprising at least one additional herapeutic agent selected from one or more of potassium channel openers, calcium channel blockers, sodium hydrogen exchanger inhibitors, antiarrhythmic agents, antiatherosclerotic agents, anticoagulants, antithrombotic agents, prothrombolytic agents, fibrinogen antagonists, diuretics, antihypertensive agents, ATPase inhibitors, mineralocorticoid receptor antagonists, phospodiesterase inhibitors, antidiabetic agents, anti-inflammatory agents, antioxidants, angiogenesis modulators, antiosteoporosis agents, hormone replacement therapies, hormone receptor modulators, oral contraceptives, antiobesity agents, antidepressants, antianxiety agents, antipsychotic agents, antiproliferative agents, antitumor agents, antiulcer and gastroesophageal reflux disease agents, growth hormone agents and/or growth hormone secretagogues, thyroid mimetics, anti-infective agents, antiviral agents, antibacterial agents, antifungal agents, cholesterol/lipid lowering agents and lipid profile therapies, and agents that mimic ischemic preconditioning and/or myocardial stunning.

In a preferred embodiment, the present invention provides a pharmaceutical composition wherein the at least one additional therapeutic agent is an antihypertensive agent selected from ACE inhibitors, AT-1 receptor antagonists, ET receptor antagonists, dual ET/AII receptor antagonists, and vasopepsidase inhibitors, an antiarrythmic agent selected from IKur inhibitors, or an antithrombotic agent selected from anticoagulants selected from thrombin inhibitors, other factor XIa inhibitors, other plasma kallikrein inhibitors, factor VIIa inhibitors and factor Xa inhibitors, and antiplatelet agents selected from GPIIb/IIIa blockers, P2Y$_1$ and P2Y$_{12}$ antagonists, thromboxane receptor antagonists, and aspirin.

In a preferred embodiment, the present invention provides pharmaceutical composition, wherein the additional therapeutic agent(s) are an anti-platelet agent or a combination thereof.

In a preferred embodiment, the present invention provides a pharmaceutical composition, wherein the additional therapeutic agent is the anti-platelet agent clopidogrel.

In another embodiment, the present invention provides a novel article of manufacture, comprising:
  (a) a first container;
  (b) a pharmaceutical composition located within the first container, wherein the composition, comprises: a first therapeutic agent, comprising: a compound of the present invention or a pharmaceutically acceptable salt or hydrate form thereof; and
  (c) a package insert stating that the pharmaceutical composition can be used for the treatment of a thromboembolic and/or inflammatory disorder.

In another preferred embodiment, the present invention provides a novel article of manufacture, further comprising:
  (d) a second container; wherein components (a) and (b) are located within the second container and component (c) is located within or outside of the second container.

In another embodiment, the present invention provides a novel article of manufacture, comprising:
  (a) a first container;
  (b) a pharmaceutical composition located within the first container, wherein the composition, comprises: a first therapeutic agent, comprising: a compound of the present invention or a pharmaceutically acceptable salt or hydrate form thereof; and
  (c) a package insert stating that the pharmaceutical composition can be used in combination with a second therapeutic agent to treat a thromboembolic and/or inflammatory disorder.

In another preferred embodiment, the present invention provides a novel article of manufacture, further comprising:
  (d) a second container; wherein components (a) and (b) are located within the second container and component (c) is located within or outside of the second container.

In another embodiment, the present invention provides a novel method, comprising: administering a compound of the present invention or a pharmaceutically acceptable salt or hydrate form thereof in an amount effective to treat a thromboembolic and/or inflammatory disorder.

In another embodiment, the present invention provides a compound of the present invention or a pharmaceutically acceptable salt or hydrate form thereof, for use in therapy.

In another embodiment, the present invention also provides the use of a compound of the present invention or a pharmaceutically acceptable salt or hydrate form thereof, for the manufacture of a medicament for the treatment of a thromboembolic and/or inflammatory disorder.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional more preferred embodiments. It is also to be understood that each individual element of the preferred embodiments is its own independent preferred embodiment. Furthermore, any element of an embodiment is meant to be combined with any and all other elements from any embodiment to describe an additional embodiment.

Definitions

Compounds of this invention may have one or more asymmetric centers. Unless otherwise indicated, all chiral (enantiomeric and diastereomeric) and racemic forms of compounds of the present invention are included in the present invention. Many geometric isomers of olefins, C=N double bonds, and the like can also be present in the compounds, and all such stable isomers are contemplated in the present invention. Accordingly, the present compounds can be isolated in optically active or racemic forms. It is well known in the art how to prepare optically active forms, such as by resolution of racemic forms or by synthesis from optically active starting materials. All chiral, (enantiomeric and diastereomeric) and racemic forms and all geometric isomeric forms of a structure are intended, unless the specific stereochemistry or isomer form is specifically indicated. All tautomers of shown or described compounds are also considered to be part of the present invention.

Preferably, the molecular weight of compounds of the present invention is less than about 500, 550, 600, 650, 700, 750, or 800 grams per mole. Preferably, the molecular weight is less than about 800 grams per mole. More preferably, the molecular weight is less than about 750 grams per mole. Even more preferably, the molecular weight is less than about 700 grams per mole.

As used herein, the term "alkyl" or "alkylene" is intended to include both branched and straight-chain saturated aliphatic hydrocarbon groups having the specified number of carbon atoms. For example, "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_{1-6}$ alkyl" denotes alkyl having 1 to 6 carbon atoms. Alkyl groups can be unsubstituted or substituted so that one or more of its hydrogens are replaced by another chemical group. Example alkyl groups include, but are not limited to, methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like.

Alkenyl" or "alkenylene" is intended to include hydrocarbon chains of either straight or branched configuration and having one or more double carbon-carbon bonds that may occur in any stable point along the chain. For example, "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, 4-methyl-3-pentenyl, and the like.

"Alkynyl" or "alkynylene" is intended to include hydrocarbon chains of either straight or branched configuration and having one or more triple carbon-carbon bonds that may occur in any stable point along the chain. For example, "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, hexynyl and the like.

"Halo" or "halogen" includes fluoro, chloro, bromo, and iodo. "Haloalkyl" refers to branched and straight-chained, having one or more halogen substituents. Example haloalkyl groups include, but are not limited to, $CF_3$, $C_2F_5$, $CHF_2$, $CCl_3$, $CHCl_2$, $C_2C_5$, and the like.

The term "alkoxy" or "alkyloxy" refers to an —O-alkyl group. "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy, and the like. Similarly, "alkylthio" or "thioalkoxy" represents an alkyl group as defined above with the indicated number of carbon atoms attached through a sulphur bridge; for example methyl-S—, ethyl-S—, and the like.

"Haloalkoxy" or "haloalkyloxy" represents a haloalkyl group as defined above with the indicated number of carbon atoms attached through an oxygen bridge. For example, "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, pentafluorothoxy, and the like. Similarly, "haloalkylthio" or "thiohaloalkoxy" represents a haloalkyl group as defined above with the indicated number of carbon atoms attached through a sulphur bridge; for example trifluoromethyl-S—, pentafluoroethyl-S—, and the like.

The term "cycloalkyl" refers to cyclized alkyl groups, including mono-, bi- or poly-cyclic ring systems. $C_{3-7}$ cycloalkyl is intended to include $C_3$, $C_4$, $C_5$, $C_6$, and $C_7$ cycloalkyl groups. Example cycloalkyl groups include, but are not limited to, cyclopropyl, cyclobutyl, cyclopentyl, cyclohexyl, norbornyl, and the like.

As used herein, "carbocycle" or "carbocyclic residue" is intended to mean any stable 3, 4, 5, 6, or 7-membered monocyclic or bicyclic or 7, 8, 9, 10, 11, 12, or 13-membered bicyclic or tricyclic ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane, [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, phenyl, and indanyl. A bridged ring occurs when one or more carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

"Aryl" groups refer to monocyclic or polycyclic aromatic hydrocarbons, including, for example, phenyl, naphthyl, phenanthranyl, and the like. Aryl moieties are well known and described, for example, in *Hawley's Condensed Chemical Dictionary* (13 ed.), R. J. Lewis, ed., J. Wiley & Sons, Inc., New York (1997). Aryl groups can be substituted or unsubstituted.

As used herein, the term "heterocycle" or "heterocyclic group" is intended to mean a stable 5, 6, or 7-membered monocyclic or bicyclic or 7, 8, 9, 10, 11, 12, 13, or 14-membered bicyclic heterocyclic ring which is saturated, partially unsaturated or fully unsaturated, and which consists of carbon atoms and 1, 2, 3 or 4 heteroatoms independently selected from the group consisting of N, O and S; and including any bicyclic group in which any of the above-defined heterocyclic rings is fused to a benzene ring. The nitrogen and sulfur heteroatoms may optionally be oxidized (i.e., N→O and S(O)$_p$). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1.

Examples of heterocycles include, but are not limited to, acridinyl, azocinyl, benzimidazolyl, benzofuranyl, benzothiofuranyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

Preferred 5 to 10 membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxazolidinyl, tetrahydrofuranyl, thiadiazolyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Preferred 5 to 6 membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxazolidinyl, tetrahydrofuranyl, thiadiazolyl, thiadiazolyl, thiazolyl, triazinyl, and triazolyl. Also included are fused ring and spiro compounds containing, for example, the above heterocycles.

As used herein, the term "aromatic heterocyclic group" or "heteroaryl" is intended to mean a stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, benzodioxane, and the like. Heteroaryl groups can be substituted or unsubstituted. The nitrogen atom may be substituted or unsubstituted (i.e., N or NR wherein R is H or another substituent, if defined). The nitrogen and sulfur heteroatoms may optionally be oxidized (i.e., N→O and S(O)$_p$). It is to be noted that total number of S and O atoms in the aromatic heterocycle is not more than 1. Bridged rings are also included in the definition of heterocycle. A bridged ring occurs when one or more atoms (i.e., C, O, N, or S) link two non-adjacent carbon or nitrogen atoms. Preferred bridges include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The term "counterion" is used to represent a small, negatively charged species such as chloride, bromide, hydroxide, acetate, and sulfate.

As referred to herein, the term "substituted" means that one or more hydrogen atoms is replaced with a non-hydrogen group, provided that normal valencies are maintained and that the substitution results in a stable compound. When a substituent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring.

When any variable (e.g., $R^{2a}$, $R^{2b}$, etc.) occurs more than one time in any constituent or formula for a compound, its definition at each occurrence is independent of its definition at every other occurrence. Thus, for example, if a group is shown to be substituted with 0–3 $R^{2b}$, then said group may optionally be substituted with up to three $R^{2b}$ groups and $R^{2b}$ at each occurrence is selected independently from the definition of $R^{2b}$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "pharmaceutically acceptable salt" refers to acid or base salts of the compounds described herein. Examples of pharmaceutically acceptable salts include, but are not limited to, mineral or organic acid salts of basic residues such as amines; alkali or organic salts of acidic residues such as carboxylic acids; and the like. Pharmaceutically acceptable salts of the compounds of the invention can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418, the disclosure of which is hereby incorporated by reference in its entirety. Examples of pharmaceutically acceptable salts include, but are not limited to, mineral or organic acid salts of basic residues such as amines; alkali or organic salts of acidic residues such as carboxylic acids; and the like. Pharmaceutically acceptable salts include the conventional non-toxic salts or the quaternary ammonium salts of the parent compound formed, for example, from non-toxic inorganic or organic acids. Such conventional non-toxic salts include those derived from inorganic acids such as hydrochloric, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

"Prodrugs" refer to inactive compounds that can be converted upon absorption by a mammalian subject to an active compound of the present invention. Prodrugs of the compounds of the present invention can be prepared by modifying functional groups present in the compounds of the present invention in such a way that the modifications are cleaved in vivo to produce the parent compounds. Examples of prodrugs include, but are not limited to, acetate, formate and benzoate derivatives of alcohol and amine functional groups in the compounds of the present invention. Preparation of prodrugs is well known in the art and described in, for example, *Medicinal Chemistry: Principles and Practice,* ed. F. D. King, The Royal Society of Chemistry, Cambridge, UK, 1994, which is incorporated herein by reference in its entirety.

Radiolabelled compounds of the present invention, i.e., wherein one or more of the atoms described are replaced by a radioactive isotope of that atom (e.g., C replaced by $^{13}$C or by $^{14}$C; and isotopes of hydrogen include tritium and deuterium), are also provided herein. Such compounds have a variety of potential uses, e.g., as standards and reagents in determining the ability of a potential pharmaceutical to bind to target proteins or receptors, or for imaging compounds of this invention bound to biological receptors in vivo or in vitro.

"Stable compound" and "stable structure" are meant to indicate a compound that is sufficiently robust to survive isolation to a useful degree of purity from a reaction mixture, and formulation into an efficacious therapeutic agent. It is preferred that compounds of the present invention do not contain a N-halo, $S(O)_2H$, or $S(O)H$ group.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

"Therapeutically effective amount" is intended to include an amount of a compound of the present invention that is effective when administered alone or in combination to inhibit factor XIa and/or plasma kallikrein. "Therapeutically effective amount" is also intended to include an amount of the combination of compounds claimed that is effective to inhibit factor XIa and/or plasma kallikrein. The combination of compounds is preferably a synergistic combination. Synergy, as described, for example, by Chou and Talalay, *Adv. Enzyme Regul.* 1984, 22:27–55, occurs when the effect (in this case, inhibition of factor XIa and/or plasma kallikrein) of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, increased antithrombotic and/or anti-inflammatory effect, or some other beneficial effect of the combination compared with the individual components.

The present invention further includes compositions comprising one or more compounds of the present invention and a pharmaceutically acceptable carrier.

A "pharmaceutically acceptable carrier" refers to media generally accepted in the art for the delivery of biologically active agents to animals, in particular, mammals. Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences,* 17th ed., Mack Publishing Company, Easton, Pa., 1985, which is incorporated herein by reference in its entirety.

Synthesis

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art and alternate methods must then be used.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (*Protective Groups In Organic Synthesis*, Wiley-Interscience, 3$^{rd}$ Edition, 1999).

All references cited herein are hereby incorporated in their entirety herein by reference.

Representative indoline compounds of this invention can be prepared as shown in Scheme 1. An appropriately functionalized indoline, such as 1a, is reductively aminated with a suitably substituted aldehyde 1b in the presence of a reducing agent such as sodium triacetoxyborohydride in a solvent such as 1,2-dichloroethane or tetrahydrofuran to give substituted indoline 1c.

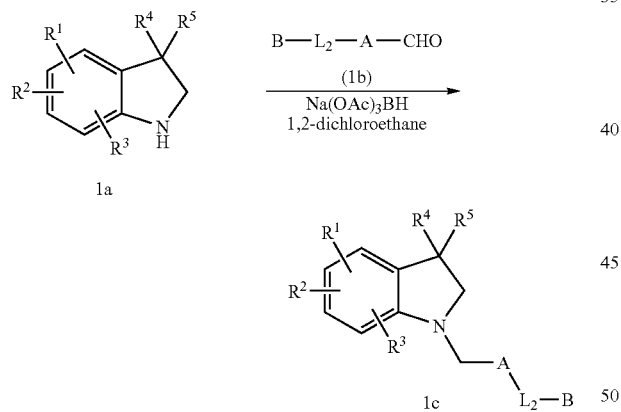

Further manipulation of the functional groups on both the indoline ring and the pendant group and deprotection as necessary, using methods known to one skilled in the art of organic synthesis, will give compounds of the invention. For example, as illustrated in Scheme 1a, treatment of a mixture of 5-cyanoindoline 1c and methyl 2-(2'-formylphenyl)benzoate 1d in 1,2-dichloroethane with sodium triacetoxyborohydride provides the N-alkylated indoline intermediate 1e. Conversion of the nitrile to the corresponding amidine can be carried out by a number of methods known in the literature, for example by Pinner reaction or alternately by conversion to an intermediate amidoxime which after treatment with acetic anhydride is reduced, either by catalytic hydrogenation or with zinc dust, to give the amidine 1f. Deprotection of the methyl ester provides acid 1g.

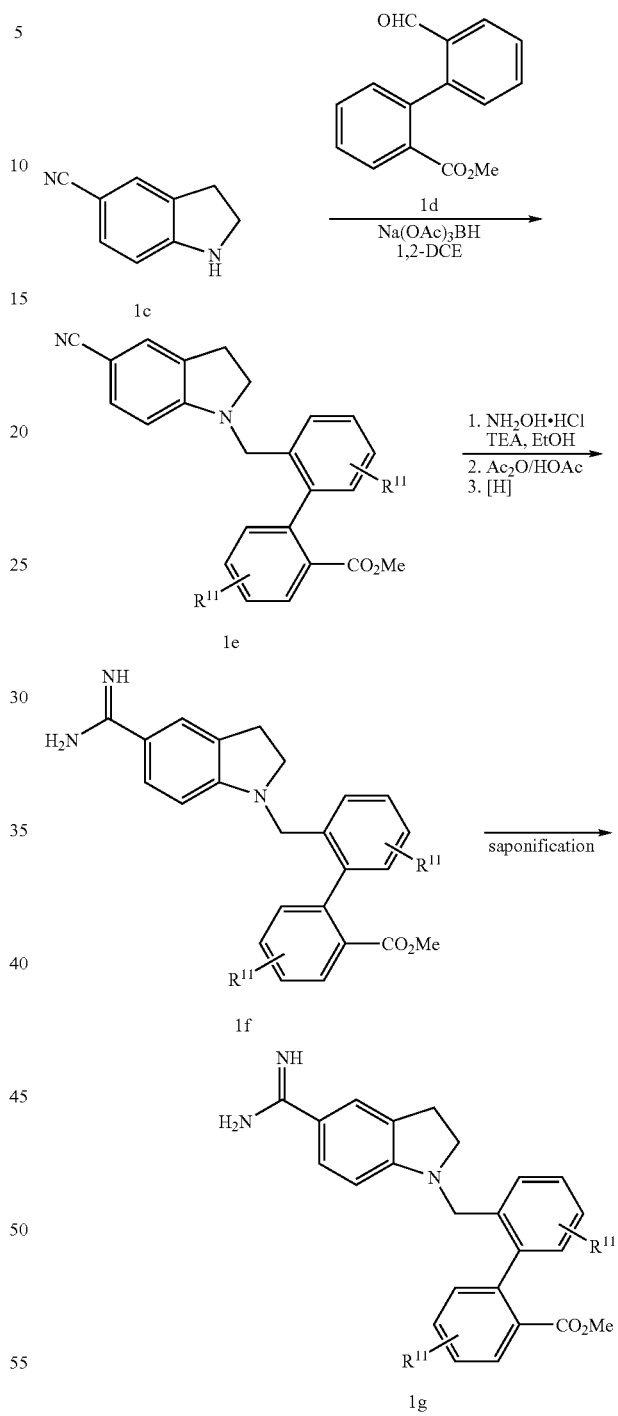

Alternately, the N-substituted indolines shown in Scheme 1a can be prepared by alkylation of indoline 2a with a suitably functionalized alkyl bromide, for example, 2b in the presence of a base such as sodium hydride in a suitable solvent such as DMF or DMA, as shown in Scheme 2 to provide compounds of formula 2c. This method can also be used to prepare the analogous indole compounds of formula 2d.

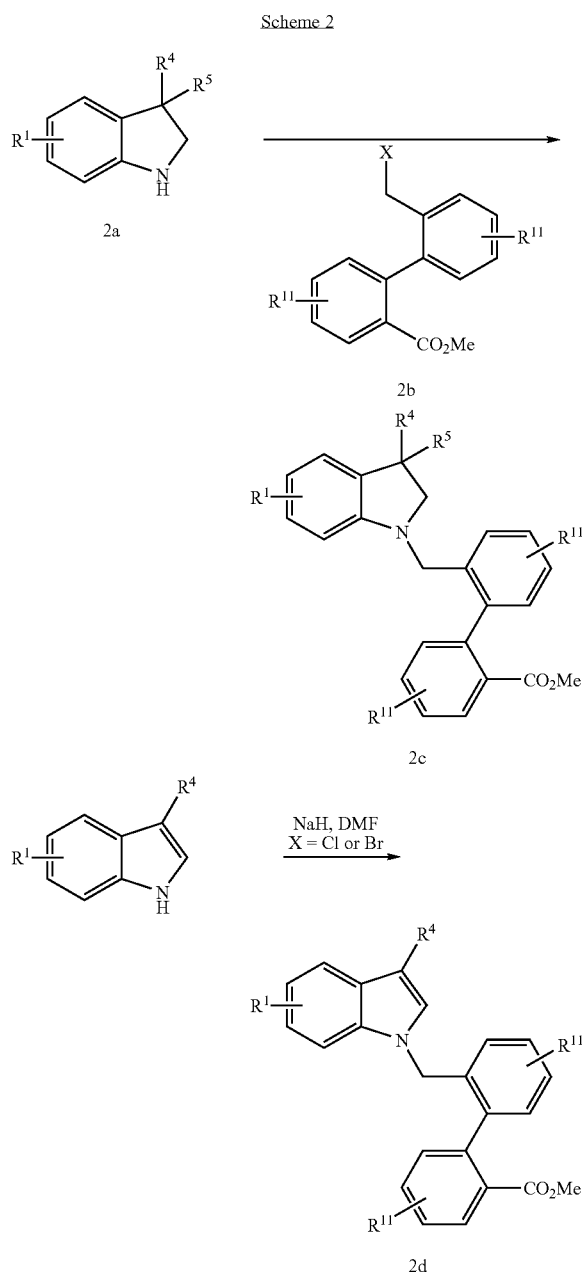

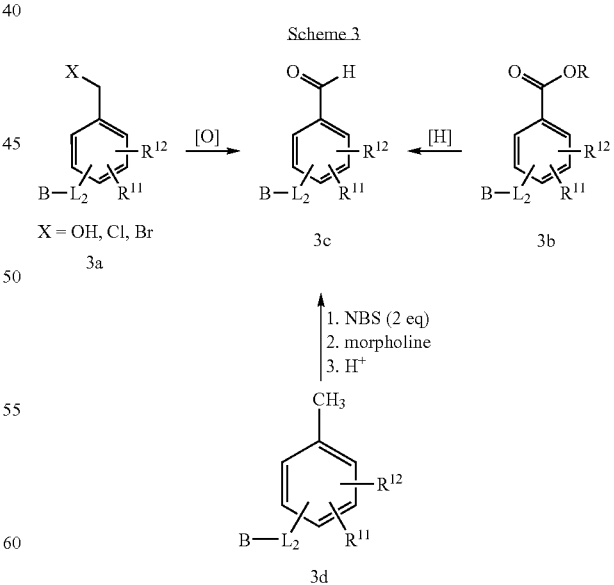

preparation of indole starting materials see: Hegedus, L. S., *Angew. Chem.* 1988, 100, 1147; Pindur, U. & Reinhard, A., *J. Heterocyclic Chem.* 1988, 25, 1; Clard, R. D. & Repke, D. B., *Heterocycles,* 1984, 22, 195; Ambekar, S. Y. *Curr. Sci.* 1983, 52, 578 and Zhu, X & Ganesan, A. *J. Org. Chem.,* 2002, 67, 2705). Methods for the synthesis of various substituted azaindoles are also known in the art and include but are not limited to the following: Rodriquez, A. L. et al. *Angew. Chemie Intl. Ed.* 2000, 39, 2488; Siu, J. et al. *Organic & Biomolecular Chem.* 2004, 2, 160; L'Heureux, A. et al. *Tet. Lett.* 2004, 45, 2317.

Alternate indoline starting materials suitable for use in the preparation of the above compounds of this invention can be prepared by condensation of appropriately substituted 2-iodoanilines with 1,3-dienes according to the method of Wang & Huang (*Tetrahedron Lett.* 1998, 39, 9605) or by reduction of 3,3-disubstituted indolones (for examples, see Kucerovy et al. *Synth. Commun.* 1992, 22, 729 or Takayama et al. *Tetrahedron Lett.* 1973, 365).

Suitable aldehydes useful for the synthesis of compounds in Scheme 1a are accessible from a variety of straightforward chemical transformations known to one skilled in the art. As outlined in Scheme 3, aldehydes 3c suitable for use in preparing compounds of this invention may be obtained through oxidation of the corresponding alcohols or halides 3a as taught in "Advanced Organic Chemistry" (Jerry March, Wiley Interscience pg 1057–60 and pg 1081 and references therein). Alternatively suitable aldehydes may be prepared by hydrogenation of the corresponding carboxylic acids 3b (Scheme 5, R=H) in the presence of palladium complexes and pivalic anhydride (Nagayama et al. *Chemistry Letters* 1998, 27, 1143–1144) or by reduction of an ester (R=alkyl) with DIBAL-H (Chandrasekhar et al. *Tetrahedron Letters* 1998, 39, 909–910). Additional aryl aldehydes may be obtained directly from the corresponding toluene derivatives 3d via oxidation or bromination of the methyl group.

Various indolines suitable for use in Schemes 1 and 2 above can be conveniently obtained by reduction of the corresponding indole analogs using a reducing agent such as sodium cyanoborohydride, sodium triacetoxyborohydride or triethylsilane in a suitable solvent such as dichloromethane or dichloroethane in the presence of an acid, such as acetic acid or trifluoroacetic acid. Suitably substituted indole compounds useful for the synthesis of the compounds of this invention are either commercially available or can be prepared according to established literature methods known to one skilled in the art. Methods for synthesis of a large variety of substituted indoles useful as starting materials for the preparation of indole and indoline compounds of the present invention are well known in the art and have been extensively reviewed. (For examples of methods useful for the Additional aldehydes of general Formulae (III), (IV) and (V) suitable for the synthesis of the compounds of the present invention may be prepared according to one or more of the methods described for the examples shown below.

(III)

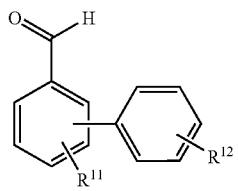

(IV)

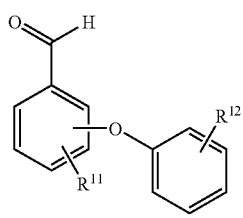

(V)

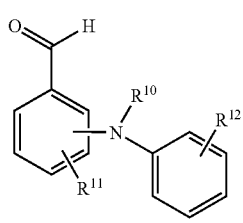

Substituted biaryl aldehyde intermediates of general Formulae (III) may be prepared as outlined in Scheme 4. It is appreciated that one skilled in the art could readily apply the methods described below to make additional substituted biphenyl aldehydes of Formula (III). In this approach, a suitably substituted aryl iodide or bromide can serve as a common intermediate for the preparation of biaryl aldehydes through metal-mediated cross coupling reactions of the type described by Fu et al. (*J. Amer. Chem. Soc.* 2000, 122, 4020–4028). For example, 2-formylphenylboronic acid can be coupled with methyl 2-iodobenzoate in the presence of a palladium catalyst, such as tetrakis(triphenylphosphine)palladium, a suitable base, such as aqueous sodium carbonate or anhydrous potassium phosphate, in a suitable solvent such as toluene, toluene/EtOH mixtures, dioxane or DMF, at a reaction temperature between 85–110° C. and a reaction time of between 2–24 h.

Scheme 4

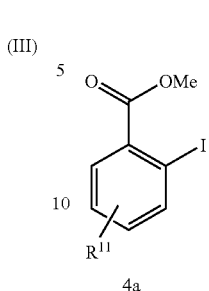 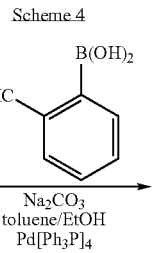

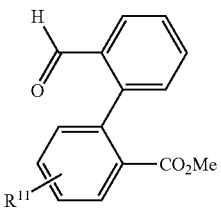

In cases where suitably substituted boronic acids are not commercially available, a modification to this approach may be adopted as is outlined in Scheme 4a. In this case an aryl bromide intermediate, for example, t-butyl 3-bromo-4-methylbenzoate 4c, is subjected to a palladium mediated coupling with a diboron species such as bis(pinacolato) diboron to provide the corresponding 4,4,5,5-tetramethyl-[1,3,2]dioxaborolane intermediate 4d using the method of Ishiyama et al. (*J. Org. Chem.* 1995, 60, 7508). Alternately, this same intermediate can be prepared by reaction of the intermediate bromide with the corresponding dialkoxyhydroborane as described by Murata et al. (*J. Org. Chem.* 1997, 62, 6458).

Scheme 4a

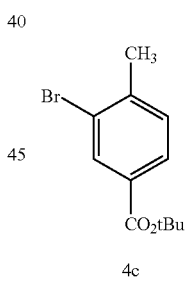 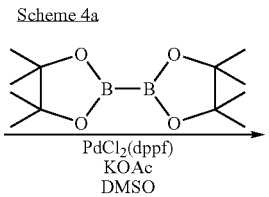

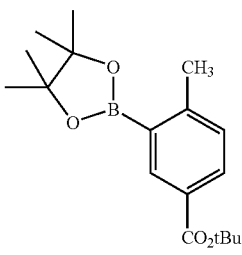

The boron pinacolate intermediates can be used as precursors for the synthesis of additional substituted aldehydes of Formula (III) through Pd-catalyzed coupling as described above with suitably substituted aryl bromides, iodides or triflates as illustrated in Scheme 4b.

Scheme 4b

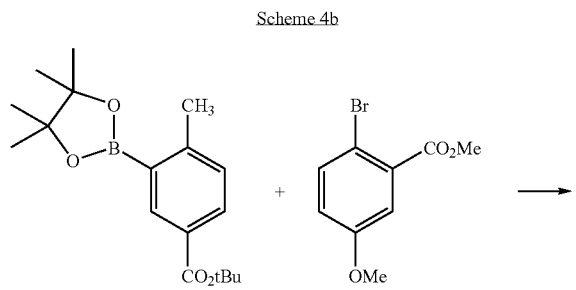

The approaches described herein when applied to the synthesis of biaryl aldehyde intermediates can therefore facilitate the synthesis of a wide range of intermediates derived from either aryl halides or phenols, the precursors to aryl triflates.

It is also realized that the scope of intermediate synthesis can be further extended outside the use of Suzuki methodology since the precursor aryl halides or triflates described above are also precursors for Stille-type cross coupling methodologies. Suitable methodology for the synthesis of substituted aldehydes of Formula III using Stille coupling has been reported by Kohrt et al. (*Tetrahedron Lett.* 2000, 41, 6041–44).

Intermediate aldehydes of the general Formula (IV) may be synthesized via an Ullmann-type copper-mediated displacement of an aryl bromide with a suitably substituted phenol or a copper mediated cross-coupling reaction of a phenol with aryl boronic acids using the methodology developed by Chan and co-workers (see *Tetrahedron Lett.* 1998 39, 2933).

Aldehyde intermediates of the general Formula (V) may be prepared in similar fashion by N-arylation of a suitably substituted aniline intermediate either through a copper-promoted coupling with boronic acids or via palladium mediated N-arylation of anilines with aryl halides or triflates as described by Buchwald and co-workers (see *Tetrahedron Lett,* 1997, 38, 6359 & 6363).

Tetrahydoquinoline compounds useful for the synthesis of compounds of this invention can be prepared as outlined in Scheme 5 via a Schmidt rearrangement of an appropriately substituted indanone 5a to provide tetrahydroquinolone 5b which can be reduced to the corresponding tetrahydroquinoline by treatment with lithium aluminum hydride to give compound 5c. Further elaboration of 5c as described above and in the following specific examples gives additional compounds of the invention such as, for example, 5h. Alternate methods for preparation of useful tetrahydroquinoline starting materials include, but are not limited to the reduction of the corresponding quinoline compounds using transfer hydrogenation (see P. Balczewski & J. A. Joule *Synth. Commun.* 1990, 20, 2815) or lithium triethylborohydride (see B. E. Blough & F. I. Carroll, *Tetrahedron Lett.* 1993, 34, 7239). Additional methodology for the synthesis of tetrahydroquinoline ring systems has been recently reviewed by Katritzky et al. (*Tetrahedron* 1996, 52, 15031–15070) and can be used by one skilled in the art of organic synthesis to prepare additional examples of the present invention.

Scheme 5

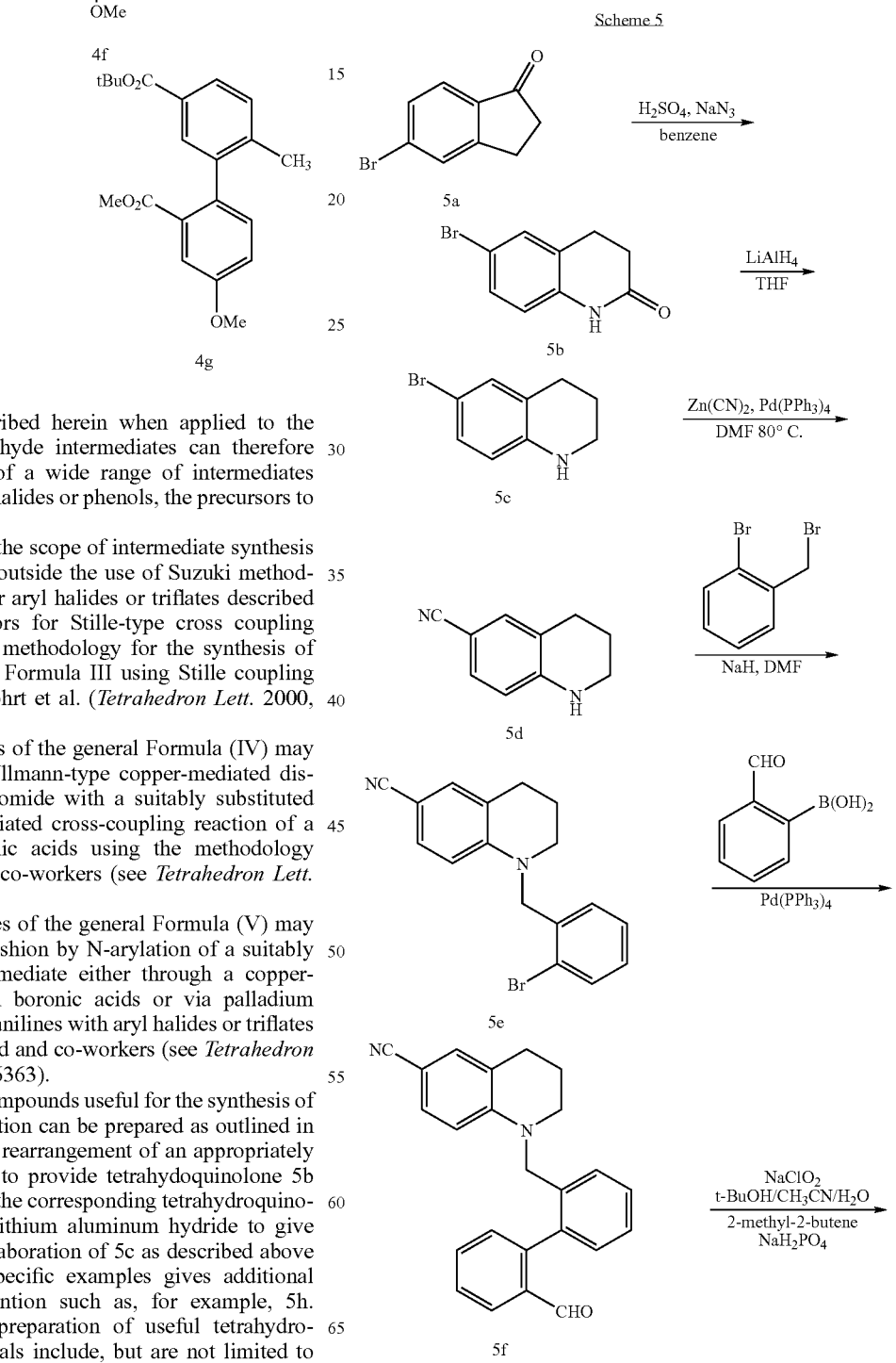

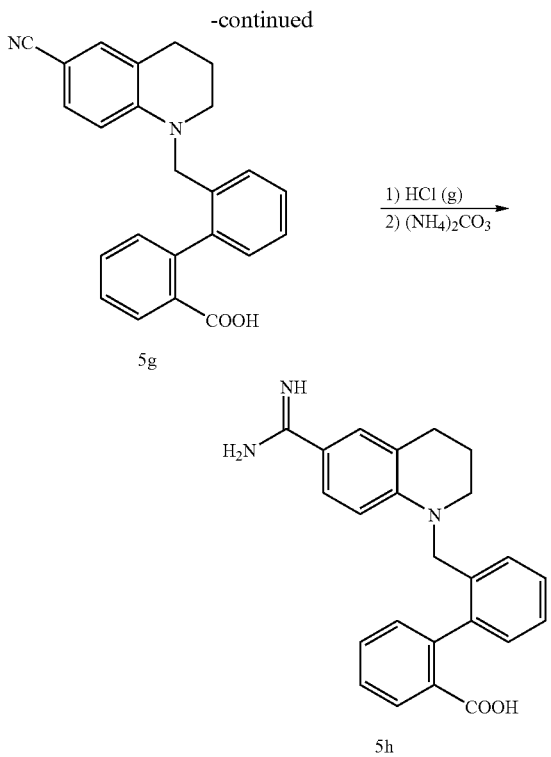

Other features of the invention will become apparent in the course of the following descriptions of exemplary embodiments that are given for illustration of the invention and are not intended to be limiting thereof.

EXAMPLES

Solution ratio expresses a volume relationship, unless stated otherwise. NMR chemical shifts (δ) are reported in parts per million. Flash chromatography was carried out on silica gel according to Still's method (Still, W. C. et al. *J. Org. Chem.* 1978, 43, 2923).

As used throughout the specification, the following abbreviations for chemical reagents apply:

HOAc or AcOH=acetic acid
Bn=benzyl
Bu=butyl
t-Bu=tertiary butyl
Boc=tert-butyl oxycarbonyl
$CH_2Cl_2$=dichloromethane
DCE=1,2-dichloroethane
DMF=dimethylformamide
DMSO=dimethyl sulfoxide
Et=ethyl
$Et_2O$=diethyl ether
EtOH=ethanol
EtOAc=ethyl acetate
HCl=hydrochloric acid
Me=methyl
MeOH=methanol
NaOAc=sodium actetate
$Na_2SO_4$=sodium sulfate
OAc=acetate
Ph=phenyl
Pr=propyl
i-Pr=isopropyl
i-PrOH=isopropanol
TFA=trifluoroacetic acid
THF=tetrahydrofuran
° C.=degrees Celsius
anh.=anhydrous
atm=atmosphere
conc.=concentrated
eq=equivalent(s)
h or hr=hour(s)
g=gram(s)
mg=milligram(s)
L=liter(s)
mL=milliliter(s)
μL=microliter(s)
mmol=millimolar
M=molar
meq=milliequivalent(s)
Min=minute(s)
MW=molecular weight
mp=melting point
rt or RT=room temperature
sat or sat'd=saturated
ESI=electrospray ionization mass spectroscopy
HPLC=high performance liquid chromatography
MS=mass spectrometry
LC/MS=liquid chromatography mass spectrometry
NMR=nuclear magnetic resonance spectroscopy
TLC=thin layer chromatography "α", "β", "R", "S", "E", and "Z" are stereochemical designations familiar to one skilled in the art. One stereoisomer of a compound of Formula I may display superior activity compared with the others. Thus, each stereoisomer of a compound of Formula I is considered to be a part of the present invention. When required, separation of the racemic material can be achieved by HPLC using a chiral column or by a resolution using a resolving agent such as described in Wilen, S. H. *Tables of Resolving Agents and Optical Resolutions* 1972, 308 or using enantiomerically pure acids and bases. A chiral compound of Formula I may also be directly synthesized using a chiral catalyst or a chiral ligand, e.g., Jacobsen, E. *Acc. Chem. Res.* 2000, 33, 421–431 or using other enantio- and diastereo-selective reactions and reagents known to one skilled in the art of asymmetric synthesis.

The following Examples have been prepared, isolated and characterized using the methods disclosed herein. The following Examples demonstrate a partial scope of the invention and are not meant to be limiting of the scope of the invention.

Example 1

2'-(5-Carbamimidoyl-2,3-dihydroindol-1-ylmethyl)-biphenyl-2-carboxylic acid

Part A

Method 1:

A solution of 5-cyanoindole (3 g, 0.021 mol) in glacial acetic acid (25 mL) was treated portionwise with sodium cyanoborohydride (4 g, 0.063 mol) over 20–30 min then the solution was stirred overnight at rt under $N_2$. The reaction was quenched by addition of water, and most of acetic acid was removed in vacuo. The residue was diluted with water and adjusted to pH>8 with 1M NaOH then extracted 3× with ethyl acetate. Extracts were combined and back extracted 2× with 1M HCl then set aside. (Starting indole can be recovered from these initial EtOAc extracts if desired.) Aqueous acid extracts were combined and rebasified with 5N NaOH, and then re-extracted with EtOAc. The latter extracts were combined, washed with brine, dried over anh. $Na_2SO_4$, filtered and evaporated to provide the indoline product (1.22 g, 40%) as an off-white crystalline solid. $^1$H NMR (CDCl$_3$, 300 MHz) δ 7.29–7.31 (m, 2H), 6.54 (d, 1H, J=8.4 Hz), 4.20 (bs, 1H), 3.67 (t, 2H, J=8.6 Hz), 3.06 (t, 2H, J=8.6 Hz).

Method 2:

A solution of 5-cyanoindole (1 g, 7 mmol) in 10 mL TFA was cooled to 0° C. and then triethylsilane (1.6 g, 2 eq.) was added. The reaction mixture was stirred at 0° C. for 4 h then diluted with EtOAc and washed with 1M HCl solution. The aqueous layers were combined and neutralized with 50% NaOH to pH10 then extracted 3× with EtOAc. These latter extracts were combined, washed with brine, dried and evaporated to yield the indoline (77%).

Part B

A mixture of methyl 2-iodobenzoate (0.58 mL, 4 mmol), 2-formylphenylboronic acid (0.9 g, 6 mmol), toluene (30 mL), ethanol (12.5 mL) and 2M $Na_2CO_3$ (4 mL, 8 mmol) was degassed, then tetrakis(triphenylphosphine)palladium (0.23 g, 0.05 eq.) and tetrabutylammonium bromide (65 mg, 0.05 eq.) were added under $N_2$. The mixture was heated in a 95° C. oil bath for 3–4 h, then stirred overnight at rt. The reaction was diluted with water and extracted 3× with ethyl acetate. The combined extracts were washed with brine, dried over anh. $Na_2SO_4$, filtered and evaporated. The product was purified by flash chromatography (silica gel, hexane/ethyl acetate 90:10 to 85:15) to provide the desired biphenyl aldehyde as a light yellow oil (0.8 g, 83%). $^1$H NMR (CDCl$_3$, 300 MHz) δ 9.80 (s, 1H), 8.07–8.00 (m, 2H), 7.63–7.49 (m, 4H), 7.31–7.23 (m, 2H), 3.62 (s, 3H).

Part C

The compound of Part A (0.1 g, 0.694 mmol) was dissolved in 1,2-dichloroethane (DCE) (2.5 mL) and a solution of the compound of Part B (80 mg, 0.33 mmol) in DCE (1.5 mL) was added. This mixture was stirred for 10–15 min, then treated with sodium triacetoxyborohydride (0.1 g, 0.48 mmol) and stirred overnight at rt under $N_2$. Reaction was quenched by addition of water and 1N NaOH, then extracted 3× with $CH_2Cl_2$. Combined extracts were washed with brine, dried over $Na_2SO_4$, filtered and evaporated. Chromatography on silica gel (hexane/ethyl acetate 4:1) provided the product (0.105 g, 86%). $^1$H NMR (CDCl$_3$, 300 MHz) δ 7.94 (d, 1H, J=7.5 Hz), 7.50-(t, 1H, J=7.5 Hz), 7.41 (t, 1H, J=7.5 Hz), 7.34–7.30 (m, 2H), 7.23–7.11 (m, 4H), 5.99 (d, 1H, J=8.4 Hz), 4.08 (dd, 2H, J=24.2, 15.8 Hz), 3.59 (s, 3H), 3.33 (m, 2H), 2.91 (t, 2H, J=8.4 Hz). LRMS m/z 369.0 (M+H)$^+$ (API$^+$). HRMS Calcd. for $C_{24}H_{21}N_2O_2$: 369.1603. Found: 369.1580.

Part D

A mixture of the compound of Part C (72 mg, 0.195 mmol), hydroxylamine hydrochloride (30 mg, 0.43 mmol) and triethylamine (60 μL, 0.43 mmol) in ethanol (1 mL) was heated in 95° C. oil bath for 2 h, then stirred overnight at rt. The mixture was then stripped to dryness and redissolved in acetic acid (1 mL) and added dropwise to a stirred mixture of Zinc dust (130 mg, 2 mmol), acetic acid (1 mL) and acetic anhydride (30 μL, 0.32 mmol). The mixture was stirred overnight at rt, then filtered through a pad of Celite® and solid washed with methanol. The filtrate was evaporated, triturated with ether, dried in vacuo, then purified by reverse phase HPLC to provide the amidine (21 mg, 18.5%) as the bis-TFA salt. $^1$H NMR (DMSO-d$_6$, 300 MHz) δ 8.72 (s, 2H), 8.33 (s, 2H), 7.86 (d, 1H, J=7 Hz), 7.61 (t, 1H, J=7.5 Hz), 7.52–7.43 (m, 3H), 7.33 (m, 4H), 7.07 (m, 1H), 6.17 (d, 1H, J=9 Hz), 4.17 (m, 2H), 3.52 (s, 3H), 3.35 (m, 2H under solvent peak), 2.93 (m, 2H). HRMS calcd. For $C_{24}H_{24}N_3O_2$: 386.1869. Found: 386.1880.

Part E

The compound of Part D (10 mg, 0.016 mmol) was dissolved in methanol (2 mL) and 1M NaOH (0.5 mL) was added. The mixture was refluxed for 4.5 h, cooled to rt and the solution neutralized by addition of 1M HCl then evaporated to dryness. Purification by reverse phase HPLC provided the bis TFA salt of the acid (3 mg) as a white solid after lyophilization. MS m/z 372.3 (M+H)$^+$.

Example 2

2'-(5-Carbamimidoyl-2,3-dihydroindol-1-ylmethyl)-biphenyl-2,4-dicarboxylic acid

Part A

A mixture of 5-cyanoindoline (70 mg, 0.487 mmol) and 2'-formylbiphenyl-2,4-dicarboxylic acid 4-ethyl ester 2-methyl ester (0.512 mmol) in 4 mL DCE was stirred for 10 min followed by addition of sodium triacetoxyborohydride (0.155 g, 1.5 eq.). Stirring was continued at rt overnight under $N_2$. Reaction was quenched by addition of 1M NaOH then extracted 3× with $CH_2Cl_2$. Combined extracts were washed with brine, dried over anh. $Na_2SO_4$, filtered and evaporated. Flash silica gel chromatography (hexane/ethyl acetate 85:15) provided the product (0.164 g, 76%) as a white, sticky foam. $^1$H NMR (CDCl$_3$, 300 mHz) δ 8.58 (s, 1H), 8.14 (d, 1H, J=8.4 Hz), 7.36–7.30 (m, 4H), 7.18–7.13 (m, 4H), 6.00 (d, 1H, J=8.4 Hz), 4.44 (q, 2H, J=7.3 Hz), 4.07 (m, 2H), 3.64 (s, 3H), 3.29 (m, 2H), 2.90 (m, 2H), 1.44 (t, 3H, J=7.3 Hz). LRMS (API$^+$) m/z 441.2 (M+H) $^+$ [100].

Part B

A mixture of the compound of Part A (0.16 g, 0.363 mmol), hydroxylamine hydrochloride (50.2 mg, 2 eq.), and triethylamine (0.0 mL, 2 eq.) in ethanol (5 mL) was heated with stirring at reflux for 2 h then stirred overnight at rt. The resulting suspension was filtered and solid (starting nitrile) washed with EtOH. The filtrate was evaporated to dryness then redissolved in glacial acetic acid (2 mL) and treated with acetic anhydride (0.104 mL, 3 eq.). The resulting solution was stirred for 20 min at rt under $N_2$, followed by addition of zinc dust (0.24 g, 10 eq.). Stirring was continued overnight at rt. The mixture was filtered through a pad of Celite® which was washed with methanol. The filtrate was evaporated and the residue was triturated with ether and chromatographed by reverse phase Prep HPLC to provide the amidine product as the bis-TFA salt (51 mg, ~21%) as an amber oil. $^1$H NMR (DMSO-d$_6$, 300 MHz) δ 8.70 (s, 2H), 8.36 (s, 1H), 8.30 (s, 2H), 8.08 (d, 1H, J=8 Hz), 7.49 (d, 1H, j=8 Hz), 7.43–7.34 (m, 5H), 7.10 (d, 1H, J=6.6 Hz), 6.15 (d, 1H, J=9 Hz), 4.35 (q, 2H, J=7 Hz), 4.19 (s, 2H), 3.58 (s, 3H), 3.33 (m, 2H), 2.88 (m, 2H), 1.34 (t, 3H, J=7 Hz). nLRMS (ESI$^+$) m/z 458.3 (M+H$^+$).

Part C

The compound of Part B (50 mg) was dissolved in tetrahydrofuran (1.6 mL) and 1M LiOH (0.4 mL, 5.5 eq.) was added. The mixture was stirred for 4 days at rt. The reaction mixture was diluted with water and adjusted to pH 5 with 1M HCl. The solution was evaporated to dryness and the residue was chromatographed on reverse phase HPLC to provide the title compound (5 mg). $^1$H NMR (DMSO-d$_6$, 300 MHz) δ 8.72 (s, 2H), 8.37 (s, 1H), 8.32 (s, 2H), 8.04 (d, 1H, J=8 Hz), 7.43–7.29 (m, 6H), 7.12 (d, 1H, J=8 Hz), 6.18 (d, 1H, J=8 Hz), 4.18 (s, 2H), 3.34 (m, 2H under water peak), 2.93 (m, 2H). LRMS (ESI+) m/z 416.2 (M+H)$^+$. HRMS calcd. for $C_{24}H_{22}N_3O_4$: 416.1610. Found: 416.1635.

Example 3

2'-(5-Carbamimidoyl-2,3-dihydroindol-1-ylmethyl)-4-isobutylcarbamoyl-biphenyl-2-carboxylic acid Part A.

To a solution of 2-hydroxy-5-formylbenzoic acid (5.0 g, 0.03 mmol) in 80 mL of DMF was added $KHCO_3$ (3.3 g, 0.03 mmol) and benzyl bromide (3.9 mL, 0.03 mmol). The mixture was stirred at rt under $N_2$ for 20 h. The reaction mixture was poured into water (240 mL) and extracted with EtOAc. The combined organic solution was washed with brine, dried over $MgSO_4$, and concentrated to a yellow oil which was dissolved in $CH_2Cl_2$ (30 mL) and the mixture was cooled at 0° C. Pyridine (11.3 mL, 0.15 mmol) was added, followed by triflate anhydride (8.7 mL, 0.5 mmol, over 30 min). The reaction mixture was stirred at 0° C. for 30 min, poured into water and extracted with EtOAc. The combined organic solution was washed with brine and dried over $MgSO_4$, concentrated and purified by chromatography (silica gel, 10% EtOAc in hexane) to give 6.9 g of colorless oil. MS: 389 (M+1)$^+$.

Part B

The product from Part A (4.6 g, 11.9 mmol) was dissolved in a mixture of t-BuOH (45 mL), $CH_3CN$ (10 mL), and $H_2O$ (15 mL). To the solution was added 2-methyl-2-butene (6.0 mL), sodium dihydrogenphosphate (2.85 g, 23.8 mmol), and sodium chlorite (6.44 g, 71.2 mmol). The reaction mixture was stirred at rt for 2 h, then poured into water. The precipitate was filtered and dried to give 4.52 g of the acid as an off white solid. MS: 403.1 (M+1)$^-$.

Part C

The acid from Part B (2.5 g, 6.1 mmol) was dissolved in 30 mL of DMF. Isobutylamine (0.8 mL, 7.9 mmol), HBTU (3.8 g, 9.2 mmol), and N-methylmorpholine (1.7 mL, 14.0 mmol) were added. The mixture was stirred at rt under $N_2$ for 12 h. The mixture was poured into water and extracted with EtOAc. The combined organic solutions were washed with brine, dried over $MgSO_4$, concentrated and purified by chromatography (silica gel, 20% EtOAc in hexane) to give 1.5 g of light yellow solid. Mass spectrum (326.3) and $^1$HNMR indicated that it was the phenol. It was dissolved in $CH_2Cl_2$ and cooled to 0° C. Pyridine (1.9 mL) was added, followed by triflate anhydride (1.5 mL). The reaction mixture was stirred at 0° C. for 30 min. It was diluted with $CH_2Cl_2$ and washed with $H_2O$ and brine. It was dried over $MgSO_4$ and concentrated to an off white solid (1.53 g). This material was taken into the next step without further purification. $^1$HNMR (DMSO) δ 8.85 (t, 1H), 8.49 (s, 1H), 8.21 (d, 1H), 7.72 (d, 1H), 7.50–7.30 (m, 4H), 5.41 (s, 2H), 3.09 (t, 2H), 1.82 (m, 1H), 0.88 (d, 6H).

Part D

The product from Part C (2.1 g, 4.55 mmol), 2-formylphenylboronic acid (1.0 g, 6.8 mmol), $K_3PO_4$ (1.45 g, 6.8 mmol), and $Pd[PPh_3]_4$ (0.53 g, 10%) were dissolved together in 30 mL of DMF. The mixture was de-gassed and heated at 100° C. under $N_2$ for 2 h. The reaction mixture was cooled, poured into water, and extracted with EtOAc. The combined organic solution was washed with brine and dried over $MgSO_4$. It was concentrated and purified by chromatography (silica gel, 10% EtOAc in $CH_2Cl_2$) to give 1.75 g of the biaryl aldehyde. MS: 416.4 (M+1)$^+$.

Part E

A mixture of the compound of Part D (0.3 g, 0.72 mol) and 5-cyanoindoline (0.1 g, 0.694 mmol) in 2.5 mL 1,2-dichloroethane was stirred under $N_2$ for 10 min, followed by the addition of sodium triacetoxyborohydride (0.22 g, 1.04 mmol, 1.5 eq.). The mixture was then stirred overnight at rt. The reaction was quenched by addition of water and 1M NaOH and extracted 3× with $CH_2Cl_2$. Extracts were combined, washed with brine and dried over anh. $Na_2SO_4$, filtered and evaporated. Chromatography on silica gel (hexane/ethyl acetate 75:25) provided the desired alkylated product as a white foam (120 mg, 32%). $^1$HNMR (300 MHz, $CDCl_3$) δ 8.27 (s, 1H); 7.93 (d, 1H); 7.30 (6H, m); 7.13–7.02 (6H, m); 6.18 (1H, bt), 5.88 (d, 1H, J=6 Hz); 5.03 (2H, dd, J=18, 10.8); 3.96, (s, 2H); 3.32 (t, 2H, J=6 Hz); 2.81 (t, 2H, J=6 Hz); 1.92 (m, 1H); 1.00 (6H, d, J=6.6 Hz). MS m/z 544.3 (M+H)$^+$.

Part F

The compound of Part E was dissolved in 5 mL EtOH and treated with 50 mg hydroxylamine hydrochloride and 0.1 mL triethylamine followed by stirring at reflux overnight. The mixture was cooled to rt and the solvent was removed in vacuo. The residue was suspended in glacial HOAc and treated with acetic anhydride (3 eq.). The resulting solution was stirred for 20 min at rt followed by addition of Zn dust (10 eq.) and stirring overnight under $N_2$. Filtration through a pad of Celite® (solids washed with MeOH), evaporation of filtrate and trituration with $Et_2O$ provided crude material which was purified by reverse phase HPLC to provide the amidine (59 mg, 34%). MS m/z 561.3 (M+H)$^+$.

Part G

The compound of Part F (59 mg, 0.075 mmol) was dissolved in 2 mL THF and treated with 0.5 mL 1M LiOH. The mixture was agitated overnight at rt. The product was isolated from remaining starting material by reverse phase HPLC to provide the target compound (12 mg, 23%). $^1$HNMR (300 MHz, $DMSOd_6$) δ 8.71 (s, 2H); 8.65 (m, 1H); 8.32 (s, 2H); 8.00 (d, 1H, J=7 Hz); 7.46–7.28 (m, 7H); 7.13 (m, 1H); 6.10 (d, 1H, J=8.4 Hz); 4.19 (s, 2H); 3.11 (2H, bt); 2.94 (2H, bt); 1.85 (m, 1H); 0.89 (6H, d, J=6.6 Hz). HRMS calcd. for $C_{28}H_{31}N_4O_3$: 471.2398 (M+H)$^+$. Found: 471.2371.

Example 4

2'-(5-Carbamimidoyl-2,3-dihydroindol-1-ylmethyl)-4-methoxybiphenyl-2-carboxylic acid Part A Methyl 2-bromo-4-methoxybenzoate (0.98 g, 4 mmol) and 2-formylphenylboronic acid (0.9 g, 6 mmol) were dissolved in a mixture of 30 mL toluene and 12.5 mL EtOH. The solution was degassed and then 4 mL of 2M $Na_2CO_3$ solution (2 eq.) followed by tetrakis(triphenylphosphine) palladium (0.23 g, 0.05 eq.) and tetrabutylammonium bromide (0.065 g, 0.05 eq.) were added. The resulting mixture was stirred and heated overnight in a 95° C. oil bath under reflux and $N_2$. After cooling to rt, the reaction was quenched with water and extracted 3× with ethyl acetate. The combined extracts were washed with brine, dried over anh. $Na_2SO_4$, filtered and evaporated. Chromatography on silica gel (Hexane-ethyl acetate 85/15 to 75/25) provided the biaryl aldehyde. $^1$HNMR (300 MHz, $CDCl_3$) δ 7.99 (d, 1H, J=7 Hz); 7.61–7.55 (m, 2H); 7.49 (t, 1H, J=7 Hz); 7.22 (m, 2H); 7.12 (d, 1Hd, J=9.3 Hz) 3.91 (s, 3H); 3.60 (s, 3H).

Part B

The aldehyde from Part A was coupled to 5-cyanoindoline using the procedure described for Example 2, Part A to provide 0.26 g of the alkylated indoline (93%). $^1$HNMR (300 MHz, CDCl$_3$) δ 7.44 (d, 1H, J=3 Hz); 7.35–7.01, m, 9H); 6.00 (d, 1H, J=8.5 Hz); 4.08 (2H, dd, J=24,12); 3.86 (s, 3H); 3.59 (s, 3H); 3.35 (m, 2H); 2.92 (t, 2H, J=8.5 Hz). MS m/z 399.3 (M+H)$^+$.

Part C

The compound of Part B was converted into the title compound using the procedures described for Example 3, Part F and G. $^1$HNMR (300 MHz, DMSO-d$_6$) δ 8.73 (s, 2H); 8.37 (s, 2H); 7.46–7.05 (m, 9H); 6.21 (d, 1H, J=9 Hz); 4.18 (2H, dd, J=24, 16 Hz); 3.81 (s, 3H); 3.40 (m, 2H); 2.96 (t, 2H, J=8.5 Hz). HRMS calcd for C$_{24}$H$_{24}$N$_3$O$_3$: 402.1818 (M+H)$^+$. Found: 402.1819.

Example 5

4-Acetylamino-2'-(5-carbamimidoyl-2,3-dihydroindol-1-ylmethyl)-biphenyl-2-carboxylic acid Part A Methyl 2-bromo-5-nitrobenzoate was coupled to 2-formylphenylboronic acid using the procedure described for Example 4, Part A to provide methyl 2-(2'-formylphenyl)-5-nitrobenzoate. $^1$HNMR (300 MHz, CDCl$_3$) δ 8.91 (s, 1H); 8.42 (d, 1H, J=8.5 Hz); 8.00 (d, 1H, J=8.5 Hz); 7.64 (m, 2H); 7.47 d, 1H, J=8.5 Hz); 7.22 (d, 1H, J=8.5 Hz); 3.71 (s, 3H).

Part B

The aldehyde from Part A was coupled to 5-cyanoindoline using the procedure described for Example 2, Part A to provide a 48% yield of the alkylated indoline. MS m/z 414.2 (M+H)$^+$.

Part C

The compound of Part B was converted into the title compound using the procedures described for Example 3, Part F and G. $^1$HNMR (300 MHz, DMSO-d$_6$) δ 12.68 (1H, bs); 10.17, (s, 1H); 8.72 (s, 2H); 8.33 (s, 2H); 8.09 (s, 1H); 7.78 (d, 1H, J=8 Hz); 7.45 (m, 2H); 7.27 (m, 3H); 7.19 (d, 1H, J=8 Hz); 7.08 (m, 1H); 6.24 (d, 1H, J=9 Hz); 4.17 (s, 2H); 3.40 (m, 2H); 2.96 (t, 2H, J=8.8 Hz); 2.07 (s, 3H). HRMS calcd. For C$_{25}$H$_{25}$N$_4$O$_3$: 429.1927 (M+H)$^+$. Found: 429.1925.

Example 6

2'-(5-Carbamimidoyl-2,3-dihydroindol-1-ylmethyl)-4'-methoxy-biphenyl-2-carboxylic acid Part A Methyl 2-iodobenzoate was coupled to 2-formyl-4-methoxyphenylboronic acid using the procedure described in Example 4, Part A to provide methyl 2-(2'-formyl-4'-methoxyphenyl)benzoate. $^1$HNMR (300 MHz, CDCl$_3$) δ 9.74 (s, 1H); 8.02 (d, 1H, J=7.7 Hz); 7.57 (t, 1H J=7.7 Hz); 7.50 (m, 2H); 7.28, 1, m); 7.17 (s, 2H); 3.91 (s, 3H); 3.64 (s, 3H).

Part B

The reductive amination of 5-cyanoindoline with the aldehyde of Part A using the conditions described in Example 2, Part A provided the alkylated indoline intermediate in 77% yield. MS m/z 399.2 (M+H)$^+$.

Part C

The compound of Part B was converted into the title compound using the procedures described in Example 3, Part F and G. $^1$HNMR (300 MHz, DMSO-d$_6$) δ 12.65 (1H, bs); 8.74 (s, 2H); 8.43 (s, 2H); 7.81 (d, 1H, J=7.3 Hz); 7.53 (t, 1H, J=7.3 Hz); 7.44 (m, 3H); 7.25 (d, 1H, J=7.7 Hz); 7.03 (d, 1H, J=8.5 Hz); 6.88 (d, 1H, J=8.4 Hz); 6.83 (s, 1H); 6.21 (d, 1H, J=8.8 Hz); 4.15 (s, 2H); 3.75 (s, 3H); 3.40 (m, 2H); 2.95 (t, 2H, J=8.4 Hz). HRMS calcd. for C$_{24}$H$_{24}$N$_3$O$_3$: 402.1818 (M+H)$^+$. Found: 402.1825.

Example 7

2'-(5-Carbamimidoyl-2,3-dihydro-indol-1-ylmethyl)-4-carbamoyl-biphenyl-2-carboxylic acid Part A 2-Bromo-5-iodobenzoic acid (6.54 g, 20.0 mmol) was dissolved in DMF (70 mL). Potassium bicarbonate (2.2 g, 22.0 mmol) was added, followed by benzyl bromide (2.8 mL, 22.0 mmol). The mixture was stirred at rt under N$_2$ for 12 h. The reaction mixture was poured into water and extracted with EtOAc. The combined organic solution was washed with brine, dried over MgSO$_4$, and concentrated and dried to give 9.05 g of the benzyl ester.

Part B

The compound of part A (2.3 g, 7.69 mmol), Zn(CN)$_2$ (1.3 g, 11.5 mmol), and Pd[PPh$_3$]$_4$ were dissolved together in 25 mL of DMF. The mixture was de-gassed and heated at 90° C. for 4 h. Reaction mixture was concentrated and purified by chromatography (silica gel, 5% EtOAc in hexane) to give 1.8 g of the benzonitrile. MS: 316.0, 317.9 (M+1)$^+$.

Part C

The compound of Part B (1.4 g, 4.4 mmol) was dissolved in 15 mL of DMF. The reaction mixture was cooled at 0° C. Potassium carbonate (0.20 g, 1.45 mmol) was added, followed by dropwise addition of 30% hydrogen peroxide solution (1.2 mL). The cooling bath was removed and the mixture was stirred at rt for 12 h. The reaction was quenched with aqueous NaHSO$_3$ and water. The formed precipitate was filtered and dried to give 1.1 g of the desired amide. MS: 334.2, 336.3 (M+1)$^+$.

Part D

A mixture of the compound of Part C (0.6 g, 1.8 mmole), 2-formylphenylboronic acid (0.45 g, 3 mmol) and anhydrous K$_3$PO$_4$ (0.63 g, 3 mmol) in 8 mL of 1,4-dioxane was stirred and degassed, then tetrakis(triphenylphosphine)palladium (0.16 g, 0.14 mmol) was added. The whole mixture was heated to 100° C. for 3–4 h followed by stirring overnight at rt under N$_2$. The reaction was quenched by addition of brine and extracted 3× with EtOAc. The combined extracts were washed with brine, dried over Na$_2$SO$_4$, filtered and evaporated in vacuo. Chromatography on silica gel (hexane/ethyl acetate 1:1) provided the biarylaldehyde (0.4 g, 62%). $^1$HNMR (500 MHz, CDCl$_3$) δ 9.75 (s, 1H); 8.46 (s, 1H); 8.07 (d, 1H, J=7.7 Hz); 7.87 (s, 1H, J=7.7 Hz); 7.54 (t, 1H, J=7.7 Hz); 7.46 (t, 1H, J=7.7 Hz); 7.38 (d, 1H, J=8.2 Hz); 7.30 (m, 3H); 7.18 (d, 1H, J=7.7 Hz; 7.08 (m, 2H); 5.05 (s, 2H).

Part E

Reductive amination of 5-cyanoindoline with the aldehyde of Part D using the conditions described in Example 2, Part A provided the alkylated indoline intermediate in 63% yield.

Part F

The compound of Part E was converted into the title compound using the procedures described for Example 3, Part F and G. $^1$HNMR (300 MHz, DMSO-$d_6$) δ 8.72 (s, 2H); 8.34 (m, 1H); 8.31 (s, 2H); 8.17 (s, 1H); 8.01 (m, 1H); 7.53 (s, 1H); 7.43 (m, 1H); 7.42 (m, 1H); 7.37 (m, 2H); 7.33 (m, 1H); 7.32 (m, 2H); 7.11 (m, 1H); 6.19 (d, 1H, J=8.2 Hz); 4.18 (m, 2H); 3.39 (m, 2H); 2.93 (m, 2H). HRMS calcd. For $C_{24}H_{23}N_4O_3$: 415.1770 (M+H)$^+$. Found: 415.1765.

Example 8

2'-(6-Carbamimidoyl-2,3-dihydro-indol-1-ylmethyl)-biphenyl-2-carboxylic acid

The title compound was prepared in analogous fashion to Example 1 above using 3-formylphenylboronic acid in place of 2-formylphenylboronic acid. $^1$HNMR (300 MHz, DMSO-$d_6$) δ 8.76 (s, 2H); 8.35 (s, 2H); 7.72 (d, 1H, J=7.3 Hz); 7.59 (m, 1H); 7.50 (s, 1H); 7.45 (t, 1H, J=7.4 Hz); 7.38 (t, 1H, J=6.6 Hz); 7.27 (m, 2H); 6.74 (d, 1H, J=8.4 Hz); 4.53 (s, 2H); 3.60 (m, 2H); 3.05 (t, 2H, J=8.8 Hz). HRMS calcd. For $C_{23}H_{22}N_3O_2$: 372.1712 (M+H)$^+$. Found: 372.1730.

Example 9

2'-(6-Carbamimidoyl-2,3-dihydro-indol-1-ylmethyl)-biphenyl-2,4-dicarboxylic acid The title compound was prepared in analogous fashion to Example 2 above using 3-formylphenylboronic acid in place of 2-formylphenylboronic acid. $^1$HNMR (300 MHz, DMSO-$d_6$) δ 8.77 (s, 2H); 8.37 (s, 2H); 8.26 (s, 1H); 8.09 (d, 1H, J=8 Hz); 7.52 (d, 1H, J=8.5 Hz); 7.43 (m, 2H); 7.32 (m, 3H); 6.74 (d, 1H, J=8.5 Hz); 4.54 (s, 2H); 3.58 (t, 2H, J=8.5 Hz); 3.05 (t, 2H, J=8.5 Hz). HRMS calcd. For $C_{24}H_{22}N_3O_4$: 416.1610 (M+H)$^+$. Found: 416.1625.

Example 10

1-(2'-Sulfamoyl-biphenyl-3-ylmethyl)-2,3-dihydro-1H-indole-5-carboxamidine

Part A 2-(t-Butylaminosulfonyl)phenylboronic acid (1.0 g, 3.98 mmol), 3-bromobenzaldehyde (0.46 mL, 3.98 mmol), $K_3PO_4$ (1.27 g, 5.97 mmol), and Pd[PPh$_3$]$_4$ (0.46 g, 10%) were dissolved together in 30 mL of dioxane. The mixture was de-gassed and heated at 110° C. under $N_2$ for 12 h. The reaction mixture was cooled, poured into water, and extracted with EtOAc. The combined organic solution was washed with brine and dried over MgSO$_4$. It was concentrated and purified by chromatography (silica gel, 25% EtOAc in hexane) to give 1.15 g of the biarylaldehyde. MS: 339.3 (M+Na)$^+$.

Part B

Reductive amination of 5-cyanoindoline with the aldehyde of Part A using the conditions described in Example 2, Part A provided the alkylated indoline intermediate in 52% yield. $^1$HNMR (300 MHz, CDCl$_3$) δ 8.16 (d, 1H, J=8.5 Hz); 7.60–7.22 (m, 9H); 6.39 (d, 1H, J=8 Hz); 4.40 (s, 2H); 3.61 (t, 2H, J=8.8 Hz); 3.47 (s, 1H); 3.06 (t, 2H, J=8.8 Hz); 0.99 (s, 9H). MS m/z 446.2 (M+H)$^+$.

Part C

The compound of Part B was converted into the title compound using the procedures described for Example 3, Part F and G. HRMS calcd. For $C_{22}H_{23}N_4O_2S$: 407.1542 (M+H)$^+$. Found: 407.1546.

Example 11

[2'-(5-Carbamimidoyl-2,3-dihydro-indol-1-ylmethyl)-biphenyl-3-yl]-acetic acid

Part A

To a solution of 3-bromophenylacetic acid (1 g, 4.65 mmol) in 20 mL MeOH at 0° C. was added thionyl chloride (0.51 mL, 1.5 eq.) dropwise. The resulting solution was then refluxed overnight under $N_2$. The reaction was cooled to rt and the solvent was removed in vacuo. The residue was taken up in EtOAc, washed with sat'd. NaHCO$_3$ and brine, then dried over Na$_2$SO$_4$, filtered and evaporated to provide the methyl ester in 98% yield. $^1$HNMR (300 MHz, CDCl$_3$) δ 7.57 (d, 1H, J=12 Hz); 7.29 (2H, dd, J=2.5, 0.8 Hz); 7.16 (m, 1H); 3.81 (s, 2H); 3.72 (s, 3H).

Part B

The bromide of Part A was coupled to 2-formylphenylboronic acid using the conditions described in Example 4, Part A to provide the biarylaldehyde intermediate which was used without purification in Part C.

Part C

Reductive amination of 5-cyanoindoline with the aldehyde of Part B using the conditions described in Example 2, Part A provided the corresponding indoline intermediate in 75% yield. MS m/z 383.3 (M+H)$^+$.

Part D

The compound of Part C was converted into the title compound using the procedures described for Example 3, Part F and G. $^1$HNMR (300 MHz, DMSO-$d_6$) δ 8.73 (s, 2H); 8.30 (s, 2H); 7.45 (m, 2H); 7.37 (m, 4H); 7.26 (m, 4H); 6.35 (d, 1H, J=8 Hz); 4.43 (s, 2H); 3.61 (s, 2H); 3.8. (m, 2H); 2.92 (t, 2H, J=8.5 Hz). MS 386.4 (M+H)$^+$.

Example 12

5'-Acetylamino-2'-(5-carbamimidoyl-2,3-dihydro-indol-1-ylmethyl)-biphenyl-2-carboxylic acid Part A Suzuki coupling of 2-bromo-4-nitrotoluene to 2-formylphenylboronic acid using the conditions described in Example 4, Part A provided 2-(2'-bromo-5'-nitrophenyl) benzaldehyde. $^1$HNMR (300 MHz, CDCl$_3$) δ 9.78 (s, 1H); 8.20 (d, 1H, J=8.5 Hz); 8.09 (s, 1H); 8.05 (d, 1H, J=7.7 Hz); 7.71 (t, 1H, J=7.4 Hz); 7.61 (t, 1H, J=7.3 Hz); 7.47 (d, 1H, J=8.4 Hz); 7.29 (d, 1H, J=7.4 Hz); 2.19 (s, 3H).

Part B

The aldehyde of Part A (2.29 g, 9.5 mmol) was dissolved in a mixture of 150 mL t-BuOH and 25 mL CH$_3$CN. To this solution, 50 mL water, NaH$_2$PO$_4$ (1.71 g, 1.5 eq.) and 2-methyl-2-butene (4 mL, 4 eq.) were added. The mixture was stirred at rt and sodium chlorite (3.86 g, 4.5 eq.) was added in one portion. Stirring was continued for 1 h at which point the reaction was diluted with water and extracted 3× with EtOAc. The combined extracts were washed with brine, dried over $Na_2SO_4$, filtered and evaporated to provide 3 g of the crude acid which was used without purification for conversion to the methyl ester.

Part C

The compound of Part B was esterified using the procedure described for Example 11, Part A to provide the corresponding methyl ester in 83% yield. $^1$HNMR (300 MHz, $CDCl_3$) δ 8.10 (m, 2H); 7.97 (s, 1H); 7.61 (t, 1H, J=7.7 Hz); 7.51 (t, 1H, J=7.7 Hz); 7.39 (1, d, J=8.4 Hz); 7.04 (d, 1H, J=7.7 Hz); 3.67 (s, 3H); 2.15 (s, 1H).

Part D

A solution of the compound of Part C (2.15 g, 7.93 mmol) in 20 mL $CCl_4$ was treated with NBS (1.55 g, 1.1 eq.) followed by benzoyl peroxide (85 mg, 0.045 eq.) and the mixture was heated to 80–90° C. in an oil bath under $N_2$ and under a tungsten lamp overnight. After cooling to rt, the mixture was diluted with $CH_2Cl_2$ and washed with water and brine, dried over $Na_2SO_4$, filtered and evaporated, to provide a mixture of starting material, monobromo and dibromo products. Chromatography on silica gel (Hexane/ethylacetate 95/5-90/10) provided 2 g of the monobromo product (72%) as a white solid. $^1$HMR (300 MHz, $CDCl_3$) 8.22 (d, 1H, J=8.4 Hz); 8.12 (d, 1H, J=7.7 Hz); 7.99 (s, 1H); 7.66 (m, 2H); 7.54 (t, 1H, J=7.7 Hz); 7.35 (d, 1H, J=7.7 Hz); 4.25 (2H, dd, J=49, 10.3 Hz); 3.68 (s, 3H).

Part E

To a solution of 5-cyanoindoline (0.5 g, 3.47 mmol) and the compound of Part D (1.3 g, 1.1 eq.) in 10 mL of DMF was added sodium hydride (60% in oil, 0.15 g, 1.1 eq.). The mixture was stirred overnight at rt. The reaction was diluted with water and extracted 3× with EtOAc. The combined extracts were washed with water and brine and then dried over $Na_2SO_4$, filtered and evaporated. Flash chromatography on silica gel (hexane/$CH_2Cl_2$/EtOH 20/80/0.5) provided the desired alkylated product (0.44 g, 31%, MS m/z 414.2 $(M+H)^+$) along with 68% of unreacted starting material.

Part F

The compound of Part E was converted into the title compound using the procedures described for Example 3, Part F and G. $^1$HNMR (300 MHz, DMSO-$d_6$) δ 9.96 (s, 1H); 8.71 (s, 2H); 8.26 (s, 2H); 7.83 (d, 1H, J=7.7 Hz); 7.60–7.20 (m, 9H); 6.15 (d, 1H, J=8.8 Hz); 4.10 (s, 2H); 3.37 (t, 2H, J=8.4 Hz); 2.92 (t, 2H, J=8.4 Hz); 2.02 (s, 3H). HRMS calcd. For $C_{25}H_{25}N_4O_3$: 429.1927. Found: 429.1929.

Example 13

2'-(5-Carbamimidoyl-2,3-dihydro-indol-1-ylmethyl)-5'-phenethylcarbamoyl-biphenyl-2-carboxylic acid Part A A suspension of 3-bromo-4-methylbenzoic acid (2.15 g, 10 mmol) in 15 mL toluene was heated to 80° C. and N,N-DMF-di-t-butylacetal (9.7 mL) was added dropwise over 20 min. The resulting solution was heated for an additional 30 min at 80° C. then cooled to rt, diluted with EtOAc and washed with water, sat'd $NaHCO_3$ and brine, dried over $Na_2SO_4$, filtered and evaporated in vacuo to provide the t-butyl ester (1.95 g, 72%) which was used without purification.

Part B

The compound of Part A was coupled to 2-formylphenylboronic acid using the conditions described in Example 4, Part A. Chromatography on silica gel (hexane.ethyl acetate 9:1) provided the pure material as a light yellow crystalline solid in 72% yield. $^1$HNMR (300 MHz, $CDCl_3$) δ 9.73 (s, 1H); 8.04 (d, 1H, J=7.7 Hz); 7.96 (d, 1H, J=7.7 Hz); 7.54 (t, 1H, J=7.7 Hz); 7.31 (m, 2H); 2.13 (s, 3H); 1.58 (s, 9H).

Part C

The compound of Part B was oxidized to the acid according to the procedure described for Example 12, Part B. The crude acid was dissolved in a mix of 8 mL benzene and 2 mL MeOH and treated dropwise under $N_2$ at rt with a 2.0 M solution of TMS-diazomethane in hexane (1.3 eq.). The resulting solution was stirred overnight at rt, then quenched with a little HOAc and diluted with EtOAc. The organic solution was washed with sat'd $NaHCO_3$ and brine, dried over $Na_2SO_4$, filtered and evaporated. Chromatography on silica gel (hexane/EtOAc 95:5) provided the methyl ester in 75% overall yield.

Part D

The compound of Part C was dissolved in 20 mL of $CCl_4$ and the solution treated with NBS (2.2 eq.) and benzoyl peroxide (cat.). The mixture was stirred overnight at reflux under a tungsten lamp. Reaction was cooled to rt, diluted with $CH_2Cl_2$ and washed with water and brine, dried and evaporated. Chromatography on silica gel (hexane/EtOAc 95:5) provided the dibromo derivative in 76% yield.

Part E

The compound of Part D (0.93 g, 1.92 mmol) was suspended in 2.5 mL of morpholine with stirring and heated in a 55–60° C. oil bath under $N_2$ overnight. The resulting mixture was cooled to rt and diluted with EtOAc. After stirring for 20 min the morpholine hydrobromide was removed by filtration and washed with additional EtOAc. The filtrate was evaporated. The residue was redissolved in EtOAc and shaken with 5% citric acid (3×) then dried over $Na_2SO_4$, filtered and evaporated. Chromatography on silica gel (hexane/ethyl acetate 9:1) provided the pure aldehyde. (0.47 g, 72%). $^1$HNMR (300 MHz, $CDCl_3$) δ 9.82 (s, 1H); 8.06 (m, 3H); 7.85 (s, 1H); 7.59 (m, 2H); 7.31 (d, 1H, J=7.7 Hz); 3.64 (s, 1H), 1.60 (s, 9H).

Part F

Reductive amination of 5-cyanoindoline with the compound of Part E according to the procedure described for Example 2, Part A provided the alkylated indoline in 78% yield.

Part G

Deprotection of the t-butyl ester was carried out by stirring the compound of Part F (0.32 g, 0.6 mmol) in a mixture of 4 mL $CH_2Cl_2$ and 1 mL TFA overnight to provide the monoacid (0.23 g, 81%).

Part H

A mixture of the compound of Part G (0.11 g, 0.26 mmol), N-methylmorpholine (0.065 mL, 2.2 eq.), phenethylamine (0.05 mL, 1.5 eq.) and Castro's reagent (0.18 g, 1.5 eq.) in DMF (1.5 mL) was stirred for 48 h at rt. The reaction was then diluted with water and extracted 3× with EtOAc. Combined extracts were washed with sat'd $NaHCO_3$ and brine then dried and evap. Purification by reverse phase HPLC provided the amide product in about 40% yield. This material was converted into the title compound using the procedures described for Example 3, Part F and G. HRMS calcd. For $C_{32}H_{31}N_4O_3$: 519.2396. Found: 519.2400.

Example 14

5'-Benzylcarbamoyl-2'-(5-carbamimidoyl-2,3-dihydro-indol-1-ylmethyl)-biphenyl-2-carboxylic acid The title compound was prepared in analogous fashion using the procedures outlined above for the preparation of Example 13 by substituting benzylamine for the phenethylamine in Example 13, Part H. $^1$HNMR (500 MHz, DMSO-$d_6$) δ 9.07 (t, 1H); 8.75 (s, 2H); 8.33 (s, 2H); 7.89 (m, 2H); 7.68 (s, 1H); 7.69 (t, 1H, J=7.7 Hz); 7.50 (t, 1H, J=7.7 Hz); 7.44 (m, 2H); 7.39 (d, 1H, J=8.2 Hz); 7.31 (m, 5H); 7.24 (m, 1H); 6.20 (d, 1H, J=8.8 Hz). HRMS calcd. For $C_{31}H_{29}N_4O_3$: 505.2240. Found 505.2260.

Example 15

2'-(5-Carbamimidoyl-2,3-dihydro-indol-1-ylmethyl)-5'-(3-phenylpropylcarbamoyl)-biphenyl-2-carboxylic acid The title compound was prepared in analogous fashion using the procedures outlined above for the preparation of Example 13 by substituting 3-phenylpropylamine for the phenethylamine in Example 13, Part H. $^1$HNMR MHz, DMSO-$d_6$) δ 8.74 (s, 2H); 8.51 (m, 1H); 8.35 (s, 2H); 7.91 (d, 1H, J=8 Hz); 7.82 (d, 1H, J=8 Hz); 7.60 (m, 2H); 7.50 (t, 1H, J=7 Hz); 7.44 (2, m); 7.37 (d, 1H, J=7 Hz); 7.32 (d, 1H, J=7 Hz); 7.26 (m, 2H); 7.21 (m, 2H); 7.17 (t, 1H, J=7 Hz); 6.19 (d, 1H, J=8.2 Hz); 4.20 (2, m); 3.44 (m, 2H); 3.25 (m, 2H); 2.96 (t, 2H, J=6 Hz); 2.61 (m, 2H); 1.81 (m, 2H). HRMS calcd. For $C_{33}H_{33}N_4O_3$: 533.5223. Found: 533.2544.

Example 16

2'-(5-Carbamimidoyl-2,3-dihydro-indol-1-ylmethyl)-5'-(2-pyridin-2-yl-ethylcarbamoyl)-biphenyl-2-carboxylic acid The title compound was prepared in analogous fashion using the procedures outlined above for the preparation of Example 13 by substituting 2-(2-pyridyl)ethylamine for the phenethylamine in Example 13, Part H.

Example 17

2'-(5-Carbamimidoyl-2,3-dihydro-indol-1-ylmethyl)-4-methoxy-5'-phenethylcarbamoyl-biphenyl-2-carboxylic acid The title compound was prepared in analogous fashion using the procedures outlined above for the preparation of Example 13 by substituting 2-formyl-4-methoxyphenylboronic acid for the 2-formylphenylboronic acid in Example 13, Part B.

Example 18

2'-(5-Carbamimidoyl-indol-1-ylmethyl)-biphenyl-2-carboxylic acid

This compound was isolated as a by-product during the preparation of the compound of Example 1. MS m/z 370.3 (M+H)$^+$.

Example 19

2'-(3-Benzyl-5-carbamimidoyl-indol-1-ylmethyl)-4-methoxy-biphenyl-2-carboxylic acid Part A A solution of 5-cyanoindole (2.84 g, 20 mmol) and benzaldehyde (4.24 g, 40 mmol) in MeOH (100 mL) was treated with powdered NaOH (0.8 g, 20 mmol) and stirred at rt for 4 days. The solvent was partially removed in vacuo and the residue diluted with $CH_2Cl_2$, washed with water (3×), and dried over $Na_2SO_4$, filtered and evaporated to a solid which was triturated with hexanes to provide 3-(hydroxyphenylmethyl)indole-5-carbonitrile as a light yellow solid (4.9 g, 98%).

Part B

The compound of Part A (4.6, 18.5 mmol) was suspended in $CH_2Cl_2$ and stirred at rt while triethylsilane (4.27 g, 37 mmol) was added followed by slow addition of trifluoroacetic acid (3.16 g, 27.75 mmol). The resulting mixture was stirred for 1 h at rt then pH was adjusted to 9–10 and the organic layer was washed with water and brine, dried and evaporated. The solid obtained was recrystallized from MeOH to give 3-(phenyl-methyl)indole-5-carbonitrile (2.5 g, 58%).

Part C

The aldehyde of Example 4, Part A (0.211 g, 0.78 mmol) was diluted in 8 mL MeOH and treated portionwise with sodium borohydride (60 mg, 1.56 mmol). The resulting mixture was stirred at rt for 1 h and then MeOH was removed in vacuo. The residue was diluted with $CH_2Cl_2$, washed with water and brine, dried and concentrated to provide 3-Methoxy-7H-dibenzo[c,e]oxepin-5-one (0.18 g, 96%).

Part D

The compound of Part C (0.15 g, 0.625 mmol) was dissolved in 15 mL MeOH and treated with trimethylsilylchloride (1.36 g, 12.5 mmol) and a catalytic amount of $ZnCl_2$. The mixture was heated at reflux for 2 days then purified by prep. HPLC to provide 2'-chloromethyl-4-methoxybiphenyl-2-carboxylic acid methyl ester (94 mg, 52%).

Part E

The compound of Part A (65 mg, 0.28 mmol) was dissolved in DMF (5 mL) and treated at 0° C. with sodium hydride (12 mg, 0.3 mmol, 60% in oil) followed by addition of the compound of Part D (79 mg, 0.27 mmol). The mixture was stirred for 5 h at rt. The reaction was quenched with water and extracted with EtOAc. The extract was washed with water and brine, dried and concentrated to give the crude alkylated product.

Part F

The compound of Part E was converted into the title compound using the procedures described for Example 3, Parts F and G. MS m/z 490.2 (M+H)$^+$.

Example 23

2'-(6-Carbamimidoyl-3,4-dihydro-2H-quinolin-1-ylmethyl)-biphenyl-2-carboxylic acid Part A:

To a solution of 5-bromo-1-indanone (5.22 g of 90% pure, 22.3 mmol) in 70 mL of benzene was added concentrated H$_2$SO$_4$ (12.6 mL) dropwise at rt. The mixture was heated to 65° C. and sodium azide (3.26 g, 44.5 mmol) was then added portionwise in 20 min. The mixture was cooled to rt, and water and EtOAc were added. The two layers were separated and the aqueous layer was extracted with EtOAc. The combined organic solution was washed with brine, dried over MgSO$_4$, and concentrated to give a brown solid. This material was purified by flash chromatography with 30–50% EtOAc in hexane to give 2.50 g of the desired amide. MS (ES$^+$) 226.2, 228.2 (M+1)$^+$. $^1$H NMR (CDCl$_3$, 300 MHz) δ (ppm): 8.08 (s, 1H), 7.30 (s, 1H), 7.26 (d, 1H), 6.62 (d, 1H), 2.92 (t, 2H), 2.60 (t, 2H).

Part B:

The product from Part A was dissolved in 60 mL of THF. It was then added dropwise to a suspension of LiAlH$_4$ (4.0 g) in 100 mL of THF at rt. The reaction mixture was heated to reflux after the addition for 1 h. It was cooled to rt, quenched with 4.5 mL of H$_2$O, 4.5 mL of 1N NaOH, and 13 mL of H$_2$O with cooling (ice-bath). It was then filtered through Celite® and washed with THF. The filtrate was dried, concentrated and purified by flash column chromatography 30%–50% EtOAc/hexane) to give 1.5 g of the desired amine. $^1$HNMR (CDCl$_3$, 300 MHz) δ (ppm): 7.08 (s, 1H), 7.02 (d, 1H), 6.40 (d, 1H), 3.30 (t, 2H), 2.76 (t, 2H), 1.95 (m, 2H).

Part C:

The product from B (0.92 g, 4.30 mmol), Zn(CN)$_2$ (1.4 g, 8.68 mmol), and Pd(Ph$_3$P)$_4$ (0.50 g) were added together with 16 mL of DMF. The mixture was de-gassed and heated at 80° C. for 20 h. It was cooled and poured into water and extracted with EtOAc. The combined organic solution was washed with brine, dried over MgSO$_4$. It was concentrated and purified by flash column chromatography (10–20% EtOAc in hexane) to give 0.30 g of the cyano compound. $^1$HNMR (CDCl$_3$, 300 MHz) δ (ppm): 7.20 (d, 1H), 7.17 (s, 1H), 6.40 (d, 1H), 3.38 (t, 2H), 2.72 (t, 2H), 1.92 (m, 2H).

The product from part C (0.28 g, 1.77 mmol) was dissolved in 8 mL of DMF. NaH (60% in mineral oil) was added. After stirring at rt under N$_2$ for 15 min, 2-bromobenzyl bromide (0.49 g, 1.95 mmol) was added. The mixture was stirred at rt under N$_2$ for 70 min. It was cooled and poured into water and extracted with EtOAc. The combined organic solution was washed with brine, dried over MgSO$_4$. It was concentrated and dried to give 0.40 g of the crude product (~85% pure). This material was used without further purification. $^1$HNMR (CDCl$_3$, 300 MHz) δ (ppm): 7.60 (d, 1H), 7.30–7.10 (m, 4H), 7.00 (d, 1H), 6.24 (d, 1H), 4.50 (s, 2H), 3.45 (t, 2H), 2.80 (t, 2H), 2.02 (m, 2H).

Part E:

The product from Part D, 2-formylphenylboronic acid (0.33 g), K$_2$CO$_3$ (0.56 g), Pd(Ph$_3$P)$_3$ (0.12 g) were dissolved in 25 mL of toluene and ethanol (2:1). The mixture was degassed and heated to reflux under N$_2$ for 2.5 h. It was cooled, filtered through Celite®, washed with EtOAc. The organic solution was concentrated and purified by flash column chromatography (10% EtOAc in hexane) to give 0.39 g of the biaryl aldehyde. $^1$HNMR (CDCl$_3$, 300 MHz) δ (ppm): 9.78 (s, 1H), 8.00 (d, 1H), 7.65–7.12 (m, 9H), 6.16 (d, 1H), 4.20 (q, 2H), 3.26 (t, 2H), 2.70 (t, 2H), 1.90 (m, 2H).

Part F.

The product from Part E (0.14 g) was added together with t-butanol (18 mL), CH$_3$CN (3 mL), and H$_2$O (6 mL). To the mixture, 2-methyl-2-butene (2 mL), sodium dihydrogen phosphate (0.16 g), and sodium chlorite (0.32 g) were added. The mixture was stirred at rt for 1 h. It was then poured into ice-water and extracted with EtOAc. The combined organic solution was washed with brine, dried over MgSO$_4$. It was concentrated and dried to give 0.15 g of the acid. MS(AP$^+$) 369.1, (M+1)$^+$.

Part G:

The product from part F was dissolved in 15 mL of dry MeOH. The mixture was cooled in an ice-bath and HCl gas was bubbled in for 15 min. The cooling bath was removed and the mixture was sealed for 6.5 h. The solvent was then removed and the residue was dried under vacuum. The remaining solid was dissolved in MeOH (10 mL) and ammonium carbonate (0.40 g) was added. The mixture was sealed and stirred at rt for 12 h. It was concentrated and purified by reverse phase HPLC to give 25 mg of the desired product. MS (ES$^+$) 386.3, (M+1)$^+$. $^1$HNMR (DMSO, 300 MHz) δ (ppm): 8.75 (s, 2H), 8.38 (s, 2H), 7.90 (d, 1H), 7.65–7.00 (m, 9H), 6.40 (d, 1H), 4.25 (q, 2H), 3.38 (t, 2H), 2.75 (t, 2H), 1.95 (m, 2H).

Example 28

2-Benzyloxy-5-(5-carbamimidoyl-2,3-dihydro-indol-1-ylmethyl)-benzoic acid

Part A:

A solution of 5-formylsalicylic acid (1 g, 8.6 mmol) in DMF (15 mL) was treated with KHCO$_3$ (0.95 g, 1.1 eq) followed by benzyl bromide (1.12 mL, 1.1 eq) and the mixture was stirred overnight at rt under N$_2$. Water was added, and the mixture was extracted with EtOAc (3×). The combined extracts were washed with water (2×) and brine, dried over anh. Na$_2$SO$_4$, filtered and evaporated. Chromatography (silica gel, hexane/ethyl acetate 95/5) provided 34% of the desired dibenzylated product, plus 36% of the benzyl ester of the free phenol.

Part B:

Reductive amination of 5-cyanoindoline with the aldehyde prepared in Part A using the method described in Example 2, Part A above provided the alkylated indoline in 79% yield.

Part C:

The compound of Part B was converted into the title compound using the procedures described for Example 3, Parts F and G. $^1$HMR (300 MHz, DMSO-d6) δ 8.78 (s, 2H), 8.31 (s, 2H), 7.62–7.30 (9H, m), 7.18 (d, 1H, J=8.4 Hz); 6.75 (d, 1H, J=8.8 Hz); 5.19 (s, 2H), 4.45 (s, 2H), 3.52 (t, 2H, J=8 Hz), 3.02 (t, 2H, J=8 Hz). MS m/z 402.3 (M+H)$^+$.

Example 29

2-Benzyloxy-3-(5-carbamimidoyl-2,3-dihydro-indol-1-ylmethyl)-benzoic acid

The title compound was prepared as described for Example 28 substituting 3-formylsalicylic acid for 5-formylsalicylic acid in Part A. $^1$HMR (300 MHz, DMSO-d$_6$) δ 8.76 (s, 2H), 8.48 (s, 2H), 7.69 (d, 1H, J=7.6 Hz), 7.50 (4H, m), 7.37 (4H, m), 7.20 (t, 1H, J=7.6 Hz), 6.50 (d, 1H, J=8.8 Hz), 5.01 (s, 2H), 4.46 (s, 2H), 3.53 (t, 2H, J=8.5 Hz), 3.03 (t, 2H, J=8.5 Hz). MS m/z 402.3 (M+H)$^+$.

Example 68

2'-(5-Carbamimidoyl-2,3-dihydro-indol-1-ylmethyl)-4-methyl-5'-[(pyridin-2-ylmethyl)-carbamoyl]-biphenyl-2-carboxylic acid

Part A

The compound of Example 13, Part A (2 g., 7.38 mmol) was dissolved in $CCl_4$ (25 ml) and N-bromosuccinimide (1.4 g, 8.12 mmol) and benzoyl peroxide (0.01 g, 0.369 mmol) were added. The mixture was kept under a sunlamp with stirring in an 80° C. oil bath under nitrogen overnight. Reaction was then diluted with $CH_2Cl_2$, washed with water and brine, then dried over anhydrous $Na_2SO_4$, filtered and evaporated. The desired bromide was obtained after flash chromatography (silica gel, hexane/EtOAc 9:1) as a foam (2.06 g, 90%).

Part B

A solution of 5-cyanoindole (0.83 g., 5.82 mmol) in DMF (15 ml) was cooled in an ice bath and treated with NaH (60% in oil, 0.25 g, 6.34 mmol) followed by addition of the compound of Example 69, Part A (2.3 g, 5.29 mmol). The mixture was stirred at 0° C. to room temperature overnight. Reaction mixture was quenched by addition of water and product extracted into EtOAc (3×). Combined extracts were washed with brine, dried and evaporated. Trituration of the residue with $CH_2Cl_2$ provided the product as a white solid. (1.66 g, 79%).

Part C

A solution of 2-iodo-5-methylbenzoic acid (2 g., 7.6 mmol) in 20 ml DMF was treated with $KHCO_3$ (0.92 g., 9.2 mmol) and then benzyl bromide (1.1 ml, 9.2 mmol). The resulting mixture was stirred overnight at room temperature under $N_2$. Reaction was poured into water and extracted 3× with EtOAc. Combined extracts were washed with sat'd. $NaHCO_3$ and brine, dried over anh.$Na_2SO_4$, filtered and evaporated. Flash chromatography gave the pure benzyl ester (2.62 g, 98%) as a colorless liquid.

Part D

A mixture of the compound of Part C (2.6 g, 7.38 mmol), bis(pinacolato)boron (2.02 g, 7.97 mmol), KOAc (2.17 g, 22.1 mmol) and palladium acetate (49.7 mg, 0.221 mmol) in DMF 40 ml) was degassed and then heated with stirring for 2 h in an 85° C. oil bath under $N_2$. Reaction was cooled to room temperature then poured into 10 volumes of water and extracted 3× with EtOAc. Combined extracts were filtered through a pad of Celite then washed with water (3×) and brind, dried and evaporated. Flash chromatography (hexane/EtOAc 9:1) provided the boronate (1.5 g, 58%) as a white crystalline solid.

Part E

A mixture of the compound of Part B (0.96 g, 2.34 mmol) and the compound of Part D (0.98 g, 2.81 mmol) in a mixture of 15 ml toluene and 6 ml ethanol was purged with $N_2$ for 10 min followed by addition of 3 ml of a 2M $Na_2CO_3$ solution (2.5 eq) and tetrakis(triphenylphosphine)palladium (0.11 g., 0.094 mmol). The mixture was purged with $N_2$ (2×) then heated overnight in 95° C. oil bath under $N_2$. Reaction was evaporated to remove solvents then partitioned between water and EtOAc. Organic layer was washed with brine, dried and evaporated. Flash chromatography (hexane/EtOAc 9:1) provided the product (1.29 g, 92%) as a light yellow foam.

Part F

The compound of Part E (1.2 g, 2.16 mmol) was dissolved in 10 ml TFA and cooled to 0° C. Triethylsilane (1.0 ml, 6.48 mmol) was added and the mixture was stirred for 3 h at 0° C. Solvent was removed in vacuo and the indoline acid isolated by Flash Chromatography (1.01 g, 93%).

Part G

A mixture of the compound of Part F (200 mg, 0.398 mmol), 2-aminomethylpyridine (65 mg, 0.598 mmol), N-methylmorpholine (0.26 ml, 2.39 mmol), and Castro's reagent (0.26 g, 0.598 mmol) in 2 ml DMF was stirred under $N_2$ at room temperature for 3 days. Reaction was poured into water and extracted 3× with EtOAc. Extracts were combined, washed with water and brine, dried over $Na_2SO_4$, filtered and evaporated. Flash Chromatography (hexane/EtOAc 2:1) provided the amide (0.197 g, 86%).

Part H

A mixture of the compound from Part G (0.197 g, 0.333 mmol), hydroxylamine hydrochloride (0.139 g, 2.00 mmol) and triethylamine (0.28 ml, 2.00 mmol) in 8 ml EtOH was heated under reflux in a 95° C. oil bath for 5 h then cooled to room temperature and evaporated to dryness. Prep C18 HPLC provided the amidoxime product (0.21 g, 75%). Amidoxime was reduced to the amidine with simultaneous removal of the benzyl ester by transfer hydrogenation. The amidoxime was dissolved in 10 mL EtOH and treated with 28 μL HOAc followed by 1.5 ml cyclohexene and 50 mg palladium hydroxide. The resulting mixture was stirred at reflux for 5 h. Catalyst was removed by filtration and filtrate concentrated. The crude was treated with triethylsilane in TFA and then chromatographed by reverse phase HPLC to give the title compound as its tris TFA salt. in 62% yield. $^1$HNMR (500 MHz, DMSO-d$_6$) 9.15 (m, 1H0, 8.75 (s, sH), 8.54 (m, 1H), 8.34 (s, 2H), 7.85 (m, 2H), 7.74 (s, 1H), 7.67 (s, 1H), 7.46 (m, 3H), 7.37 (m, 4H), 7.21 (m, 1H), 6.20 (m, 1H), 4.58 (m, 2H), 4.20 (m, 2H), 3.45 (m, 2H), 2.98 (m, 2H), 2.38 (s, 3H). HRMS calcd. for: $C_{31}H_{30}N_5O_3$: 520.2349. Found: 520.2361.

Example 81

2'-(3-Benzyl-5-carbamimidoyl-indol-1-ylmethyl)-4-methyl-5'-methylcarbamoyl-biphenyl-2-carboxylic acid

Part A

The compound of Example 19, Part B (1.4 g, 6.23 mmol) was dissolved in 15 ml DMF and cooled in ice bath. To the cold solution was added sodium hydride (60% in oil, 0.18 g., 7.47 mmol) followed by the compound of Example 69, Part A (2.55 g, 6.23 mmol), and the resulting mixture was stirred for 1 h at 0° C. then overnight at room temperature. Work-up and chromatography provided the desired alkylated product (2.3 g, 74%).

Part B

The compound of Part A (1 g, 2.0 mmol) was dissolved in methylene chloride (2 ml) and treated with trifluoroacetic acid (2 ml) followed by stirring overnight at room temperature. Solvents were then removed in vacuo to provide the deprotected acid which was redissolved in 10 ml DMF and methylamine hydrochloride (0.27 g, 4.0 mmol), N-methylmorpholine (1.74 ml, 16.0 mmol) and Castro's reagent (1.3 g, 3.0 mmol) were added. The mixture was stirred under $N_2$ overnight. Work-up and chromatography provided the N-methylamide (0.78 g, 86%).

Part C

The compound of Part B was coupled to the compound of Example 68, Part D using the procedure described in Example 68, Part E to provide the biaryl product in 92% yield after chromatography.

Part D

A mixture of the compound of Part C (12.4 mg, 0.15 mmol), hydroxylamine hydrochloride (64 mg, 9.2 mmol) and triethylamine (0.13 ml, 0.92 mmol) in 5 mL EtOH was heated at reflux in 95 CC oil bath overnight. Solvents were removed in vacuo and residue purified by reverse phase HPLC to provide the amidoxime (87.4 mg, 90%). This intermediate was redissolved in 5 ml EtOH and 15.8 μL HOAc, 0.84 μL cyclohexene and 20 mg palladium hydroxide were added. The resulting mixture was heated at reflux in 95° C. oil bath for 5 h, then cooled to room temperature. Catalyst was removed by filtration and filtrate evaporated. Residue was purified by reverse phase HPLC to provide the title compound as its TFA salt. (56.4 mg, 64%).

Example 107

3-{2-(5-Carbamimidoyl-2,3-dihydro-indol-1-ylmethyl)-5-[(pyridin-2-ylmethyl)-carbamoyl]-phenyl}-6-methoxy-pyridine-2-carboxylic acid Part A Sodium hydride (60% inoil, 0.45 g, 11.3 mmol) was suspended in 15 ml DMF and cooled to 0° C. in an ice bath with stirring under $N_2$. To this was added 5-cyanoindole (1.5 g., 10.6 mmol) and the mixture was stirred for 20–30 min until a homogeneous solution was obtained, followed by addition of a solution of the compound of Example 68, Part A in 5 ml DMF. Stirring was continued from 0° C. to room temperature overnight. Reaction was diluted with water and extracted with EtOAc. Extracts were combined, washed with water and brine, dried and evap. Solid residue was suspended in $CH_2Cl_2$, collected by filtration and washed with hexane to provide the alkylated product (3.2 g, 74%) as an off-white powder.

Part B

The compound of Part A (0.68 g, 1.6 mmol) was suspended in 4 ml $CH_2Cl_2$ and 4 ml TFA was added at 0° C. The mixture was stirred at room temperature overnight, then stripped to dryness. A mixture of the resulting acid, 2-aminomethylpyridine (0.27 g, 2.49 mmol), N-methylmorpholine (1.1 ml, 9.95 mmol) and 0.9 g Castro's reagent (2.0 mmol) in 5 ml DMF was stirred at room temperature overnight. Work-up and flash chromatography provided the amide (0.54 g, 77%) as a white solid.

Part C

A mixture of the compound of Part B (0.1 g, 0.225 mmol), (2-formyl-6-methoxy3-pyridyl)tributylstannane (WO02/42273; 0.14 g, 0.338 mmol), CuO (18 mg, 0.225 mmol), and bis(triphenylphosphine) palladium dichloride (11 mg, 0.016 mmol) in 2 ml DMF was heated in a sealed tube for 1 h at 110° C. and then 2 h at 130° C. in microwave reactor. Workup and chromatography provide the coupled product (98 mg, 89%).

Part D

The compound of Part C was oxidized to the corresponding acid in 93% yield using the procedure of Example 12, Part B.

Part E

The compound of Part C was converted into the target amidine using the procedure of Example 2, Part B.

Part F

A solution of the compound of Part E in 1 ml TFA was cooled to 0° C. and treated with triethylsilane (3 eq.) and then stirred for 3 h while slowly warming to room temperature then stirred overnight. An addition portion of triethylsilane was then added and mix stirred overnight. Stripped to dryness and purified by reverse phase HPLC to provide the title compound. HRMS calc for $C_{30}H_{29}N_6O_4$: 537.2250. Found: 537.2236.

Example 114

2'-(5-aminomethyl-3-benzyl-indol-1-ylmethyl)-4-methyl-5'-methylcarbamoyl-biphenyl-2-carboxylic acid The compound of Example 92, Part C (84.4 mg) was dissolved in 5 ml EtOH and 0.5 ml TFA and 30 mg 10% Pd/C were added. The mixture was kept under a balloon of H2 overnight. Catalyst was removed by filtration and filtrate evaporated. Reverse phase HPLC provided the title compound (59.3 mg, 67%). HRMS calcd for $C_{33}H_{32}N_3O_3$: 540.2263. Found: 540.2286. $^1$H NMR (500 MHz, DMSO-$d_6$) δ ppm 2.41 (s, 3H) 2.71 (m, 3H) 4.02 (m, 4H) 5.12 (m, 2H) 6.45 (d, J=7.70 Hz, 1H) 7.09 (m, 2H) 7.17 (m, 3H) 7.26 (m, 4H) 7.42 (d, J=7.70 Hz, 1H) 7.54 (s, 1H) 7.59 (m, 2H) 7.80 (s, 1H) 8.01 (m, J=6.60 Hz, 2H) 8.34 (s, 1H) 12.86 (s, 1H).

Other examples were also prepared by following the procedures described above. Tables 1–3 below provide examples of the prepared compounds in the present invention.

TABLE 1

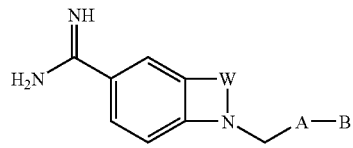

(Ic)

| Ex | W | A | B | MS (M + 1) |
|----|---|---|---|------------|
| 1 | $CH_2CH_2$ | 1,2-phenylene | 2-$CO_2$H-phenyl | 372.3 |
| 2 | $CH_2CH_2$ | 1,2-phenylene | 2,4-$(CO_2H)_2$-phenyl | 416.2 |
| 3 | $CH_2CH_2$ | 1,2-phenylene | 2-$CO_2$H-4-C(O)NH(i-Bu)-phenyl | 471.2 |

TABLE 1-continued (Ic)

| Ex | W | A | B | MS (M + 1) |
|---|---|---|---|---|
| 4 | CH$_2$CH$_2$ | 1,2-phenylene | 2-CO$_2$H-4-OMe-phenyl | 402.2 |
| 5 | CH$_2$CH$_2$ | 1,2-phenylene | 2-CO$_2$H-4-NHAc-phenyl | 429.2 |
| 6 | CH$_2$CH$_2$ | 4-OMe-1,2-phenylene | 2-CO$_2$H-phenyl | 402.2 |
| 7 | CH$_2$CH$_2$ | 1,2-phenylene | 2-CO$_2$H-4-CONH$_2$-phenyl | 415.2 |
| 8 | CH$_2$CH$_2$ | 1,3-phenylene | 2-CO$_2$H-phenyl | 372.2 |
| 9 | CH$_2$CH$_2$ | 1,3-phenylene | 2,4-(CO$_2$H)$_2$-phenyl | 416.2 |
| 10 | CH$_2$CH$_2$ | 1,3-phenylene | 2-SO$_2$NH$_2$-phenyl | 407.2 |
| 11 | CH$_2$CH$_2$ | 1,2-phenylene | 3-CH$_2$(CO$_2$H)-phenyl | 386.4 |
| 12 | CH$_2$CH$_2$ | 5-NHAc-1,2-phenylene | 2-CO$_2$H-phenyl | 429.2 |
| 13 | CH$_2$CH$_2$ | 5-CONH(phenethyl)-1,2-phenylene | 2-CO$_2$H-phenyl | 519.2 |
| 14 | CH$_2$CH$_2$ | 5-CONH(benzyl)-1,2-phenylene | 2-CO$_2$H-phenyl | 505.2 |
| 15 | CH$_2$CH$_2$ | 5-CONH(phenylpropyl)-1,2-phenylene | 2-CO$_2$H-phenyl | 532.2 |
| 16 | CH$_2$CH$_2$ | 5-CONH[2-(2-pyridyl)-ethyl]-1,3-phenylene | 2-CO$_2$H-phenyl | |
| 17 | CH$_2$CH$_2$ | 5-CONH(phenethyl)-1,2-phenylene | 2-CO$_2$H-4-OMe-phenyl | 549.4 |
| 17a | CH$_2$CH$_2$ | 5-CONH(3-Cl-phenethyl)-1,2-phenylene | 2-CO$_2$H-4-OMe-phenyl | 583.4 |
| 18 | CH=CH | 1,2-phenylene | 2-CO$_2$H-phenyl | 370.3 |
| 19 | C(benzyl)=CH | 1,2-phenylene | 2-CO$_2$H-4-OMe-phenyl | 490.2 |
| 20 | C(benzyl)=CH | 5-CONH(phenethyl)-1,2-phenylene | 2-CO$_2$H-4-OMe-phenyl | 637.0 |
| 21 | CH(benzyl)CH$_2$ | 1,2-phenylene | 2-CO$_2$H-4-OMe-phenyl | 492.3 |
| 22 | CH(benzyl)CH$_2$ | 5-CONH(phenethyl)-1,2-phenylene | 2-CO$_2$H-4-OMe-phenyl | |
| 23 | —(CH$_2$)$_3$— | 1,2-phenylene | 2-CO$_2$H-phenyl | 386.3 |
| 24 | CH$_2$CH$_2$ | 5-CONH(phenethyl)-1,2-phenylene | 2-CO$_2$H-phenyl | 519.2 |
| 25 | CH$_2$CH$_2$ | 5-CONH(benzyl)-1,2-phenylene | 2-CO$_2$H-phenyl | 505.1 |
| 26 | CH$_2$CH$_2$ | 5-CONH(phenethyl)-1,2-phenylene | 2-CO$_2$H-4-OMe-phenyl | |
| 27 | CH$_2$CH$_2$ | 5-CONH(benzyl)-1,2-phenylene | 2-CO$_2$H-4-OMe-phenyl | 535.1 |
| 30 | CH$_2$CH$_2$ | 4-Me-1,2-phenylene | 2-CO$_2$H-4-OMe-phenyl | 416.3 |
| 31 | CH=CH | 4-Me-1,2-phenylene | 2-CO$_2$H-4-OMe-phenyl | 414.2 |
| 32 | C(benzyl)=CH | 4-Me-1,2-phenylene | 2-CO$_2$H-4-OMe-phenyl | 504.2 |
| 33 | CH(benzyl)CH$_2$ | 4-Me-1,2-phenylene | 2-CO$_2$H-4-OMe-phenyl | 506.3 |
| 34 | CH=CH | 5-CONH[2-(2-pyridyl)-ethyl]-1,2-phenylene | 2-CO$_2$H-4-OMe-phenyl | 584.2 |
| 35 | CH$_2$CH$_2$ | 1,2-phenylene | 2-CO$_2$H-4-OEt-phenyl | 416.0 |
| 36 | CH$_2$CH$_2$ | 1,2-phenylene | 2-CO$_2$H-4-F-phenyl | 396.2 |
| 37 | CH=CH | 5-CONH[benzyl]-1,2-phenylene | 2-CO$_2$H-4-OMe-phenyl | 533.5 |
| 38 | C(benzyl)=CH | 4-amidino-1,2-phenylene | 2-CO$_2$H-4-OMe-phenyl | 532.3 |
| 39 | CH$_2$CH$_2$ | 5-NHCObenzyl-1,2-phenylene | 2-CO$_2$H-4-OMe-phenyl | 535.3 |
| 40 | CH=CH | 1,2-phenylene | 2-CO$_2$H-4-OMe-phenyl | 400.2 |
| 41 | C(benzyl)=CH | 5-CO$_2$H-1,2-phenylene | 2-CO$_2$H-4-OMe-phenyl | 531.9 |
| 42 | CH$_2$CH$_2$ | 1,2-phenylene | 2-CO$_2$H-4,5-diOMe-phenyl | 432.2 |
| 43 | CH$_2$CH$_2$ | 1,2-phenylene | 2-CO$_2$H-4-Me-phenyl | 386.2 |
| 44 | CH=CH | 5-CONH(3-Cl-phenethyl)-1,2-phenylene | 2-CO$_2$H-4-OMe-phenyl | 581.1 |
| 45 | CH$_2$CH$_2$ | 5-CO$_2$H-1,2-phenylene | 2-CO$_2$H-4-OMe-phenyl | 446.2 |
| 46 | CH=CH | 1,2-phenylene | 2-CO$_2$H-4-CONH$_2$-phenyl | 413.1 |
| 47 | C(benzyl)=CH | 4-aminomethyl-1,2-phenylene | 2-CO$_2$H-4-OMe-phenyl | 519.3 |
| 48 | C(benzyl)=CH | 4-acetoamidomethyl-1,2-phenylene | 2-CO$_2$H-4-OMe-phenyl | 561.5 |
| 49 | CH(benzyl)CH$_2$ | 4-amidino-1,2-phenylene | 2-CO$_2$H-4-OMe-phenyl | 534.5 |
| 50 | CH$_2$CH$_2$ | 5-CONHPr-1,2-phenylene | 2-CO$_2$H-4-OMe-phenyl | 487.0 |
| 51 | CH=CH | 5-CONHPr-1,2-phenylene | 2-CO$_2$H-4-OMe-phenyl | 485.1 |
| 52 | C(3,5-diMe-benzyl)=CH | 1,2-phenylene | 2-CO$_2$H-4-OMe-phenyl | 518.3 |
| 53 | CH(benzyl)CH$_2$ | 4-aminomethyl-1,2-phenylene | 2-CO$_2$H-4-OMe-phenyl | 521.3 |
| 54 | CH(3,5-diMe-benzyl)CH$_2$ | 1,2-phenylene | 2-CO$_2$H-4-OMe-phenyl | 520.3 |
| 55 | CH=CH | 5-CONH(CH$_2$CO$_2$H)-1,2-phenylene | 2-CO$_2$H-4-OMe-phenyl | 500.9 |
| 56 | CH$_2$CH$_2$ | 5-CONH(CH$_2$CO$_2$H)-1,2-phenylene | 2-CO$_2$H-4-OMe-phenyl | 502.9 |
| 57 | CH=CH | 1,2-phenylene | 2,5-diCO$_2$H-phenyl | 414.2 |
| 58 | CH$_2$CH$_2$ | 1,2-phenylene | 2,5-diCO$_2$H-phenyl | 416.2 |
| 59 | CH$_2$CH$_2$ | 5-CONHbenzyl-1,2-phenylene | 2-CO$_2$H-4-Me-phenyl | 517.0 |
| 60 | CH$_2$CH$_2$ | 1,2-phenylene | 2-CO$_2$H-4-CF$_3$-phenyl | 440.3 |
| 61 | CH=CH | 1,2-phenylene | 2,5-diCO$_2$H-4-OMe-phenyl | 444.0 |
| 62 | CH$_2$CH$_2$ | 5-CONHPr-1,2-phenylene | 2-CO$_2$H-4-Me-phenyl | 471.3 |
| 63 | CH$_2$CH$_2$ | 5-CONHcyclohexylmethyl-1,2-phenylene | 2-CO$_2$H-4-Me-phenyl | 525.4 |
| 64 | CH=CH | 6-amino-2,3-pyridylene | 2-CO$_2$H-4-Me-phenyl | 416.3 |
| 65 | CH$_2$CH$_2$ | 6-amino-2,3-pyridylene | 2-CO$_2$H-4-Me-phenyl | 418.3 |
| 66 | C(benzyl)=CH | 5-CONH$_2$-1,2-phenylene | 2-CO$_2$H-4-OMe-phenyl | 533.4 |

TABLE 1-continued

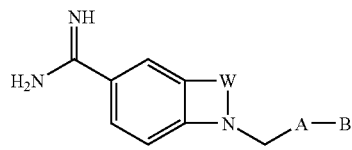

(Ic)

| Ex | W | A | B | MS (M + 1) |
|---|---|---|---|---|
| 67 | C(benzyl)=CH | 5-CONHMe-1,2-phenylene | 2-CO$_2$H-4-OMe-phenyl | 546.9 |
| 68 | CH$_2$CH$_2$ | 5-CONH[(2-pyridyl)-methy]-1,2-phenylene | 2-CO$_2$H-4-Me-phenyl | 520.2 |
| 69 | CH$_2$CH$_2$ | 5-NHCO(i-Bu)-1,2-phenylene | 2-CO$_2$H-4-OMe-phenyl | 501.2 |
| 70 | CH=CH | 5-CONHbenzyl-1,2-phenylene | 2-CO$_2$H-4-Me-phenyl | 514.4 |
| 71 | C(CONHMe)=CH | 1,2-phenylene | 2-CO$_2$H-4-OMe-phenyl | 457.3 |
| 72 | C(CONHPh)=CH | 1,2-phenylene | 2-CO$_2$H-4-OMe-phenyl | 519.4 |
| 73 | CH$_2$CH$_2$ | 5-CONH(3,5-diOMe-benzyl)-1,2-phenylene | 2-CO$_2$H-4-OMe-phenyl | 595.3 |
| 74 | CH$_2$CH$_2$ | 5-CONHCH$_2$-(1-naphthyl)-1,2-phenylene | 2-CO$_2$H-4-OMe-phenyl | 585.3 |
| 75 | CH$_2$CH$_2$ | 5-CONH(CH$_2$CH$_2$CO$_2$H)-1,2-phenylene | 2-CO$_2$H-4-OMe-phenyl | 517.2 |
| 76 | CH$_2$CH$_2$ | 1,2-phenylene | 2,5-diCO$_2$H-4-OMe-phenyl | 446.0 |
| 77 | CH$_2$CH$_2$ | 5-CONH(4-MeO-benzyl)-1,2-phenylene | 2-CO$_2$H-4-OMe-phenyl | 565.4 |
| 78 | C(CH$_2$OH)=CH | 1,2-phenylene | 2-CO$_2$H-4-OMe-phenyl | 430.1 |
| 79 | CH$_2$CH$_2$ | 5-CONH(cyclopropylmethyl)-1,2-phenylene | 2-CO$_2$H-4-OMe-phenyl | 499.4 |
| 80 | CH$_2$CH$_2$ | 5-CONH-(4-Cl-benzyl)-1,2-phenylene | 2-CO$_2$H-4-OMe-phenyl | 569.4 |
| 81 | C(benzyl)=CH | 5-CONHMe-1,2-phenylene | 2-CO$_2$H-4-Me-phenyl | 531.4 |
| 82 | C(benzyl)=CH | 5-CONHMe-1,2-phenylene | 2-CO$_2$H-4-CONH$_2$-phenyl | 560.4 |
| 83 | C(benzyl)=CH | 1,2-phenylene | 2,5-diCO$_2$H-4-OMe-phenyl | 534.4 |
| 84 | C(benzyl)=CH | 5-CONHMe-1,2-phenylene | 2,5-diCO$_2$H-4-OMe-phenyl | 591.4 |
| 85 | CH$_2$CH$_2$ | 5-CO(1-morpholino)-1,2-phenylene | 2-CO$_2$H-4-OMe-phenyl | 515.2 |
| 86 | CH$_2$CH$_2$ | 5-CO[4-(2-OMe-ethyl)-1-piperdinyl]-1,2-phenylene | 2-CO$_2$H-4-OMe-phenyl | 572.3 |
| 87 | CH$_2$CH$_2$ | 5-CONH(i-Bu)-1,2-phenylene | 2-CO$_2$H-4-OMe-phenyl | 501.4 |
| 88 | CH$_2$CH$_2$ | 5-CONHisoamyl-1,2-phenylene | 2-CO$_2$H-4-OMe-phenyl | 515.3 |
| 89 | CH$_2$CH$_2$ | 5-CONH[(3-pyridyl)-methyl]-1,2-phenylene | 2-CO$_2$H-4-OMe-phenyl | 536.2 |
| 90 | CH$_2$CH$_2$ | 5-CONHCH$_2$(4-tetrahydropyranyl)-1,2-phenylene | 2-CO$_2$H-4-OMe-phenyl | 543.3 |
| 91 | CH$_2$CH$_2$ | 5-CO[4-(2-CO$_2$Et-ethyl)-1-piperdinyl]-1,2-phenylene | 2-CO$_2$H-4-OMe-phenyl | 600.5 |
| 92 | CH=CH | 1,2-phenylene | 2,6-diCO$_2$H-4-OMe-phenyl | 444.0 |
| 93 | CH$_2$CH$_2$ | 5-(S)-CONHCH(Me)phenyl-1,2-phenylene | 2-CO$_2$H-4-OMe-phenyl | 549.3 |
| 94 | CH$_2$CH$_2$ | 5-(R)-CONHCH(Me)phenyl-1,2-phenylene | 2-CO$_2$H-4-OMe-phenyl | 549.3 |
| 95 | CH$_2$CH$_2$ | 5-CONHCH$_2$(1-indanyl)-1,2-phenylene | 2-CO$_2$H-4-OMe-phenyl | |
| 96 | C(benzyl)=CH | 5-CONHEt-1,2-phenylene | 2-CO$_2$H-4-OMe-phenyl | 561.4 |
| 97 | C(benzyl)=CH | 5-CONHPr-1,2-phenylene | 2-CO$_2$H-4-OMe-phenyl | 575.4 |
| 98 | C(benzyl)=CH | 5-CONHcyclopropylmethyl-1,2-phenylene | 2-CO$_2$H-4-OMe-phenyl | 587.4 |
| 99 | C(benzyl)=CH | 5-CONH(i-Bu)-1,2-phenylene | 2-CO$_2$H-4-OMe-phenyl | 591.4 |
| 100 | CH$_2$CH$_2$ | 5-CONH(3-OH—Pr)-1,2-phenylene | 2-CO$_2$H-4-OMe-phenyl | 503.4 |
| 101 | CH$_2$CH$_2$ | 5-CONHMe-1,2-phenylene | 2-CO$_2$H-4-OMe-phenyl | 459.3 |
| 102 | CH$_2$CH$_2$ | 5-CONH(3-CO$_2$H—Pr)-1,2-phenylene | 2-CO$_2$H-4-OMe-phenyl | 531.4 |
| 103 | CH$_2$CH$_2$ | 5-CO[4-(2-HO-ethyl)-1-piperdinyl]-1,2-phenylene | 2-CO$_2$H-4-OMe-phenyl | 558.5 |
| 104 | CH$_2$CH$_2$ | 5-CONH(N,N-dimethylaminoethyl)-1,2-phenylene | 2-CO$_2$H-4-OMe-phenyl | |
| 105 | C(benzyl)=CH | 5-CONHMe-1,2-phenylene | 3-CO$_2$H-4-OMe-phenyl | 547.4 |
| 106 | C(4-CO$_2$H-benzyl)=CH | 5-CONHMe-1,2-phenylene | 2-CO$_2$H-4-OMe-phenyl | 591.3 |
| 107 | CH$_2$CH$_2$ | 5-CONHCH$_2$(2-pyridyl)-1,2-phenylene | 2-CO$_2$H-6-OMe-3-pyridyl | 537.1 |
| 108 | C(CH$_2$CONHMe)=CH | 5-CONHMe-1,2-phenylene | 2-CO$_2$H-4-OMe-phenyl | 528.2 |
| 109 | CH$_2$CH$_2$ | 5-CONHCH$_2$(2-pyridyl)-1,2-phenylene | 2-CO$_2$H-phenyl | 506.1 |
| 110 | CH$_2$CH$_2$ | 1,3-phenylene | 2-CO$_2$H-4-CONH$_2$-phenyl | 415.2 |
| 111 | CH=CH | 5-CONHCH$_2$(2-pyridyl)-1,2-phenylene | 3-CO$_2$H-4-pyridyl | 505.1 |
| 115 | C(benzyl)=CH | 5-CONMe$_2$-1,2-phenylene | 2-CO$_2$H-4-OMe-phenyl | 561.3 |

TABLE 2

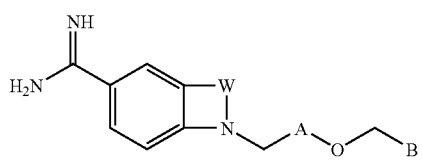

(Ic)

| Ex | W | A | B | MS (M + 1) |
|---|---|---|---|---|
| 28 | CH$_2$CH$_2$ | 3-CO$_2$H-1,4-phenylene | phenyl | 402.3 |
| 29 | CH$_2$CH$_2$ | 3-CO$_2$H-1,2-phenylene | phenyl | 402.2 |

TABLE 3

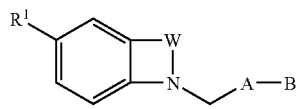

| Ex | R¹ | W | A | B | MS (M + 1) |
|---|---|---|---|---|---|
| 112 | CONH$_2$ | CH$_2$CH$_2$ | 5-CONH(3-Cl-phenethyl)-1,2-phenylene | 2-CO$_2$H-4-OMe-phenyl | 584.2 |
| 113 | CONH$_2$ | CH$_2$CH$_2$ | 5-CONHbenzyl-1,2-phenylene | 2-CO$_2$H-4-OMe-phenyl | 536.1 |
| 114 | CH$_2$NH$_2$ | C(benzyl)=CH | 5-CONHMe-1,2-phenylene | 2-CO$_2$H-4-Me-phenyl | 501.4 |

Utility

The compounds of this invention are inhibitors of factor XIa and are useful as anticoagulants for the treatment or prevention of thromboembolic disorders in mammals (i.e., factor XIa-associated disorders). In general, a thromboembolic disorder is a circulatory disease caused by blood clots (i.e., diseases involving fibrin formation, platelet activation, and/or platelet aggregation). The term "thromboembolic disorders" as used herein includes arterial cardiovascular thromboembolic disorders, venous cardiovascular or cerebrovascular thromboembolic disorders, and thromboembolic disorders in the chambers of the heart. The term "thromboembolic disorders" as used herein also includes specific disorders selected from, but not limited to, unstable angina or other acute coronary syndromes, first or recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, or (f) other procedures in which blood is exposed to an artificial surface that promotes thrombosis. It is noted that thrombosis includes occlusion (e.g., after a bypass) and reocclusion (e.g., during or after percutaneous transluminal coronary angioplasty). The thromboembolic disorders may result from conditions including but not limited to atherosclerosis, surgery or surgical complications, prolonged immobilization, arterial fibrillation, congenital thrombophilia, cancer, diabetes, effects of medications or hormones, and complications of pregnancy. The anticoagulant effect of compounds of the present invention is believed to be due to inhibition of serine proteases involved in the coagulation cascade and/or contact activation system, more specifically, inhibition of the coagulation factors: factor XIa, factor VIIa, factor IXa, factor Xa, plasma kallikrein or thrombin.

The compounds of this invention also are inhibitors of plasma kallikrein and are useful as anti-inflammatory agents for the treatment or prevention of diseases associated with an activation of the contact activation system (i.e., plasma kallikrein associated disorders). In general, a contact activation system disorder is a disease caused by activation of blood on artificial surfaces, including prosthetic valves or other implants, indwelling catheters, stents, cardiopulmonary bypass, hemodialysis, microorganism (e.g., bacteria, virus), or other procedures in which blood is exposed to an artificial surface that promotes contact activation, blood clots (i.e., diseases involving fibrin formation, platelet activation, and/or platelet aggregation). It also includes systemic inflammatory response syndrome, sepsis, acute respiratory dystress syndrome, hereditary angioedema or other inherited or aquired deficencies of contact activation components or their inhibitors (plasma kallikrein, factor XIIa, high molecular weight kininogen, C1-esterase inhibitor). It may also include acute and chronic inflammations of joints, vessels, or other mammalian organs.

The effectiveness of compounds of the present invention as inhibitors of the coagulation factors XIa, VIIa, IXa, Xa, plasma kallikrein or thrombin, can be determined using a relevant purified serine protease, respectively, and an appropriate synthetic substrate. The rate of hydrolysis of the chromogenic or fluorogenic substrate by the relevant serine protease was measured both in the absence and presence of compounds of the present invention. Hydrolysis of the substrate resulted in the release of pNA (para nitroaniline), which was monitored spectrophotometrically by measuring the increase in absorbance at 405 nm, or the release of AMC (amino methylcoumarin, which was monitored spectrofluorometrically by measuring the increase in emission at 460 nm with excitation at 380 nm. A decrease in the rate of absorbance or fluorescence change in the presence of inhibitor is indicative of enzyme inhibition. Such methods are known to one skilled in the art. The results of this assay are expressed as the inhibitory constant, $K_i$.

Factor XIa determinations were made in 50 mM HEPES buffer at pH 7.4 containing 145 mM NaCl, 5 mM KCl, and 0.1% PEG 8000 (polyethylene glycol; JT Baker or Fisher Scientific). Determinations were made using purified human Factor XIa at a final concentration of 75–200 pM (Haematologic Technologies) and the synthetic substrate S-2366 (pyroGlu-Pro-Arg-pNA; Chromogenix) at a concentration of 0.0002–0.00025 M. Compounds tested in the Factor XIa assay are considered to be active if they exhibit a $K_i$ of equal to or less than 15 μM. Preferred compounds of the present invention have $K_i$'s of equal to or less than 1 μM. More preferred compounds of the present invention have $K_i$'s of equal to or less than 0.1 μM. Even more preferred compounds of the present invention have $K_i$'s of equal to or less than 0.01 μM. Compounds of the present invention have demonstrated $K_i$ values of equal to or less than 15 μM in the assay for Factor XIa, thereby confirming the utility of the compounds of the present invention as effective inhibitors of coagulation Factor XIa.

Factor VIIa determinations were made in 0.005 M calcium chloride, 0.15 M sodium chloride, 0.05 M HEPES buffer containing 0.5% PEG 8000 at a pH of 7.4. Determinations were made using purified human Factor VIIa (Haematologic Technologies) or recombinant human Factor VIIa (Novo Nordisk) at a final assay concentration of 2–5 nM, recombinant soluble tissue factor at a concentration of 18–35 nM and the synthetic substrate H-D-Ile-Pro-Arg-pNA (S-2288; Chromogenix or BMPM-2; AnaSpec) at a concentration of 0.001 M. Compounds tested in the Factor VIIa assay are considered to be active if they exhibit a $K_i$ of equal to or less than 15 µM.

Factor IXa determinations were made in 0.005 M calcium chloride, 0.1 M sodium chloride, 0.05 M TRIS base and 0.5% PEG 8000 at a pH of 7.4. Determinations were made using purified human Factor IXa (Haematologic Technologies) at a final assay concentration of 20–100 nM and the synthetic substrate PCIXA2100-B (CenterChem) or Pefafluor IXa 3688 (H-D-Leu-Ph'Gly-Arg-AMC; CenterChem) at a concentration of 0.0004–0.0005 M. Compounds tested in the Factor IXa assay are considered to be active if they exhibit a $K_i$ of equal to or less than 15 µM.

Factor Xa determinations were made in 0.1 M sodium phosphate buffer at a pH of 7.4 containing 0.2 M sodium chloride and 0.5% PEG 8000. Determinations were made using purified human Factor Xa (Haematologic Technologies) at a final assay concentration of 150–1000 pM and the synthetic substrate S-2222 (Bz-Ile-Glu (gamma-OMe, 50%)-Gly-Arg-pNA; Chromogenix) at a concentration of 0.0002–0.0003 M. Compounds tested in the Factor Xa assay are considered to be active if they exhibit a $K_i$ of equal to or less than 15 µM.

Plasma kallikrein determinations were made in 0.1 M sodium phosphate buffer at a pH of 7.4 containing 0.2 M sodium chloride and 0.5% PEG 8000. Determinations were made using purified human kallikrein (Enzyme Research Laboratories) at a final assay concentration of 200 pM and the synthetic substrate S-2302 (H-(D)-Pro-Phe-Arg-pNA; Chromogenix) at a concentration of 0.00008–0.0004 M. The Km value used for calculation of $K_i$ was 0.00005 to 0.00007 M. Compounds tested in the plasma kallikrein assay are considered to be active if they exhibit a $K_i$ of equal to or less than 15 µM. Preferred compounds of the present invention have $K_i$'s of equal to or less than 1 µM. More preferred compounds of the present invention have $K_i$'s of equal to or less than 0.1 µM. Even more preferred compounds of the present invention have $K_i$'s of equal to or less than 0.01 µM. Compounds of the present invention have demonstrated $K_i$ values of equal to or less than 15 µM in the assay for plasma kallikrein, thereby confirming the utility of the compounds of the present invention as effective inhibitors of plasma kallikrein.

Thrombin determinations were made in 0.1 M sodium phosphate buffer at a pH of 7.4 containing 0.2 M sodium chloride and 0.5% PEG 8000. Determinations were made using purified human alpha thrombin (Haematologic Technologies or Enzyme Research Laboratories) at a final assay concentration of 200–250 µM and the synthetic substrate S-2366 (pyroGlu-Pro-Arg-pNA; Chromogenix) at a concentration of 0.0002 M. Compounds tested in the thrombin assay are considered to be active if they exhibit a $K_i$ of equal to or less than 15 µM.

Compounds of the present invention have demonstrated $K_j$ values of equal to or less than 15 µM in at least one of the above assays, thereby confirming the utility of the compounds of the present invention as effective inhibitors of the coagulation cascade and/or contact activation system, and useful as anticoagulants for the prevention or treatment of thromboembolic disorders in mammals and/or as anti-inflammatory agents for the prevention or treatment of inflammatory disorders in mammals.

The Michaelis constant, $K_m$, for substrate hydrolysis by each protease was determined at 25° C. using the method of Lineweaver and Burk. Values of $K_i$ were determined by allowing the protease to react with the substrate in the presence of the inhibitor. Reactions were allowed to go for periods of 20–180 minutes (depending on the protease) and the velocities (rate of absorbance or fluorescence change versus time) were measured. The following relationships were used to calculate $K_i$ values:

$(v_o - v_s)/v_s = I/(K_i(1+S/K_m))$ for a competitive inhibitor with one binding site; or $v_s/v_o = A + ((B-A)/1+((IC_{50}/(I)^n)))$ and
$K_i = IC_{50}/(1+S/K_m)$ for a competitive inhibitor where:

$v_o$ is the velocity of the control in the absence of inhibitor;

$v_s$ is the velocity in the presence of inhibitor;

I is the concentration of inhibitor;

A is the minimum activity remaining (usually locked at zero);

B is the maximum activity remaining (usually locked at 1.0);

n is the Hill coefficient, a measure of the number and cooperativity of potential inhibitor binding sites;

$IC_{50}$ is the concentration of inhibitor that produces 50% inhibition under the assay conditions;

$K_i$ is the dissociation constant of the enzyme:inhibitor complex;

S is the concentration of substrate; and $K_m$ is the Michaelis constant for the substrate.

The effectiveness of compounds of the present invention as inhibitors of the coagulation factors XIa, VIIa, IXa, Xa, or thrombin, can be determined using relevant in vivo thrombosis models, including In Vivo Electrically-induced Carotid Artery Thrombosis Models and In Vivo Rabbit Arterio-venous Shunt Thrombosis Models.

In Vivo Electrically-induced Carotid Artery Thrombosis Model:

The antithrombotic effect of compounds of the present invention can be demonstrated in the electrically-induced carotid artery thrombosis (ECAT) model in rabbits. In this model, rabbits are anesthetized with a mixture of ketamine (50 mg/kg i.m.) and xylazine (10 mg/kg i.m.). A femoral vein and a femoral artery are isolated and catheterized. The carotid artery is also isolated such that its blood flow can be measured with a calibrated flow probe that is linked to a flowmeter. A stainless steel bipolar hook electrode is placed on the carotid artery and positioned caudally in relationship to the flow probe as a means of applying electrical stimulus. In order to protect the surrounding tissue, a piece of Parafilm is placed under the electrode.

Test compounds are considered to be effective as anticoagulants based on their ability to maintain blood flow in the carotid artery following the induction of thrombosis by an electrical stimulus. A test compound or vehicle is given as continuous intravenous infusion via the femoral vein, starting 1 hour before electrical stimulation and continuing to the end of the test. Thrombosis is induced by applying a direct electrical current of 4 mA for 3 min to the external arterial surface, using a constant current unit and a d.c. stimulator. The carotid blood flow is monitored and the time to occlusion (decrease of blood flow to zero following induction of thrombosis) in minutes is noted. The change in observed blood flow is calculated as a percentage of the blood flow prior to induction of thrombosis and provides a measure of the effect of a test compound when compared to the case where no compound is administered. This information is used to estimate the $ED_{50}$ value, the dose that increases blood flow to 50% of the control (blood flow prior to induction of thrombosis) and is accomplished by nonlinear least square regression.

In Vivo Rabbit Arterio-venous Shunt Thrombosis Model:

The antithrombotic effect of compounds of the present invention can be demonstrated in a rabbit arterio-venous (AV) shunt thrombosis model. In this model, rabbits weighing 2–3 kg anesthetized with a mixture of xylazine (10 mg/kg i.m.) and ketamine (50 mg/kg i.m.) are used. A saline-filled AV shunt device is connected between the femoral arterial and the femoral venous cannulae. The AV shunt device consists of a piece of 6-cm tygon tubing that contains a piece of silk thread. Blood will flow from the femoral artery via the AV-shunt into the femoral vein. The exposure of flowing blood to a silk thread will induce the formation of a significant thrombus. After forty minutes, the shunt is disconnected and the silk thread covered with thrombus is weighed. Test agents or vehicle will be given (i.v., i.p., s.c., or orally) prior to the opening of the AV shunt. The percentage inhibition of thrombus formation is determined for each treatment group. The $ID_{50}$ values (dose which produces 50% inhibition of thrombus formation) are estimated by linear regression.

The anti-inflammatory effect of these compounds can be demonstrated in an Evans Blue dye extravasation assay using C1-esterase inhibitor deficient mice. In this model, mice are dosed with a compound of the present invention, Evans Blue is injected via the tail vein, and extravasation of the blue dye is determined by spectrophotometric means from tissue extracts.

The ability of the compounds of the current invention to reduce or prevent the systemic inflammatory response syndrome, for example, as observed during on-pump cardiovascular procedures, can be tested in in vitro perfusion systems, or by on-pump surgical procedures in larger mammals, including dogs and baboons. Read-outs to assess the benefit of the compounds of the present invention include for example reduced platelet loss, reduced platelet/white blood cell complexes, reduced neutrophil elastase levels in plasma, reduced activation of complement factors, and reduced activation and/or consumption of contact activation proteins (plasma kallikrein, factor XII, factor XI, high molecular weight kininogen, C1-esterase inhibitors).

The utility of the compounds of the current invention to reduce or prevent the morbidity and/or mortality of sepsis can be assessed by injecting a mammalian host with bacteria or viruses or extracts there of and compounds of the present invention. Typical read-outs of the efficacy include changes in the LD50 and blood pressure preservation.

The compounds of the present invention may also be useful as inhibitors of additional serine proteases, notably human thrombin, human plasma kallikrein and human plasmin. Because of their inhibitory action, these compounds are indicated for use in the prevention or treatment of physiological reactions, including blood coagulation, fibrinolysis, blood pressure regulation and inflammation, and wound healing catalyzed by the aforesaid class of enzymes. Specifically, the compounds have utility as drugs for the treatment of diseases arising from elevated thrombin activity of the aforementioned serine proteases, such as myocardial infarction, and as reagents used as anticoagulants in the processing of blood to plasma for diagnostic and other commercial purposes.

The compounds of the present invention can be administered alone or in combination with one or more additional therapeutic agents. These include other anti-coagulant or coagulation inhibitory agents, anti-platelet or platelet inhibitory agents, anti-inflammatory agents, thrombin inhibitors, or thrombolytic or fibrinolytic agents.

The compounds are administered to a mammal in a therapeutically effective amount. By "therapeutically effective amount" it is meant an amount of a compound of the present invention that, when administered alone or in combination with an additional therapeutic agent to a mammal, is effective to treat (i.e. prevent, inhibit or ameliorate) the thromboembolic and/or inflammatory disease condition or treat the progression of the disease in a host.

The compounds of the invention are preferably administered alone to a mammal in a therapeutically effective amount. However, the compounds of the invention can also be administered in combination with an additional therapeutic agent, as define below, to a mammal in a therapeutically effective amount. When administered in a combination, the combination of compounds is preferably, but not necessarily, a synergistic combination. Synergy, as described for example by Chou and Talalay, $Adv.\ Enzyme\ Regul.$ 1984, 22, 27–55, occurs when the effect (in this case, inhibition of the desired target) of the compounds when administered in combination is greater than the additive effect of the compounds when administered alone as a single agent. In general, a synergistic effect is most clearly demonstrated at suboptimal concentrations of the compounds. Synergy can be in terms of lower cytotoxicity, increased anticoagulant effect, or some other beneficial effect of the combination compared with the individual components.

By "administered in combination" or "combination therapy" it is meant that the compound of the present invention and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect.

Compounds which can be administered in combination with the compounds of the present invention include, but are not limited to, anticoagulants, anti-thrombin agents, anti-platelet agents, fibrinolytics, hypolipidemic agents, antihypertensive agents, and anti-ischemic agents.

Other anticoagulant agents (or coagulation inhibitory agents) that may be used in combination with the compounds of this invention include warfarin, heparin (either unfractionated heparin or any commercially available low molecular weight heparin, for example LOVANOX™), aprotinin, synthetic pentasaccharide, direct acting thrombin inhibitors including hirudin and argatroban, as well as other factor VIIa, VIIIa, IXa, Xa, XIa, thrombin, TAFI, and fibrinogen inhibitors known in the art.

The term anti-platelet agents (or platelet inhibitory agents), as used herein, denotes agents that inhibit platelet function, for example, by inhibiting the aggregation, adhesion or granular secretion of platelets. Such agents include, but are not limited to, the various known non-steroidal anti-inflammatory drugs (NSAIDS) such as aspirin, ibuprofen, naproxen, sulindac, indomethacin, mefenamate, droxicam, diclofenac, sulfinpyrazone, and piroxicam, including pharmaceutically acceptable salts or prodrugs thereof. Of the NSAIDS, aspirin (acetylsalicylic acid or ASA), and piroxicam are preferred. Other suitable platelet inhibitory agents include IIb/IIIa antagonists (e.g., tirofiban, eptifibatide, and abciximab), thromboxane-A2-receptor antagonists (e.g., ifetroban), thromboxane-A2-synthetase inhibitors, phosphodiesterase-III (PDE-III) inhibitors (e.g., dipyridamole, cilostazol), and PDE V inhibitors (such as sildenafil), and pharmaceutically acceptable salts or prodrugs thereof.

The term anti-platelet agents (or platelet inhibitory agents), as used herein, is also intended to include ADP (adenosine diphosphate) receptor antagonists, preferably antagonists of the purinergic receptors $P_2Y_1$ and $P_2Y_{12}$, with $P_2Y_{12}$ being even more preferred. Preferred $P_2Y_{12}$ receptor antagonists include ticlopidine and clopidogrel, including pharmaceutically acceptable salts or prodrugs thereof. Clopidogrel is an even more preferred agent. Ticlopidine and clopidogrel are also preferred compounds since they are known to be gentle on the gastro-intestinal tract in use. The compounds of the present invention may also be dosed in combination with aprotinin.

The term thrombin inhibitors (or anti-thrombin agents), as used herein, denotes inhibitors of the serine protease thrombin. By inhibiting thrombin, various thrombin-mediated processes, such as thrombin-mediated platelet activation (that is, for example, the aggregation of platelets, and/or the granular secretion of plasminogen activator inhibitor-I and/or serotonin), endothelial cell activation, inflammatory reactions, and/or fibrin formation are disrupted. A number of thrombin inhibitors are known to one of skill in the art and these inhibitors are contemplated to be used in combination with the present compounds. Such inhibitors include, but are not limited to, boroarginine derivatives, boropeptides, heparins, hirudin and argatroban, including pharmaceutically acceptable salts and prodrugs thereof. Boroarginine derivatives and boropeptides include N-acetyl and peptide derivatives of boronic acid, such as C-terminal alpha-aminoboronic acid derivatives of lysine, ornithine, arginine, homoarginine and corresponding isothiouronium analogs thereof. The term hirudin, as used herein, includes suitable derivatives or analogs of hirudin, referred to herein as hirulogs, such as disulfatohirudin.

The term thrombolytic (or fibrinolytic) agents (or thrombolytics or fibrinolytics), as used herein, denotes agents that lyse blood clots (thrombi). Such agents include tissue plasminogen activator (TPA, natural or recombinant) and modified forms thereof, anistreplase, urokinase, streptokinase, tenecteplase (TNK), lanoteplase (nPA), factor VIIa inhibitors, PAI-I inhibitors (i.e., inactivators of tissue plasminogen activator inhibitors), alpha-2-antiplasmin inhibitors, and anisoylated plasminogen streptokinase activator complex, including pharmaceutically acceptable salts or prodrugs thereof. The term anistreplase, as used herein, refers to anisoylated plasminogen streptokinase activator complex, as described, for example, in European Patent Application No. 028,489, the disclosure of which is hereby incorporated herein by reference herein. The term urokinase, as used herein, is intended to denote both dual and single chain urokinase, the latter also being referred to herein as prourokinase.

Examples of suitable anti-arrythmic agents for use in combination with the present compounds include: Class I agents (such as propafenone); Class II agents (such as carvadiol and propranolol); Class III agents (such as sotalol, dofetilide, amiodarone, azimilide and ibutilide); Class IV agents (such as ditiazem and verapamil); K$^+$ channel openers such as $I_{Ach}$ inhibitors, and $I_{Kur}$ inhibitors (e.g., compounds such as those disclosed in WO01/40231).

The term antihypertensive agents, as used herein, include: alpha adrenergic blockers; beta adrenergic blockers; calcium channel blockers (e.g., diltiazem, verapamili nifedipine, amlodipine and mybefradil); diruetics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone); renin inhibitors; angiotensin-converting enzyme (ACE) inhibitors (e.g., captopril, lisinopril, fosinopril, enalapril, ceranopril, cilazopril, delapril, pentopril, quinapril, ramipril, lisinopril); angiotensin-II receptor antagonists (e.g., irbestatin, losartan, valsartan); ET receptor antagonists (e.g., sitaxsentan, atrsentan and compounds disclosed in U.S. Pat. Nos. 5,612,359 and 6,043,265); Dual ET/AII antagonist (e.g., compounds disclosed in WO 00/01389); neutral endopeptidase (NEP) inhibitors; vasopepsidase inhibitors (dual ACE/NEP inhibitors, e.g., omapatrilat, gemopatrilat, nitrates); and β-blockers (e.g., propanolol, nadolo, or carvedilol).

Examples of suitable cardiac glycosides for use in combination with the compounds of the present invention include digitalis and ouabain.

Examples of suitable mineralocorticoid receptor antagonists for use in combination with the compounds of the present invention include sprionolactone and eplirinone.

Examples of suitable cholesterol/lipid lowering agents and lipid profile therapies for use in combination with the compounds of the present invention include: HMG-CoA reductase inhibitors (e.g., pravastatin, lovastatin, atorvastatin, simvastatin, fluvastatin, NK-104 (a.k.a. itavastatin, or nisvastatin or nisbastatin) and ZD-4522 (a.k.a. rosuvastatin, or atavastatin or visastatin)); squalene synthetase inhibitors; fibrates; bile acid sequestrants (such as questran); ACAT inhibitors; MTP inhibitors; lipooxygenase inhibitors; choesterol absorption inhibitors; and cholesterol ester transfer protein inhibitors (e.g., CP-529414).

Examples of suitable anti-diabetic agents for use in combination with the compounds of the present invention include: biguanides (e.g., metformin); glucosidase inhibitors (e.g., acarbose); insulins (including insulin secretagogues or insulin sensitizers); meglitinides (e.g., repaglinide); sulfonylureas (e.g., glimepiride, glyburide and glipizide); biguanide/glyburide combinations (e.g., glucovance), thiozolidinediones (e.g., troglitazone, rosiglitazone and pioglitazone), PPAR-alpha agonists, PPAR-gamma agonists, PPAR alpha/gamma dual agonists, SGLT2 inhibitors, inhibitors of fatty acid binding protein (aP2) such as those disclosed in WO00/59506, glucagon-like peptide-1 (GLP-1), and dipeptidyl peptidase IV (DP4) inhibitors.

Examples of suitable anti-depressant agents for use in combination with the compounds of the present invention include nefazodone and sertraline.

Examples of suitable anti-inflammatory agents for use in combination with the compounds of the present invention include: prednisone; dexamethasone; enbrel; protein tyrosine kinase (PTK) inhibitors; cyclooxygenase inhibitors (including NSAIDs, and COX-1 and/or COX-2 inhibitors); aspirin; indomethacin; ibuprofen; prioxicam; naproxen; celecoxib; and/or rofecoxib.

Examples of suitable anti-osteoporosis agents for use in combination with the compounds of the present invention include alendronate and raloxifene.

Examples of suitable hormone replacement therapies for use in combination with the compounds of the present invention include estrogen (e.g., congugated estrogens) and estradiol.

Examples of suitable anti-obesity agents for use in combination with the compounds of the present invention include orlistat and aP2 inhibitors (such as those disclosed in WO00/59506).

Examples of suitable anti-anxiety agents for use in combination with the compounds of the present invention include diazepam, lorazepam, buspirone, and hydroxyzine pamoate.

Examples of suitable anti-anxiety agents for use in combination with the compounds of the present invention include diazepam, lorazepam, buspirone, and hydroxyzine pamoate.

Examples of suitable anti-proliferative agents for use in combination with the compounds of the present invention include cyclosporin A, paclitaxel, adriamycin; epithilones, cisplatin, and carboplatin.

Examples of suitable anti-ulcer and gastroesophageal reflux disease agents for use in combination with the compounds of the present invention include famotidine, ranitidine, and omeprazole.

Administration of the compounds of the present invention (i.e., a first therapeutic agent) in combination with at least one additional therapeutic agent (i.e., a second therapeutic agent), preferably affords an efficacy advantage over the compounds and agents alone, preferably while permitting the use of lower doses of each. A lower dosage minimizes the potential of side effects, thereby providing an increased margin of safety. It is preferred that at least one of the therapeutic agents is administered in a sub-therapeutic dose. It is even more preferred that all of the therapeutic agents be administered in sub-therapeutic doses. Sub-therapeutic is intended to mean an amount of a therapeutic agent that by itself does not give the desired therapeutic effect for the condition or disease being treated. Synergistic combination is intended to mean that the observed effect of the combination is greater than the sum of the individual agents administered alone.

The compounds of the present invention are also useful as standard or reference compounds, for example as a quality standard or control, in tests or assays involving the inhibition of thrombin, Factor VIIa, IXa, Xa, XIa, and/or plasma kallikrein. Such compounds may be provided in a commercial kit, for example, for use in pharmaceutical research involving thrombin, Factor VIIa, IXa, Xa, XIa, and/or plasma kallikrein. XIa. For example, a compound of the present invention could be used as a reference in an assay to compare its known activity to a compound with an unknown activity. This would ensure the experimentor that the assay was being performed properly and provide a basis for comparison, especially if the test compound was a derivative of the reference compound. When developing new assays or protocols, compounds according to the present invention could be used to test their effectiveness.

The compounds of the present invention may also be used in diagnostic assays involving thrombin, Factor VIIa, IXa, Xa, XIa, and/or plasma kallikrein. For example, the presence of thrombin, Factor VIIa, IXa, Xa XIa, and/or plasma kallikrein in an unknown sample could be determined by addition of the relevant chromogenic substrate, for example S2366 for Factor XIa, to a series of solutions containing test sample and optionally one of the compounds of the present invention. If production of pNA is observed in the solutions containing test sample, but not in the presence of a compound of the present invention, then one would conclude Factor XIa was present.

Extremely potent and selective compounds of the present invention, those having $K_i$ values less than or equal to 0.001 µM against the target protease and greater than or equal to 0.1 µM against the other proteases, may also be used in diagnostic assays involving the quantitation of thrombin, Factor VIIa, IXa, Xa, XIa, and/or plasma kallikrein in serum samples. For example, the amount of Factor XIa in serum samples could be determined by careful titration of protease activity in the presence of the relevant chromogenic substrate, S2366, with a potent and selective Factor XIa inhibitor of the present invention.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising: a compound of the present invention or a pharmaceutically acceptable salt form thereof; and, (c) a package insert stating that the pharmaceutical composition can be used for the treatment of a thromboembolic and/or inflammatory disorder (as defined previously). In another embodiment, the package insert states that the pharmaceutical composition can be used in combination (as defined previously) with a second therapeutic agent to treat a thromboembolic and/or inflammatory disorder. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Dosage and Formulation

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the thromboembolic disorder.

By way of general guidance, the daily oral dosage of each active ingredient, when used for the indicated effects, will range between about 0.001 to 1000 mg/kg of body weight, preferably between about 0.01 to 100 mg/kg of body weight per day, and most preferably between about 1.0 to 20 mg/kg/day. Intravenously, the most preferred doses will range from about 1 to about 10 mg/kg/minute during a constant rate infusion. Compounds of this invention may be administered in a single daily dose, or the total daily dosage may be administered in divided doses of two, three, or four times daily.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5–95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl-or propyl-paraben, and chlorobutanol.

Suitable pharmaceutical carriers are described in *Remington's Pharmaceutical Sciences*, Mack Publishing Company, a standard reference text in this field.

Where the compounds of this invention are combined with other anticoagulant agents, for example, a daily dosage may be about 0.1 to 100 milligrams of the compound of the present invention and about 1 to 7.5 milligrams of the second anticoagulant, per kilogram of patient body weight. For a tablet dosage form, the compounds of this invention generally may be present in an amount of about 5 to 10 milligrams per dosage unit, and the second anti-coagulant in an amount of about 1 to 5 milligrams per dosage unit.

Where the compounds of the present invention are administered in combination with an anti-platelet agent, by way of general guidance, typically a daily dosage may be about 0.01 to 25 milligrams of the compound of the present invention and about 50 to 150 milligrams of the anti-platelet agent, preferably about 0.1 to 1 milligrams of the compound of the present invention and about 1 to 3 milligrams of antiplatelet agents, per kilogram of patient body weight.

Where the compounds of the present invention are administered in combination with thrombolytic agent, typically a daily dosage may be about 0.1 to 1 milligrams of the compound of the present invention, per kilogram of patient body weight and, in the case of the thrombolytic agents, the usual dosage of the thrombolyic agent when administered alone may be reduced by about 70–80% when administered with a compound of the present invention.

Where two or more of the foregoing second therapeutic agents are administered with the compound of the present invention, generally the amount of each component in a typical daily dosage and typical dosage form may be reduced relative to the usual dosage of the agent when administered alone, in view of the additive or synergistic effect of the therapeutic agents when administered in combination.

Particularly when provided as a single dosage unit, the potential exists for a chemical interaction between the combined active ingredients. For this reason, when the compound of Formula I and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

What is claimed is:
1. A compound of Formula (I):

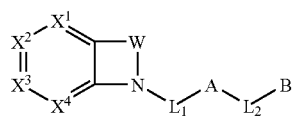

(I)

or a stereoisomer or pharmaceutically acceptable salts, hydrates, or prodrugs thereof, wherein:

W is —$CH_2CH_2$—, —$CH_2CR^4R^5$—, —$CR^4R^5CH_2$—, —$CHR^4CHR^5$—, —CH=CH—, or $CR^4$=$CR^5$—;

$L_1$ is —$CH_2$—, $L_2$ is a bond,

A is phenyl substituted with 0–3 $R^{11}$ and 0–1 $R^{12}$, or pyridyl substituted 0–3 $R^{11}$ and 0–1 $R^{12}$;

B is phenyl substituted with 0–3 $R^{11}$ and 0–1 $R^{12}$, or pyridyl substituted with 0–3 $R^{11}$ and 0–1 $R^{12}$;

$X^1$, $X^3$ and $X^4$ independently represent $CR^2$;

$X^2$ is $CR^1$;

$R^1$ is —C(=NH)$NH_2$, —C(O)$NH_2$, or —$CH_2NH_2$;

$R^2$ is H, F, Cl, Br, I, $OCF_3$, $CF_3$, $OR^a$, $SR^a$, CN, $NO_2$, —$NR^7R^8$, —C(O)$NR^{7a}R^8$, —$NR^{10}C(O)R^b$, —$S(O)_pNR^8R^9$, —$S(O)R^c$, —$S(O)_2R^c$, $C_{1-6}$alkyl substituted with 0–2 $R^{2a}$, $C_{2-6}$ alkenyl substituted with 0–2 $R^{2a}$, $C_{2-6}$ alkynyl substituted with 0–2 $R^{2a}$, —$(CH_2)_r$—$C_{3-10}$ carbocycle substituted with 0–3 $R^{2b}$, or —$(CH_2)_r$-5–10 membered heterocycle consisting of: carbon atoms and 1–4 heteroatoms selected from the group consisting of N, O, and $S(O)_p$, and substituted with 0–3 $R^{2b}$;

each $R^{2a}$ is, independently at each occurrence, H, F, $OCF_3$, $CF_3$, $OR^a$, $SR^a$, CN, —$NR^7R^8$, —C(O)$NR^{7a}R^8$, —$NR^{10}C(O)R^b$, —$S(O)_pNR^8R^9$, —$S(O)R^c$, or —$S(O)_2R^c$;

each $R^{2b}$ is, independently at each occurrence, H, F, Cl, Br, I, $OR^a$, $SR^a$, CN, $NO_2$, $CF_3$, —$SO_2R^c$, —$NR^7R^8$, $C_{1-6}$ alkyl, $C_{2-6}$ alkenyl, $C_{2-6}$ alkynyl, $C_{3-6}$ cycloalkyl, $C_{1-6}$ haloalkyl, $C_{1-4}$ haloalkyloxy-, $C_{1-4}$ alkyloxy-, $C_{1-4}$ alkylthio-, $C_{1-4}$ alkyl-C(O)—, or $C_{1-4}$ alkyl-C(O)NH—;

$R^4$ is H, F, $OR^a$, $SR^a$, —$NR^7R^8$, —$NR^{10}C(O)NR^{7a}R^8$, —$NR^{10}SO_2R^c$, —C(O)$OR^a$, —$(CH_2)_r$—C(O)$NR^{7a}R^8$, $C_{1-4}$ haloalkyl, $C_{1-6}$ alkyl substituted with 0–3 $R^{4a}$, $C_{2-6}$ alkenyl substituted with 0–3 $R^{4a}$, $C_{2-6}$ alkynyl substituted with 0–3 $R^{4a}$, —$(CH_2)_r$—$C_{3-10}$ carbocycle substituted with 0–3 $R^{4b}$, or —$(CH_2)_r$-5–10 membered heterocycle consisting of: carbon atoms and 1–4 heteroatoms selected from the group consisting of N, O, and $S(O)_p$, and substituted with 0–3 $R^{4b}$;

each $R^{4a}$ is, independently at each occurrence, H, $C_{1-4}$ alkyl, $OR^a$, F, =O, $CF_3$, CN, —C(O)$R^a$, —C(O)$OR^a$, —C(O)$NR^{7a}R^8$, —$NR^{10}COR^c$, or —$S(O)_pR^b$;

each $R^{4b}$ is, independently at each occurrence, H, OH, Cl, F, Br, I, CN, $NO_2$, $CF_3$, —C(O)$OR^a$, —$SO_2R^c$, —$NR^7R^8$, $C_{1-6}$ alkyl, $C_{2-6}$ alkenyl, $C_{2-6}$ alkynyl, $C_{3-6}$ cycloalkyl, $C_{1-4}$ haloalkyl, $C_{1-4}$ haloalkyloxy-, $C_{1-4}$ alkyloxy-, $C_{1-4}$ alkylthio-, $C_{1-4}$ alkyl-C(O)—, $C_{1-4}$ alkyl-C(O)NH—, —C(O)$NR^{7a}R^8$, —$NR^{10}C(O)R^c$, —$NR^{10}S(O)_2NR^8R^9$, or —$S(O)_2NR^8R^9$;

$R^5$ is H, F, $C_{1-4}$ haloalkyl, $C_{1-6}$ alkyl substituted with 0–3 $R^{5a}$, $C_{2-6}$ alkenyl substituted with 0–3 $R^{5a}$, $C_{2-6}$ alkynyl substituted with 0–3 $R^{5a}$, —$(CH_2)_r$—$C_{3-10}$carbocycle substituted with 0–3 $R^{5b}$, or —$(CH_2)_r$-$C_{5-10}$ membered heterocycle consisting of: carbon atoms and 1–4 heteroatoms selected from the group consisting of N, O, and $S(O)_p$, and substituted with 0–3 $R^{5b}$;

each $R^{5a}$ is, independently at each occurrence, H, $C_{1-4}$ alkyl, $OR^a$, F, =O, $CF_3$, CN, —C(O)$R^a$, —C(O)$OR^a$, —C(O)$NR^{7a}R^8$, or —$S(O)_pR^c$;

each $R^{5b}$ is, independently at each occurrence, H, OH, Cl, F, Br, I, CN, $NO_2$, $CF_3$, —C(O)$OR^a$, —$SO_2R^c$, —$NR^7R^8$, $C_{1-6}$ alkyl, $C_{2-6}$ alkenyl, $C_{2-6}$ alkynyl, $C_{3-6}$ cycloalkyl, $C_{1-4}$ haloalkyl, $C_{1-4}$ haloalkyloxy-, $C_{1-4}$ alkyloxy-, $C_{1-4}$ alkylthio-, $C_{1-4}$ alkyl-C(O)—, or $C_{1-4}$ alkyl-C(O)NH—;

each $R^7$ is, independently at each occurrence, H, $C_{1-6}$ alkyl, —$(CH_2)_n$-phenyl, ($C_{1-6}$ alkyl)C(O)—, ($C_{6-10}$ aryl)—C$_{0-4}$ alkyl-C(O)—, (C$_{3-6}$ cycloalkyl)—C$_{0-4}$ alkyl-C(O)—, (5–10 membered heteroaryl)—C$_{0-4}$ alkyl-C(O)—, (C$_{1-4}$ alkyl)OC(O)—, (C$_{6-10}$ aryl)—C$_{1-4}$ alkyl-OC(O)—, (C$_{1-4}$ alkyl)—C(O)O—(C$_{1-4}$ alkyl)—OC(O)—, (C$_{6-10}$ aryl)—C(O)O—(C$_{1-4}$ alkyl)—OC(O)—, (5–10 membered heteroaryl)—CH$_2$—OC(O)—, (C$_{1-6}$ alkyl)—NHC(O)—, (C$_{6-10}$ aryl)—C$_{0-4}$ alkyl-NHC(O)—, (5–10 membered heteroaryl)—C$_{0-4}$ alkyl-NHC(O)—, (C$_{1-6}$ alkyl)—S(O)$_2$—, (C$_{6-10}$ aryl)-(C$_{0-4}$ alkyl)—S(O)$_2$—, (5–10 membered heteroaryl)—C$_{0-4}$ alkyl-S(O)$_2$—, (C$_{1-6}$ alkyl)$_2$NC(O)—, phenyl-NHC(O)—, or (phenyl)(C$_{1-6}$ alkyl)NHC(O)—, wherein said phenyl, aryl and heteroaryl are substituted with 0–2 R$^f$;

each R$^{7a}$ is, independently at each occurrence, H, C$_{1-4}$ alkyl substituted with 0–2 R$^{7b}$ and/or 0–2 R$^{7c}$, —(CH$_2$)$_r$—C$_{3-10}$ carbocycle substituted with 0–3 R$^f$, or a —(CH$_2$)$_r$-5–12 membered heterocycle consisting of: carbon atoms and 1–4 heteroatoms selected from the group consisting of N, O, and S(O)$_p$, and substituted 0–3 R$^f$;

each R$^{7b}$ is, independently at each occurrence, =O, OR$^g$, F, CN, NO$_2$, —NR$^7$R$^8$, —C(O)R$^g$, —C(O)OR$^g$, —NR$^8$C(O)R$^g$, —C(O)NR$^8$R$^9$, —NR$^8$C(O)NR$^8$R$^9$, —SO$_2$NR$^8$R$^9$, —NR$^8$SO$_2$NR$^8$R$^9$, —NR$^8$SO$_2$—C$_{1-4}$ alkyl, —NR$^8$SO$_2$CF$_3$, —NR$^8$SO$_2$-phenyl, —S(O)$_2$CF$_3$, —S(O)$_p$—C$_{1-4}$ alkyl, —S(O)$_p$-phenyl, or —(CF$_2$)$_r$CF$_3$;

each R$^{7c}$ is, independently at each occurrence, C$_{3-10}$ carbocycle substituted with 0–3 R$^f$; or a 5–12 membered heterocycle consisting of: carbon atoms and 1–4 heteroatoms selected from the group consisting of N, O, and S(O)$_p$, and substituted 0–3 R$^f$;

each R$^8$ is, independently at each occurrence, H, C$_{1-6}$ alkyl, or —(CH$_2$)$_n$-phenyl;

each R$^{8a}$ is, independently at each occurrence, H, OH, C$_{1-6}$ alkyl, C$_{1-4}$ alkoxy, (C$_{6-10}$ aryl)—C$_{1-4}$ alkoxy, —(CH$_2$)$_n$-phenyl, (C$_{1-6}$ alkyl)C(O)—, (C$_{6-10}$ aryl)—C$_{0-4}$ alkyl-C(O)—, (C$_{3-6}$ cycloalkyl)—C$_{0-4}$ alkyl-C(O)—, (5–10 membered heteroaryl)—C$_{0-4}$ alkyl-C(O)—, (C$_{1-4}$ alkyl)OC(O)—, (C$_{6-10}$ aryl)—C$_{1-4}$ alkyl-OC(O)—, (C$_{1-4}$ alkyl)—C(O)O—(C$_{1-4}$ alkyl)—OC(O)—, (C$_{6-10}$ aryl)—C(O)O—(C$_{1-4}$ alkyl)—OC(O)—, (5–10 membered heteroaryl)—C$_{0-4}$ alkyl-OC(O)—, C$_{1-4}$ alkoxy, (C$_{1-4}$ alkyl)C(O)O—, or (C$_{6-10}$ aryl)—C$_{0-4}$ alkyl)—C(O)O—; wherein said phenyl, aryl and heteroaryl are substituted with 0–2 R$^f$;

alternatively, R$^7$ and R$^8$, or R$^{7a}$ and R$^8$, when attached to the same nitrogen, combine to form a 5–10 membered heterocyclic ring consisting of carbon atoms and 0–2 additional heteroatoms selected from the group consisting of N, O, and S(O)$_p$, and optionally substituted with 0–2 R$^d$;

each R$^9$ is, independently at each occurrence, H, C$_{1-6}$ alkyl, or —(CH$_2$)$_n$-phenyl;

each R$^{10}$ is, independently at each occurrence, H, C$_{1-6}$ alkyl substituted with 0–2 R$^{10a}$, C$_{2-6}$ alkenyl substituted with 0–2 R$^{10a}$, C$_{2-6}$ alkynyl substituted with 0–2 R$^{10a}$, —(CH$_2$)$_r$—C$_{3-10}$ carbocycle substituted with 0–3 R$^d$, or —(CH$_2$)$_r$-5–10 membered heterocycle consisting of carbon atoms and 1–4 heteroatoms selected from the group consisting of N, O, and S(O)$_p$, and substituted with 0–3 R$^d$;

each R$^{10a}$ is, independently at each occurrence, H, C$_{1-4}$ alkyl, OR$^a$, F, =O, CF$_3$, CN, NO$_2$, —C(O)R$^a$, —C(O)OR$^a$, —C(O)NR$^{7a}$R$^8$, or —S(O)$_p$R$^c$;

each R$^{11}$ is, independently at each occurrence, H, =O, —(CH$_2$)$_r$OR$^a$, F, Cl, Br, I, CF$_3$, CN, NO$_2$, —(CH$_2$)$_r$NR$^7$R$^8$, —(CH$_2$)$_r$—C(=NR$^8$)NR$^7$R$^9$, —C(O)R$^a$, —C(O)OR$^a$, —(CH$_2$)$_r$—NR$^8$C(O)R$^a$, —NR$^8$C(O)OR$^c$, —NR$^8$CO(CH$_2$)$_r$CO$_2$R$^a$, —C(O)NR$^{7a}$R$^8$, —NR$^8$C(O)NR$^8$R$^{10}$, —SO$_2$NR$^8$R$^{10}$, —NR$^8$SO$_2$NR$^8$R$^{10}$, —NR$^8$SO$_2$—C$_{1-4}$ alkyl, —NR$^8$SO$_2$CF$_3$, —NR$^8$SO$_2$-phenyl, —S(O)$_2$CF$_3$, —S(O)$_p$—C$_{1-4}$ alkyl, —S(O)$_p$-phenyl, —(CF$_2$)$_r$CF$_3$, C$_{1-6}$ alkyl substituted with 0–2 R$^{11a}$, C$_{2-6}$ alkenyl substituted with 0–2 R$^{11a}$, C$_{2-6}$ alkynyl substituted with 0–2 R$^{11a}$, C$_{1-6}$ alkyl substituted with 0–2 R$^{11b}$, C$_{2-6}$ alkenyl substituted with 0–2 R$^{11b}$, C$_{2-6}$ alkynyl substituted with 0–2 R$^{11b}$, phenyl substituted with 0–3 R$^c$ and/or 0–3 R$^d$, or a 5–7 membered heterocycle consisting of carbon atoms and 1–4 heteroatoms selected from the group consisting of N, O, and S(O)$_p$, and substituted with 0–3 R$^c$ and/or 0–3 R$^d$;

each R$^{11a}$ is, independently at each occurrence, =O, OR$^a$, F, Cl, Br, I, CN, NO$_2$, —NR$^7$R$^8$, —C(O)R$^a$, —C(O)OR$^a$, —NR$^8$C(O)R$^a$, —C(O)NR$^{7a}$R$^8$, —NR$^8$C(O)NR$^8$R$^{10}$, —SO$_2$NR$^8$R$^{10}$, —NR$^8$SO$_2$NR$^8$R$^{10}$, —NR$_8$SO$_2$—C$_{1-4}$ alkyl, —NR$^8$SO$_2$CF$_3$, —NR$^8$SO$_2$-phenyl, —S(O)$_2$CF$_3$, —S(O)$_p$—C$_{1-4}$ alkyl, —S(O)$_p$-phenyl, or —(CF$_2$)$_r$CF$_3$;

each R$^{11b}$ is, independently at each occurrence, C$_{3-10}$ carbocycle substituted with 0–3 R$^d$, or a 5–12 membered heterocycle consisting of: carbon atoms and 1–4 heteroatoms selected from the group consisting of N, O, and S(O)$_p$, and substituted 0–3 R$^d$;

each R$^{12}$ is, independently at each occurrence, OR$^{12a}$, —CH$_2$OR$^{12a}$, —C(O)NR$^{7a}$R$^8$, —(CH$_2$)$_r$CO$_2$R$^{12a}$, —(CH$_2$)$_r$SO$_3$H, —OSO$_3$H, —(CH$_2$)$_r$PO$_3$H, —OPO$_3$H$_2$, —PO$_3$H$_2$, —NHCOCF$_3$, —NHSO$_2$CF$_3$, —CONHNHSO$_2$CF$_3$, —C(CF$_3$)$_2$OH, —SO$_2$NHR$^{12a}$, —CONHSO$_2$NHR$^{12a}$, —SO$_2$NHCOR$^{12a}$, —SO$_2$NHCO$_2$R$^{12a}$, —CONHSO$_2$R$^{12b}$, —NHSO$_2$R$^{12b}$, —CONHOR$^{12b}$,

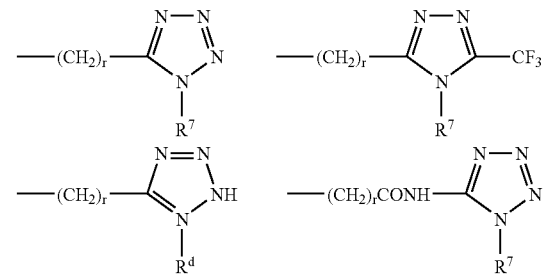

or

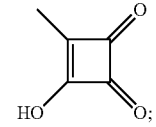

each R$^{12a}$ is, independently at each occurrence, H, C$_{1-6}$ alkyl, —(CH$_2$)$_r$—C$_{3-10}$ carbocycle substituted with 0–3 R$^d$, or —(CH$_2$)$_r$-5–10 membered heterocycle consisting of carbon atoms and 1–4 heteroatoms selected from the group consisting of N, O, and S(O)$_p$, and substituted with 0–3 R$^d$;

each R$^{12b}$ is, independently at each occurrence, C$_{1-6}$ alkyl substituted with 0–2 R$^{12c}$, C$_{2-6}$ alkenyl substituted with 0–2 R$^{12c}$, C$_{2-6}$ alkynyl substituted with R$^{12c}$, —(CH$_2$)$_r$—C$_{3-10}$ carbocycle substituted with 0–3 R$^{12c}$, or —(CH$_2$)$_r$-5–10 membered heterocycle consisting of:

carbon atoms and 1–4 heteroatoms selected from the group consisting of N, O, and $S(O)_p$, and substituted with 0–3 $R^{12c}$;

each $R^{12c}$ is, independently at each occurrence, H, F, Cl, Br, I, $CF_3$, $OCF_3$, CN, $NO_2$, $OR^a$, $—CO_2R^a$, $—NR^7R^8$, $—SO_2R^c$, $C_{1-6}$ alkyl, $C_{2-6}$ alkenyl, $C_{2-6}$ alkynyl, $—(CH_2)_r—C_{3-10}$ carbocycle substituted with 0–3 $R^d$, or $—(CH_2)_r$-5–10 membered heterocycle consisting of carbon atoms and 1–4 heteroatoms selected from the group consisting of N, O, and $S(O)_p$, and substituted with 0–3 $R^d$;

each $R^a$ is, independently at each occurrence, H, $C_{1-4}$ alkyl, $—(CH_2)_r—C_{3-7}$ cycloalkyl, $—(CH_2)_r—C_{6-10}$ aryl, or $—(CH_2)_r$-5–10 membered heteroaryl, wherein said aryl or heteroaryl groups are optionally substituted with 0–2 $R^f$;

each $R^b$ is, independently at each occurrence, $CF_3$, OH, $C_{1-4}$ alkoxy, $C_{1-6}$ alkyl, $—(CH_2)_r—C_{3-10}$ carbocycle substituted with 0–2 $R^d$, or $—(CH_2)_r$-5–10 membered heterocycle containing from 1–4 heteroatoms selected from the group consisting of N, O, and $S(O)_p$ and substituted with 0–2 $R^d$;

each $R^c$ is, independently at each occurrence, $C_{1-4}$ alkyl, $C_{6-10}$ aryl, 5–10 membered heteroaryl, $(C_{6-10}$ aryl)—$C_{1-4}$ alkyl, or (5–10 membered heteroaryl)—$C_{1-4}$ alkyl, wherein said aryl and heteroaryl groups are substituted with 0–2 $R^d$;

each $R^d$ is, independently at each occurrence, H, =O, $OR^a$, F, Cl, Br, I, CN, $NO_2$, $—NR^7R^8$, $—C(O)R^a$, $—C(O)OR^a$, $—NR^8C(O)R^a$, $—C(O)NR^{7a}R^8$, $—SO_2NR^8R^9$, $—NR^8SO_2NR^8R^9$, $—NR^8SO_2—C_{1-4}$ alkyl, $—NR^8SO_2CF_3$, $—NR^8SO_2$-phenyl, $—S(O)_2CF_3$, $—S(O)_p—C_{1-4}$ alkyl, $—S(O)_p$-phenyl, $—(CF_2)_rCF_3$, $C_{1-6}$ alkyl substituted with 0–2 $R^e$, $C_{2-6}$ alkenyl substituted with 0–2 $R^e$, or $C_{2-6}$ alkynyl substituted with 0–2 $R^e$;

each $R^e$ is, independently at each occurrence, =O, $OR^a$, F, Cl, Br, I, CN, $NO_2$, $—NR^8R^9$, $—C(O)R^a$, $—C(O)OR^a$, $—NR^8C(O)R^a$, $—C(O)NR^{7a}R^8$, $—SO_2NR^8R^9$, $—NR^8SO_2NR^8R^9$, $—NR^8SO_2—C_{1-4}$ alkyl, $—NR^8SO_2CF_3$, $—NR^8SO_2$-phenyl, $—S(O)_2CF_3$, $—S(O)_p—C_{1-4}$ alkyl, $—S(O)_p$-phenyl, or $—(CF_2)_rCF_3$;

each $R^f$ is, independently at each occurrence, H, =O, $—(CH_2)_r—OR^g$, F, Cl, Br, I, CN, $NO_2$, $—NR^8R^9$, $—C(O)R^g$, $—C(O)OR^g$, $—NR^8C(O)R^g$, $—C(O)NR^8R^9$, $—SO_2NR^8R^9$, $—NR^8SO_2NR^8R^9$, $—NR^8SO_2—C_{1-4}$ alkyl, $—NR^8SO_2CF_3$, $—NR^8SO_2$-phenyl, $—S(O)_2CF_3$, $—S(O)_p—C_{1-4}$ alkyl, $—S(O)_p$-phenyl, $—(CF_2)_rCF_3$, $C_{1-6}$ alkyl, $C_{2-6}$ alkenyl, or $C_{2-6}$ alkynyl;

each $R^g$ is, independently at each occurrence, H, $C_{1-6}$ alkyl, or $—(CH_2)_n$-phenyl;

n, at each occurrence, is selected from 0, 1, 2, 3, and 4;
p, at each occurrence, is selected from 0, 1, and 2; and
r, at each occurrence, is selected from 0, 1, 2, 3, and 4.

2. A compound according to claim 1, wherein the compound is of Formula (Ia):

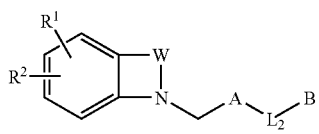

(Ia)

or a stereoisomer or pharmaceutically acceptable salts, hydrates, or prodrugs thereof, wherein:

W is $—CH_2CH_2—$, $—CH_2CR^4R^5—$, $—CR^4R^5CH_2—$, or $—CR^4=CH—$, $L_2$ is a bond, A is phenyl substituted with 0–2 $R^{11}$ and 0–1 $R^{12}$, or pyridyl substituted 0–2 $R^{11}$ and 0–1 $R^{12}$;

B is phenyl substituted with 0–2 $R^{11}$ and 0–1 $R^{12}$, or pyridyl substituted with 0–2 $R^{11}$ and 0–1 $R^{12}$;

R is $—C(=NH)NH_2$, $—C(O)NH_2$, or $—CH_2NH_2$;

$R^2$ is H, F, $OR^a$, CN, $—NR^7R^8$, $—C(O)NR^{7a}R^8$, $—NR^{10}C(O)R^b$, $—S(O)_pNR^8R^9$, $—S(O)R^c$, $—S(O)_2R^c$, $C_{1-6}$ alkyl substituted with 0–2 $R^{2a}$, $—(CH_2)_r—C_{3-7}$ carbocycle substituted with 0–2 $R^{2b}$, or $—(CH_2)_r$-5–7 membered heterocycle consisting of: carbon atoms and 1–4 heteroatoms selected from the group consisting of N, O, and $S(O)_p$, and substituted with 0–2 $R^{2b}$;

each $R^{2a}$ is, independently at each occurrence, H, F, $OCF_3$, $CF_3$, $OR^a$, $SR^a$, CN, $—NR^7R^8$, $—C(O)NR^{7a}R^8$, $—S(O)_pNR^8R^9$, $—NR^{10}C(O)R^b$, $—S(O)_pNR^8R^9$, $—S(O)R^c$, or $—S(O)_2R^c$;

each $R^{2b}$ is, independently at each occurrence, H, F, $OR^a$, $SR^a$, CN, $NO_2$, $CF_3$, $—SO_2R^c$, $—NR^7R^8$, $C_{1-6}$ alkyl, $C_{2-6}$ alkenyl, $C_{2-6}$ alkynyl, $C_{3-6}$ cycloalkyl, $C_{1-4}$ haloalkyl, $C_{1-4}$ haloalkyloxy-, $C_{1-4}$ alkyloxy-, $C_{1-4}$ alkylthio-, $C_{1-4}$ alkyl-C(O)—, or $C_{1-4}$ alkyl-C(O)NH—;

$R^4$ is H, F, $C_{1-4}$ haloalkyl, $—(CH_2)_r—C(O)NR^{7a}R^8$, substituted with 0–3 $R^{4a}$, $C_{2-6}$ alkenyl substituted with 0–3 $R^{4a}$, $C_{2-6}$ alkynyl substituted with 0–3 $R^{4a}$—$(CH_2)_r$—$C_{3-8}$ carbocycle substituted with 0–3 $R^{4b}$, or $—(CH_2)_r$-5–6 membered heterocycle consisting of: carbon atoms and 1–4 heteroatoms selected from the group consisting of N, O, and $S(O)_p$, and substituted with 0–3 $R^{4b}$;

each $R^{4a}$ is, independently at each occurrence, H, $C_{1-4}$ alkyl, $OR^a$, F, =O, $CF_3$, CN, $—C(O)R^a$, $—C(O)OR^a$, $—C(O)NR^{7a}R^8$, $—NR^{10}COR^c$, or $—S(O)_pR^b$;

each $R^{4b}$ is, independently at each occurrence, H, OH, Cl, F, Cl, Br, CN, $NO_2$, $CF_3$, $—C(O)OR^a$, $—SO_2R^c$, $—NR^7R^8$, $C_{1-6}$ alkyl, $C_{2-6}$ alkenyl, $C_{2-6}$ alkynyl, $C_{3-6}$ cycloalkyl, $C_{1-4}$ haloalkyl, $C_{1-4}$ haloalkyloxy-, $C_{1-4}$ alkyloxy-, $C_{1-4}$ alkylthio-, $C_{1-4}$ alkyl-C(O)—, $C_{1-4}$ alkyl-C(O)NH—, $—C(O)NR^{7a}R^8$, $—NR^{10}C(O)R^c$, $—NR^{10}S(O)_2NR^8R^9$, or $—S(O)_2NR^8R^9$;

each $R^5$ is, independently at each occurrence, H, F, $C_{1-4}$ haloalkyl, $C_{1-6}$ alkyl substituted with 0–2 $R^{5a}$, $C_{2-6}$ alkenyl substituted with 0–2 $R^{5a}$, $C_{2-6}$ alkynyl substituted with 0–2 $R^{5a}$, $—(CH_2)_r—C_{3-7}$ cycloalkyl substituted with 0–2 $R^{5b}$, $—(CH_2)_r$-phenyl substituted with 0–2 $R^{5b}$, or $—(CH_2)_r$-5–6 membered heterocycle consisting of: carbon atoms and 1–4 heteroatoms selected from the group consisting of N, O, and $S(O)_p$, and substituted with 0–2 $R^{5b}$;

each $R^{5a}$ is, independently at each occurrence, H, $C_{1-4}$ alkyl, $OR^a$, F, =O, $CF_3$, CN, $—C(O)R^a$, $—C(O)OR^a$, $—C(O)NR^{7a}R^8$, or $—S(O)_pR^c$;

each $R^{5b}$ is, independently at each occurrence, H, OH, Cl, F, Br, CN, $NO_2$, $CF_3$, $—C(O)OR^a$, $—SO_2R^c$, $—NR^7R^8$, $C_{1-6}$ alkyl, $C_{2-6}$ alkenyl, $C_{2-6}$ alkynyl, $C_{3-6}$ cycloalkyl, $C_{1-4}$ haloalkyl, $C_{1-4}$ haloalkyloxy-, $C_{1-4}$ alkyloxy-, $C_{1-4}$ alkylthio-, $C_{1-4}$ alkyl-C(O)—, or $C_{1-4}$ alkyl-C(O)NH—;

each $R^7$ is, independently at each occurrence, H, $C_{1-6}$ alkyl, $—(CH_2)_n$-phenyl, $(C_{1-6}$ alkyl)C(O)—, $(C_{6-10}$ aryl)—$C_{0-4}$ alkyl-C(O)—, $(C_{3-6}$ cycloalkyl)—$C_{0-4}$ alkyl-C(O)—, (5–10 membered heteroaryl)—$C_{0-4}$ alkyl-C(O)—, (C$_{1-4}$ alkyl)OC(O)—, (C$_{6-10}$ aryl)—C$_{1-4}$ alkyl-OC(O)—, (C$_{1-4}$ alkyl)—C(O)O—(C$_{1-4}$ alkyl)—OC(O)—, (C$_{6-10}$ aryl)—C(O)O—(C$_{1-4}$ alkyl)—OC(O)—, (5–10 membered heteroaryl)—CH$_2$—OC(O)—, (C$_{1-6}$ alkyl)—NHC(O)—, (C$_{6-10}$ aryl)—C$_{0-4}$ alkyl-NHC(O)—, (5–10 membered heteroaryl)—C$_{0-4}$ alkyl-NHC(O)—, (C$_{1-6}$ alkyl)—S(O)$_2$—, (C$_{6-10}$ aryl)—(C$_{0-4}$ alkyl)—S(O)$_2$—, (5–10 membered heteroaryl)—C$_{0-4}$ alkyl-S(O)$_2$—, (C$_{1-6}$ alkyl)$_2$NC(O)—, phenyl-NHC(O)—, benzyl-NHC(O)—, or (phenyl)(C$_{1-6}$ alkyl)NC(O)—, wherein said phenyl, aryl and heteroaryl are substituted with 0–2 R$^f$;

each R$^{7a}$ is, independently at each occurrence, H, C$_{1-4}$ alkyl substituted with 0–1 R$^{7b}$ or 0–1 R$^c$, C$_{3-7}$ cycloalkyl substituted with 0–2 R$^d$, phenyl substituted with 0–3 R$^f$, or a 5–6 membered heterocycle consisting of: carbon atoms and 1–4 heteroatoms selected from the group consisting of N, O, and S(O)$_p$, and substituted 0–3 R$^f$;

each R$^{7b}$ is, independently at each occurrence, =O, OR$^g$, F, Cl, Br, I, CN, NO$_2$, —NR$^7$R$^8$, —C(O)R$^g$, —C(O)OR$^g$, —NR$^8$C(O)R$^g$, —C(O)NR$^8$R$^9$, —NR$^8$C(O)NR$^8$R$^9$, —SO$_2$NR$^8$R$^9$, —NR$^8$SO$_2$NR$^8$R$^9$, —NR$^8$SO$_2$—C$_{1-4}$ alkyl, —NR$^8$SO$_2$CF$_3$, —NR$^8$SO$_2$-phenyl, —S(O)$_2$CF$_3$, —S(O)$_p$—C$_{1-4}$ alkyl, —S(O)$_p$-phenyl, or —(CF$_2$)$_r$CF$_3$;

each R$^{7c}$ is, independently at each occurrence, C$_{3-10}$ carbocycle substituted with 0–3 R$^f$; or a 5–12 membered heterocycle consisting of: carbon atoms and 1–4 heteroatoms selected from the group consisting of N, O, and S(O)$_p$, and substituted 0–3 R$^f$;

each R$^8$ is, independently at each occurrence, H, C$_{1-6}$ alkyl, or —(CH$_2$)$_n$-phenyl;

each R$^{8a}$ is, independently at each occurrence, H, OH, C$_{1-6}$ alkyl, —(CH$_2$)$_n$-phenyl, (C$_{1-6}$ alkyl)C(O)—, (C$_{6-10}$ aryl)—C$_{1-4}$ alkyl-C(O)—, (C$_{3-6}$ cycloalkyl)—C$_{0-4}$ alkyl-C(O)—, (5–10 membered heteroaryl)—C$_{0-4}$ alkyl-C(O)—, (C$_{1-4}$ alkyl)OC(O)—, (C$_{6-10}$ aryl)—C$_{0-4}$ alkyl-OC(O)—, (C$_{1-4}$ alkyl)—C(O)O—(C$_{1-4}$ alkyl)—OC(O)—, C$_{1-4}$ alkoxy, (C$_{6-10}$ aryl)—C$_{1-4}$ alkoxy, (C$_{1-4}$ alkyl)C(O)O—, or (C$_{6-10}$ aryl)—(C$_{0-4}$ alkyl)—C(O)O—; wherein said phenyl, aryl and heteroaryl are substituted with 0–2 R$^f$;

alternatively, R$^7$ and R$^8$, or R$^{7a}$ and R$^8$, when attached to the same nitrogen, combine to form a 5–10 membered heterocyclic ring consisting of carbon atoms and 0–2 additional heteroatoms selected from the group consisting of N, O, and S(O)$_p$;

each R$^9$ is, independently at each occurrence, H, C$_{1-6}$ alkyl, or —(CH$_2$)$_n$-phenyl;

each R$^{10}$ is, independently at each occurrence, H, C$_{1-6}$ alkyl substituted with 0–2 R$^{10a}$, C$_{2-6}$ alkenyl substituted with 0–2 R$^{10a}$, C$_{2-6}$ alkynyl substituted with 0–2 R$^{10a}$, (C$_{1-6}$ alkyl)C(O)—, (C$_{3-6}$ cycloalkyl)C$_{1-3}$ alkyl-C(O)—, (C$_{3-6}$ cycloalkyl)C(O)—, phenyl-C(O)—, benzyl-C(O)—, benzyl-S(O)$_2$—, (C$_{1-6}$ alkyl)NHC(O)—, (C$_{1-6}$ alkyl)$_2$NC(O)—, phenyl-NHC(O)—, benzyl-NHC(O)—, (phenyl)(C$_{1-6}$ alkyl)NC(O)—, (benzyl)(C$_{1-6}$ alkyl)NC(O)—, (C$_{1-6}$ alkyl)—S(O)$_2$—, phenyl-S(O)$_2$—, —(CH$_2$)$_r$—C$_{3-10}$ carbocycle substituted with 0–3 R$^d$, or —(CH$_2$)$_r$-5–10 membered heterocycle consisting of carbon atoms and 1–4 heteroatoms selected from the group consisting of N, O, and S(O)$_p$, and substituted with 0–3 R$^d$;

each R$^{10a}$ is, independently at each occurrence, H, C$_{1-4}$ alkyl, OR$^a$, Cl, F, Cl, Br, I, =O, CF$_3$, CN, NO$_2$, —C(O)R$^a$, —C(O)OR$^a$, —C(O)NR$^{7a}$R$^8$, or —S(O)$_p$R$^c$;

each R$^{11}$ is, independently at each occurrence, H, =O, —(CH$_2$)$_r$—OR$^a$, F, Cl, Br, I, CF$_3$, CN, NO$_2$, —(CH$_2$)$_r$—NR$^7$R$^8$, —(CH$_2$)$_r$—C(=NR$^8$)NR$^7$R$^9$, —C(O)R$^a$, —C(O)OR$^a$, —(CH$_2$)$_r$—NR$^8$C(O)R$^a$, —NHC(O)(CH$_2$)$_r$C(O)OR$^a$, —NR$^8$C(O)OR$^c$, —C(O)NR$^{7a}$R$^8$, —NR$^8$C(O)NR$^8$R$^{10}$, —SO$_2$NR$^8$R$^{10}$, —NR$^8$SO$_2$NR$^8$R$^{10}$, —NR$^8$SO$_2$—C$_{1-4}$ alkyl, —NR$^8$SO$_2$CF$_3$, —NR$^8$SO$_2$-phenyl, —S(O)$_2$CF$_3$, —S(O)$_p$—C$_{1-4}$ alkyl, —S(O)$_p$-phenyl, —(CF$_2$)$_r$CF$_3$, C$_{1-6}$ alkyl substituted with 0–2 R$^{11a}$, C$_{2-6}$ alkenyl substituted with 0–2 R$^{11a}$, C$_{2-6}$ alkynyl substituted with 0–2 R$^{11a}$, C$_{1-6}$ alkyl substituted with 0–2 R$^{11b}$, C$_{2-6}$ alkenyl substituted with 0–2 R$^{11b}$, or C$_{2-6}$ alkynyl substituted with 0–2 R$^{11b}$;

each R$^{11a}$ is, independently at each occurrence, =O, OR$^a$, F, Cl, Br, I, CN, NO$_2$, —NR$^7$R$^8$, —C(O)R$^a$, —C(O)OR$^a$, —NR$^8$C(O)R$^a$, —C(O)NR$^{7a}$R$^8$, —NR$^8$C(O)NR$^8$R$^{10}$, —SO$_2$NR$^8$R$^{10}$, —NR$^8$SO$_2$NR$^8$R$^{10}$, —NR$^8$SO$_2$—C$_{1-4}$ alkyl, —NR$^8$SO$_2$CF$_3$, —NR$^8$SO$_2$-phenyl, —S(O)$_2$CF$_3$, —S(O)$_p$—C$_{1-4}$ alkyl, —S(O)$_p$-phenyl, or —(CF$_2$)$_r$CF$_3$;

each R$^{11b}$ is, independently at each occurrence, C$_{3-10}$ carbocycle substituted with 0–3 R$^d$, or a 5–12 membered heterocycle consisting of: carbon atoms and 1–4 heteroatoms selected from the group consisting of N, O, and S(O)$_p$, and substituted 0–3 R$^d$;

each R$^{12}$ is, independently at each occurrence, OR$^{12a}$, —CH$_2$OR$^{12a}$, —C(O)NR$^{7a}$R$^8$, —(CH$_2$)$_r$CO$_2$R$^{12a}$, —(CH$_2$)$_r$SO$_3$H, —OSO$_3$H, —(CH$_2$)$_r$PO$_3$H, —OPO$_3$H$_2$, —PO$_3$H$_2$, —NHCOCF$_3$, —NHSO$_2$CF$_3$, —CONHNHSO$_2$CF$_3$, —C(CF$_3$)$_2$OH, —SO$_2$NHR$^{12a}$, —CONHSO$_2$NHR$^{12a}$, —SO$_2$NHCOR$^{12a}$, —SO$_2$NHCO$_2$R$^{12a}$, —CONHSO$_2$R$^{12b}$, —NHSO$_2$R$^{12b}$, —CONHOR$^{12b}$,

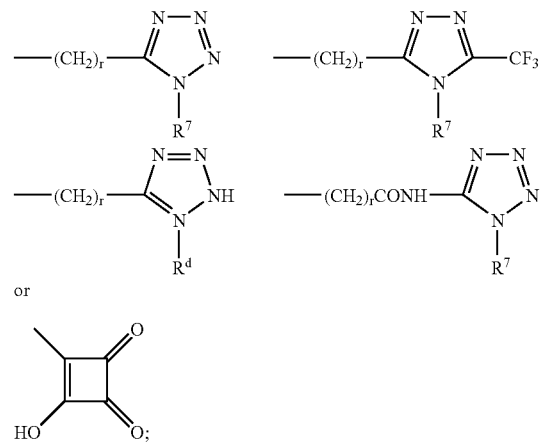

or each R$^{12a}$ is, independently at each occurrence, H, C$_{1-6}$ alkyl, —(CH$_2$)$_r$—C$_{3-10}$ carbocycle substituted with 0–3 R$^d$, or —(CH$_2$)$_r$-5–10 membered heterocycle consisting of carbon atoms and 1–4 heteroatoms selected from the group consisting of N, O, and S(O)$_p$, and substituted with 0–3 R$^d$;

each R$^{12b}$ is, independently at each occurrence, C$_{1-6}$ alkyl substituted with 0–2 R$^{12c}$, C$_{2-6}$ alkenyl substituted with 0–2 R$^{12c}$, C$_{2-6}$ alkynyl substituted with 0–2 R$^{12c}$, —(CH$_2$)$_r$—C$_{3-10}$ carbocycle substituted with 0–3 R$^{12c}$, or —(CH$_2$)$_r$-5–10 membered heterocycle consisting of: carbon atoms and 1–4 heteroatoms selected from the group consisting of N, O, and S(O)$_p$, and substituted with 0–3 R$^{12c}$;

each R$^{12c}$ is, independently at each occurrence, H, F, Cl, Br, I, CF$_3$, OCF$_3$, CN, NO$_2$, OR$^a$, —CO$_2$R$^a$, —NR$^7$R$^8$, —SO$_2$R$^c$, C$_{1-6}$ alkyl, C$_{2-6}$ alkenyl, C$_{2-6}$ alkynyl, —(CH$_2$)$_r$—C$_{3-10}$ carbocycle substituted with 0–3 R$^d$, or —(CH$_2$)$_r$-5–10 membered heterocycle consisting of carbon atoms and 1–4 heteroatoms selected from the group consisting of N, O, and S(O)$_p$, and substituted with 0–3 R$^d$;

each R$^a$ is, independently at each occurrence, H, C$_{1-4}$ alkyl, —(CH$_2$)$_r$—C$_{3-7}$ cycloalkyl, —(CH$_2$)$_r$—C$_{6-10}$ aryl, or —(CH$_2$)$_r$-5–10 membered heteroaryl, wherein said aryl or heteroaryl groups are optionally substituted with 0–2 R$^f$;

each R$^b$ is, independently at each occurrence, CF$_3$, OH, C$_{1-4}$ alkoxy, C$_{1-6}$ alkyl, —(CH$_2$)$_r$—C$_{3-10}$ carbocycle substituted with 0–2 R$^d$, or —(CH$_2$)$_r$-5–10 membered heterocycle containing from 1–4 heteroatoms selected from the group consisting of N, O, and S(O)$_p$ and substituted with 0–2 R$^d$;

each R$^c$ is, independently at each occurrence, C$_{1-4}$ alkyl, C$_{6-10}$ aryl, 5–10 membered heteroaryl, (C$_{6-10}$ aryl)-C$_{1-4}$ alkyl, or (5–10 membered heteroaryl)-C$_{1-4}$ alkyl, wherein said aryl and heteroaryl groups are substituted with 0–2 R$^d$;

each R$^d$ is, independently at each occurrence, H, =O, OR$^a$, F, Cl, Br, I, CN, NO$_2$, —NR$^7$R$^8$, —C(O)R$^a$, —C(O)OR$^a$, —NR$^8$C(O)R$^a$, —C(O)NR$^{7a}$R$^8$, —SO$_2$NR$^8$R$^9$, —NR$^8$SO$_2$NR$^8$R$^9$, —NR$^8$SO$_2$—C$_{1-4}$ alkyl, —NR$^8$SO$_2$CF$_3$, —NR$^8$SO$_2$-phenyl, —S(O)$_2$CF$_3$, —S(O)$_p$—C$_{1-4}$ alkyl, —S(O)$_p$-phenyl, —(CF$_2$)$_r$CF$_3$, C$_{1-6}$ alkyl substituted with 0–2 R$^e$, C$_{2-6}$ alkenyl substituted with 0–2 R$^e$, or C$_{2-6}$ alkynyl substituted with 0–2 R$^e$;

each R$^e$ is, independently at each occurrence, =O, OR$^a$, F, Cl, Br, I, CN, NO$_2$, —NR$^8$R$^9$, —C(O)R$^a$, —C(O)OR$^a$, —NR$^8$C(O)R$^a$, —C(O)NR$^{7a}$R$^8$, —SO$_2$NR$^8$R$^9$, —NR$^8$SO$_2$NR$^8$R$^9$, —NR$^8$SO$_2$—C$_{1-4}$ alkyl, —NR$^8$SO$_2$CF$_3$, —NR$^8$SO$_2$-phenyl, —S(O)$_2$CF$_3$, —S(O)$_p$—C$_{1-4}$ alkyl, —S(O)$_p$-phenyl, or —(CF$_2$)$_r$CF$_3$;

each R$^f$ is, independently at each occurrence, H, =O, —(CH$_2$)$_r$—OR$^g$, F, Cl, Br, I, CN, NO$_2$, —NR$^8$R$^9$, —C(O)R$^g$, —C(O)OR$^g$, —NR$^8$C(O)R$^g$, —C(O)NR$^8$R$^9$, —SO$_2$NR$^8$R$^9$, —NR$^8$SO$_2$NR$^8$R$^9$, —NR$^8$SO$_2$—C$_{1-4}$ alkyl, —NR$^8$SO$_2$CF$_3$, —NR$^8$SO$_2$-phenyl, —S(O)$_2$CF$_3$, —S(O)$_p$—C$_{1-4}$ alkyl, —S(O)$_p$-phenyl, —(CF$_2$)$_r$CF$_3$, C$_{1-6}$ alkyl, C$_{2-6}$ alkenyl, or C$_{2-6}$ alkynyl;

each R$^g$ is, independently at each occurrence, H, C$_{1-6}$ alkyl, or —(CH$_2$)$_n$-phenyl;

n, at each occurrence, is selected from 0, 1, 2, 3, and 4;

p, at each occurrence, is selected from 0, 1, and 2; and r, at each occurrence, is selected from 0, 1, 2, 3, and 4.

3. A compound according to claim 2, wherein the compound is of Formula (Ib):

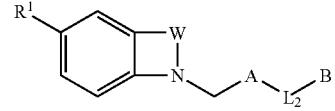

(Ib)

or a stereoisomer or pharmaceutically acceptable salts, hydrates, or prodrugs thereof, wherein:

W is —CH$_2$CH$_2$—, —CH=CH—, —C(benzyl)=CH—, —C(C$_{1-4}$ alkyl)=CH—, —CH(benzyl)CH$_2$—, —C(3,5-diMe-benzyl)=CH—, —C(CH$_2$OH)=CH, —C(CONHMe)=CH—, —C(CONHPh)=CH—, —C(4-CO$_2$H-benzyl)=CH—, or —C(CH$_2$CONHMe)=CH—;

L$_2$ is a bond,

A is phenyl substituted with 0–2 R$^{11}$, or pyridyl substituted with 0–2 R$^{11}$;

B is phenyl substituted with 0–2 R$^{11}$ and 0–1 R$^{12}$, or pyridyl substituted with 0–2 R$^{11}$ and 0–1 R$^{12}$;

R$^1$ is —C(=NH)NH$_2$, —C(=O)NH$_2$, or —CH$_2$NH$_2$, each R$^7$ is, independently at each occurrence, H, C$_{1-6}$ alkyl, or benzyl;

each R$^{7a}$ is, independently at each occurrence, H, C$_{1-4}$ alkyl substituted with 0–1 R$^{7b}$ or 0–1 R$^c$, C$_{3-7}$ cycloalkyl substituted with 0–2 R$^d$, phenyl substituted with 0–3 R$^f$, or a 5–6 membered heterocycle consisting of: carbon atoms and 1–4 heteroatoms selected from the group consisting of N, O, and S(O)$_p$, and substituted 0–3 R$^f$;

each R$^{7b}$ is, independently at each occurrence, =O, OR$^g$, F, Cl, Br, I, CN, NO$_2$, —NR$^7$R$^8$, —C(O)R$^g$, —C(O)OR$^g$, —NR$^8$C(O)R$^g$, —C(O)NR$^8$R$^9$, —NR$^8$C(O)NR$^8$R$^9$, —SO$_2$NR$^8$R$^9$, —NR$^8$SO$_2$NR$^8$R$^9$, —NR$^8$SO$_2$—C$_{1-4}$ alkyl, —NR$^8$SO$_2$CF$_3$, NR$^8$SO$_2$-phenyl, —S(O)$_2$CF$_3$, —S(O)$_p$—C$_{1-4}$ alkyl, —S(O)$_p$-phenyl, or —(CF$_2$)$_r$CF$_3$;

each R$^{7c}$ is, independently at each occurrence, C$_{3-10}$ carbocycle substituted with 0–3 R$^f$; or a 5–12 membered heterocycle consisting of: carbon atoms and 1–4 heteroatoms selected from the group consisting of N, O, and S(O)$_p$, and substituted 0–3 R$^f$;

each R$^8$ is, independently at each occurrence, H, C$_{1-6}$ alkyl, or benzyl;

each R$^9$ is, independently at each occurrence, H, C$_{1-6}$ alkyl, or benzyl;

each R$^{11}$ is, independently at each occurrence, H, F, Cl, CF$_3$, C$_{1-6}$ alkyl, —(CH$_2$)$_r$—OR$^a$, CN, —(CH$_2$)$_r$—NR$^7$R$^8$, —(CH$_2$)$_r$—C(=NR$^8$)NR$^7$R$^9$, —C(O)R$^a$, —C(O)OR$^a$, —(CH$_2$)$_r$—NR$^8$C(O)R$^a$, —NR$^8$C(O)OR$^c$, —C(O)NR$^{7a}$R$^8$, —NR$^8$C(O)NR$^8$R$^{10}$, —SO$_2$NR$^8$R$^{10}$, —NR$^8$SO$_2$NR$^8$R$^{10}$, or —NR$^8$SO$_2$—C$_{1-4}$ alkyl;

R$^{12}$ is —C(O)NR$^{7a}$R$^8$, —(CH$_2$)$_r$CO$_2$R$^{12a}$, —CH$_2$OR$^{12a}$, —SO$_2$NHR$^{12a}$, —SO$_2$NHCOR$^{12a}$, —SO$_2$NHCO$_2$R$^{12a}$, —CONHSO$_2$R$^{12b}$, —NHSO$_2$R$^{12b}$, or —(CH$_2$)$_r$-5-tetrazolyl;

each R$^{12a}$ is, independently at each occurrence, H or C$_{1-6}$ alkyl;

each R$^{12b}$ is, independently at each occurrence, C$_{1-4}$ alkyl substituted with 0–1 R$^{12c}$, C$_{2-4}$ alkenyl substituted with 0–1 R$^{12c}$, C$_{2-4}$ alkynyl substituted with R$^{12c}$, —(CH$_2$)$_r$—C$_{3-7}$ carbocycle substituted with 0–2 R$^{12c}$, or —(CH$_2$)$_r$-5–6 membered heterocycle consisting of:

carbon atoms and 1–4 heteroatoms selected from the group consisting of N, O, and S(O)$_p$, and substituted with 0–2 R$^{12c}$;

each R$^{12c}$ is, independently at each occurrence, H, F, Cl, Br, I, CF$_3$, OCF$_3$, CN, NO$_2$, OR$^a$, —CO$_2$R$^a$, —NR$^7$R$^8$, —SO$_2$R$^c$, C$_{1-6}$ alkyl, C$_{2-6}$ alkenyl, C$_{2-6}$ alkynyl, —(CH$_2$)$_r$—C$_{3-10}$ carbocycle substituted with 0–3 R$^d$; or —(CH$_2$)$_r$-5–10 membered heterocycle consisting of carbon atoms and 1–4 heteroatoms selected from the group consisting of N, O, and S(O)$_p$, and substituted with 0–3 R$^d$;

each R$^a$ is, independently at each occurrence, H, C$_{1-4}$ alkyl, —(CH$_2$)$_r$—C$_{3-7}$ cycloalkyl, —(CH$_2$)$_r$—C$_{6-10}$ aryl, or —(CH$_2$)$_r$-5–10 membered heteroaryl, wherein said aryl or heteroaryl groups are optionally substituted with 0–2 R$^f$;

each R$^c$ is, independently at each occurrence, C$_{1-4}$ alkyl, phenyl or benzyl;

each R$^f$ is, independently at each occurrence, H, =O, —(CH$_2$)$_r$—OR$^g$, F, Cl, Br, CF$_3$, CN, NO$_2$, —NR$^8$R$^9$, —C(O)R$^g$, —C(O)OR$^g$, —NR$^8$C(O)R$^g$, —C(O)NR$^8$R$^9$, —SO$_2$NR$^8$R$^9$, —NR$^8$SO$_2$—C$_{1-4}$ alkyl, —NR$^8$SO$_2$CF$_3$, —S(O)$_2$CF$_3$, —S(O)$_p$—C$_{1-4}$ alkyl, C$_1$–C$_6$ alkyl, C$_2$–C$_6$ alkenyl, or C$_2$–C$_6$ alkynyl;

each R$^g$ is, independently at each occurrence, H or C$_{1-4}$ alkyl;

p, at each occurrence, is selected from 0, 1, and 2; and r, at each occurrence, is selected from 0, 1, 2, 3, and 4.

4. A compound according to claim 3, wherein:

W is —CH$_2$CH$_2$—, —CH=CH—, —C(benzyl)=CH—, —C(C$_{1-4}$ alkyl)=CH—, —CH(benzyl)CH$_2$—, —C(3, 5-diMe-benzyl)=CH—, —C(CH$_2$OH)=CH, —C(CONHMe)=CH—, —C(CONHPh)=CH—, —C(4-CO$_2$H-benzyl)=CH—, or —C(CH$_2$CONHMe)=CH—;

L$_2$ is a bond,

A is phenyl substituted with 0–2 R$^{11}$, or pyridyl substituted with 0–2 R$^{11}$;

B is phenyl substituted with 0–2 R$^{11}$ and 0–1 R$^{12}$, or pyridyl substituted with 0–2 R$^{11}$ and 0–1 R$^{12}$;

R$^1$ is —C(=NH)NH$_2$, —C(=O)NH$_2$, or —CH$_2$NH$_2$;

each R$^{11}$ is, independently at each occurrence, H, F, CF$_3$, C$_{1-4}$ alkyl, OH, —CH$_2$OH, OMe, OEt, CN, —NH$_2$, —CH$_2$NH$_2$, —CH$_2$NMe$_2$, —C(=NH)NH$_2$, —CH$_2$C(=NH)NH$_2$, —CH$_2$NHAc, —CO$_2$H, —CO$_2$Me, —NHAc, —NHCOEt, —NHCOPr, —NHCO(i-Pr), —NHC(O)(i-Bu), —NHCO(phenyl), —NHCO(benzyl), —NHCO(tetrazol-5-yl), —NHCOCH$_2$(tetrazol-5-yl), —NHCO(CH$_2$)$_2$(tetrazol-5-yl), —CO(1-morpholino), —CO[4-(2-OH-ethyl)-1-piperdinyl], —CO[4-(2-OMe-ethyl)-1-piperdinyl], —CO[4-(2-CO$_2$Et-ethyl)-1-piperdinyl], —C(O)NH$_2$, —C(O)NHMe, —C(O)NHEt, —C(O)NHPr, —C(O)NH(i-Bu), —C(O)NHisoamyl, —C(O)NH(CH$_2$CH$_2$N(Me)$_2$), —CONHCH$_2$CO$_2$H, —CONH(CH$_2$)$_2$CO$_2$H, —CONH(CH$_2$)$_3$CO$_2$H, —CONH(CH$_2$)$_3$OH, —CONHcyclopropylmethyl, —CONHcyclohexylmethyl, —CONHphenyl, —CONH(benzyl), —CONHCH(Me)phenyl, —CONH(4-OMe-benzyl), —CONH(3,5-diOMe-benzyl), —CONH(4-Cl-benzyl), —CONH(phenethyl), —CONH(3-Cl-phenethyl), —CONH(phenylpropyl), —CONH[(2-pyridyl)-methyl], —CONH[(3-pyridyl)-methyl], —CONH[2-(2-pyridyl)-ethyl], —CONHCH$_2$(4-tetrahydropyranyl), —CONHCH$_2$(1-indanyl), —CONH(1-naphthyl), —NHSO$_2$Me, or —NHSO$_2$Et; and R$^{12}$ is OH, —CH$_2$OH, —CO$_2$H, —CH$_2$(CO$_2$H), —CO$_2$Me, —SO$_2$NH$_2$, or —CONH$_2$.

5. A compound according to claim 4, wherein:

W is —CH$_2$CH$_2$—, —CH=CH—, —C(benzyl)=CH—, —CH(benzyl)CH$_2$—, or —C(C$_{1-4}$ alkyl)=CH—;

L$_2$ is a bond;

A is 1,2-phenylene, 3-carboxy-1,2-phenylene, 4-methyl-1,2-phenylene, 4-methoxy-1,2-phenylene, 4-aminomethyl-1,2-phenylene, 4-amidino-1,2-phenylene, 4-amidinomethyl-1,2-phenylene, 4-acetoamidomethyl-1,2-phenylene, 5-(N,N-dimethylaminoethylcarbamoyl)-1,2-phenylene, 5-carboxy-1,2-phenylene, 5-hydroxymethyl-1,2-phenylene, 5-acetylamino-1,2-phenylene, 5-propionylamino-1,2-phenylene, 5-butyrylamino-1,2-phenylene, 5-(3-methylbutyrylamino)-1,2-phenylene, 5-(2,2-dimethylpropionylamino)-1,2-phenylene, 5-benzylcarbonylamino-1,2-phenylene, 4-methoxy-5-hydroxy-1,2-phenylene, 5-carbamoyl-1,2-phenylene, 5-methylcarbamoyl-1,2-phenylene, 5-ethylcarbamoyl-1,2-phenylene, 5-propylcarbamoyl-1,2-phenylene, 5-isopropylcarbamoyl-1,2-phenylene, 5-isobutylcarbamoyl-1,2-phenylene, 5-t-butylcarbamoyl-1,2-phenylene, 5-isoamylcarbamoyl-1,2-phenylene, 5-carboxymethylcarbamoyl-1,2-phenylene, 5-(2-carboxyethyl)carbamoyl-1,2-phenylene, 5-(3-hydroxypropyl)carbamoyl-1,2-phenylene, 5-(3-carboxypropyl)carbamoyl-1,2-phenylene, 5-cyclopropylmethylcarbamoyl-1,2-phenylene, 5-cyclohexylmethylcarbamoyl-1,2-phenylene, 5-phenylcarbamoyl-1,2-phenylene, 5-benzylcarbamoyl-1,2-phenylene, 5-(1-phenylethyl)carbamoyl-1,2-phenylene, 5-phenethylcarbamoyl-1,2-phenylene, 5-(3-phenylpropylcarbamoyl)-1,2-phenylene, 5-(4-methoxybenzyl)carbamoyl-1,2-phenylene, 5-(3,5-dimethoxybenzyl)carbamoyl-1,2-phenylene, 5-(4-chlorobenzyl)carbamoyl-1,2-phenylene, 5-[2-(3-chloropheny)ethyl]carbamoyl-1,2-phenylene, 5-(2-pyridylmethyl)carbamoyl-1,2-phenylene, 5-(3-pyridylmethyl)carbamoyl-1,2-phenylene, 5-[2-(2-pyridyl)ethyl]carbamoyl-1,2-phenylene, 5-(4-tetrahydropyranyl)methylcarbamoyl-1,2-phenylene, 5-(morpholine-4-carbonyl)-1,2-phenylene, 5-[4-(2-hydroxyethyl)-piperdine-1-carbonyl]-1,2-phenylene, 5-[4-(2-methoxyethyl)-piperdine-1-carbonyl]-1,2-phenylene, 5-[4-(ethoxycarbonylmethyl)-piperdine-1-carbonyl]-1,2-phenylene, 5-(1-naphthyl)carbamoyl-1,2-phenylene, 5-(1-indanyl)carbamoyl-1,2-phenylene, 1,3-phenylene, 5-amino-1,3-phenylene, 5-acetylamino-1,3-phenylene, 5-propionylamino-1,3-phenylene, 5-butyrylamino-1,3-phenylene, 5-(3-methylbutyrylamino)-1,2-phenylene, 5-(2,2-dimethylpropionylamino)-1,2-phenylene, or 6-amino-2,3-pyridylene; wherein the attachment to L$_2$ is at carbon 1 of said phenylene rings;

B is 2-carboxy-phenyl, 2-aminosulfonyl-phenyl, 3-carboxymethyl-phenyl, 2,4-dicarboxy-phenyl, 2,4-dimethoxycarbonyl-phenyl, 2,4-dicarbamoyl-phenyl, 2-carboxy-4-methoxycarbonyl-phenyl, 2-carboxy-4-methyl-phenyl, 2-carboxy-4-methoxy-phenyl, 2-carboxy-4-ethoxy-phenyl, 2-carboxy-4-fluoro-phenyl, 2-carboxy-4-amino-phenyl, 2-carboxy-4-cyano-phenyl, 2-carboxy-4-acetylamino-phenyl, 2-carboxy-4-carbamoyl-phenyl, 2,5-dicarboxy-phenyl, 2,5-dicarboxy-4-methoxy-phenyl, 2-carboxy-4,5-dimethoxy-phenyl, 2-carboxy-4-trifluoromethyl-phenyl, 5-carboxy-4-methoxy-phenyl, 3-carboxy-4-pyridyl, or 2-carboxy-6-methoxy-3-pyridyl; and R¹ is —C(=NH)NH₂, —C(=O)NH₂, or —CH₂NH₂.

6. A compound of claim 1 selected from:

2'-(5-carbamimidoyl-2,3-dihydroindol-1-ylmethyl)-biphenyl-2-carboxylic acid;
2'-(5-carbamimidoyl-2,3-dihydroindol-1-ylmethyl)-biphenyl-2,4-dicarboxylic acid;
2'-(5-carbamimidoyl-2,3-dihydroindol-1-ylmethyl)-4-isobutylcarbamoyl-biphenyl-2-carboxylic acid;
2'-(5-carbamimidoyl-2,3-dihydroindol-1-ylmethyl)-4-methoxybiphenyl-2-carboxylic acid;
4-acetylamino-2'-(5-carbamimidoyl-2,3-dihydroindol-1-ylmethyl)-biphenyl-2-carboxylic acid;
2'-(5-carbamimidoyl-2,3-dihydroindol-1-ylmethyl)-4'-methoxy-biphenyl-2-carboxylic acid;
2'-(5-carbamimidoyl-2,3-dihydro-indol-1-ylmethyl)-4-carbamoyl-biphenyl-2-carboxylic acid;
3'-(5-carbamimidoyl-2,3-dihydro-indol-1-ylmethyl)-biphenyl-2-carboxylic acid;
3'-(5-carbamimidoyl-2,3-dihydro-indol-1-ylmethyl)-biphenyl-2,4-dicarboxylic acid;
1-(2'-sulfamoyl-biphenyl-3-ylmethyl)-2,3-dihydro-1H-indole-5-carboxamidine;
[2'-(5-carbamimidoyl-2,3-dihydro-indol-1-ylmethyl)-biphenyl-3-yl]-acetic acid;
5'-acetylamino-2'-(5-carbamimidoyl-2,3-dihydro-indol-1-ylmethyl)-biphenyl-2-carboxylic acid;
2'-(5-carbamimidoyl-2,3-dihydro-indol-1-ylmethyl)-5'-phenethylcarbamoyl-biphenyl-2-carboxylic acid;
5'-benzylcarbamoyl-2'-(5-carbamimidoyl-2,3-dihydro-indol-1-ylmethyl)-biphenyl-2-carboxylic acid;
2'-(5-carbamimidoyl-2,3-dihydro-indol-1-ylmethyl)-5'-(3-phenylpropylcarbamoyl)-biphenyl-2-carboxylic acid;
2'-(5-carbamimidoyl-2,3-dihydro-indol-1-ylmethyl)-5'-(2-pyridin-2-yl-ethylcarbamoyl)-biphenyl-2-carboxylic acid;
2'-(5-carbamimidoyl-2,3-dihydro-indol-1-ylmethyl)-4-methoxy-5'-phenethylcarbamoyl-biphenyl-2-carboxylic acid;
2'-(5-carbamimidoyl-2,3-dihydro-indol-1-ylmethyl)-4-methoxy-5'-(3-chloro-phenethyl)carbamoyl-biphenyl-2-carboxylic acid;
2'-(5-carbamimidoyl-indol-1-ylmethyl)-biphenyl-2-carboxylic acid;
2'-(3-benzyl-5-carbamimidoyl-indol-1-ylmethyl)-4-methoxy-biphenyl-2-carboxylic acid;
2'-(3-benzyl-5-carbamimidoyl-indol-1-ylmethyl)-4-methoxy-5'-phenethylcarbamoyl-biphenyl-2-carboxylic acid;
2'-(3-benzyl-5-carbamimidoyl-2,3-dihydro-indol-1-ylmethyl)-4-methoxy-biphenyl-2-carboxylic acid;
2'-(3-benzyl-5-carbamimidoyl-2,3-dihydro-indol-1-ylmethyl)-4-methoxy-5'-phenethylcarbamoyl-biphenyl-2-carboxylic acid;
2'-(6-carbamimidoyl-3,4-dihydro-2H-quinolin-1-ylmethyl)-biphenyl-2-carboxylic acid;
2'-(5-carbamimidoyl-2,3-dihydro-indol-1-ylmethyl)-5'-phenethylcarbamoyl-biphenyl-2-carboxylic acid;
5'-benzylcarbamoyl-2'-(5-carbamimidoyl-2,3-dihydro-indol-1-ylmethyl)-biphenyl-2-carboxylic acid;
2'-(5-carbamimidoyl-2,3-dihydro-indol-1-ylmethyl)-4-methoxy-5'-phenethylcarbamoyl-biphenyl-2-carboxylic acid;
5'-benzylcarbamoyl-2'-(5-carbamimidoyl-2,3-dihydro-indol-1-ylmethyl)-4-methoxy-biphenyl-2-carboxylic acid;
2-benzyloxy-5-(5-carbamimidoyl-2,3-dihydro-indol-1-ylmethyl)-benzoic acid;
2-benzyloxy-3-(5-carbamimidoyl-2,3-dihydro-indol-1-ylmethyl)-benzoic acid;
2'-(5-carbamimidoyl-2,3-dihydro-indol-1-ylmethyl)-4-methoxy-4'-methyl-biphenyl-2-carboxylic acid;
2'-(5-carbamimidoyl-indol-1-ylmethyl)-4-methoxy-4'-methyl-biphenyl-2-carboxylic acid;
2'-(3-benzyl-5-carbamimidoyl-indol-1-ylmethyl)-4-methoxy-4'-methyl-biphenyl-2-carboxylic acid;
2'-(3-benzyl-5-carbamimidoyl-2,3-dihydro-indol-1-ylmethyl)-4-methoxy-4'-methyl-biphenyl-2-carboxylic acid;
2'-(5-carbamimidoyl-indol-1-ylmethyl)-4-methoxy-5'-(2-pyridin-2-yl-ethylcarbamoyl)-biphenyl -2-carboxylic acid;
2'-(5-carbamimidoyl-2,3-dihydro-indol-1-ylmethyl)-4-ethoxy-biphenyl-2-carboxylic acid;
2'-(5-carbamimidoyl-2,3-dihydro-indol-1-ylmethyl)-4-fluoro-biphenyl-2-carboxylic acid;
5'-benzylcarbamoyl-2'-(5-carbamimidoyl-indol-1-ylmethyl)-4-methoxy-biphenyl-2-carboxylic acid;
2'-(3-benzyl-5-carbamimidoyl-indol-1-ylmethyl)-4'-carbamimidoyl-4-methoxy-biphenyl-2-carboxylic acid;
2'-(5-carbamimidoyl-2,3-dihydro-indol-1-ylmethyl)-4-methoxy-5'-phenylacetylamino-biphenyl-2-carboxylic acid;
2'-(5-carbamimidoyl-indol-1-ylmethyl)-4-methoxy-biphenyl-2-carboxylic acid;
6'-(3-benzyl-5-carbamimidoyl-indol-1-ylmethyl)-4-methoxy-biphenyl-2,3'-dicarboxylic acid;
2'-(5-carbamimidoyl-2,3-dihydro-indol-1-ylmethyl)-4,5-dimethoxy-biphenyl-2-carboxylic acid;
2'-(5-carbamimidoyl-2,3-dihydro-indol-1-ylmethyl)-4-methyl-biphenyl-2-carboxylic acid;
2'-(5-carbamimidoyl-indol-1-ylmethyl)-5'-[2-(3-chloro-phenyl)-ethylcarbamoyl]-4-methoxy-biphenyl-2-carboxylic acid;
6'-(5-carbamimidoyl-2,3-dihydro-indol-1-ylmethyl)-4-methoxy-biphenyl-2,3'-dicarboxylic acid;
2'-(5-carbamimidoyl-indol-1-ylmethyl)-4-carbamoyl-biphenyl-2-carboxylic acid;
4'-aminomethyl-2'-(3-benzyl-5-carbamimidoyl-indol-1-ylmethyl)-4-methoxy-biphenyl-2-carboxylic acid;
4'-(acetylamino-methyl)-2'-(3-benzyl-5-carbamimidoyl-indol-1-ylmethyl)-4-methoxy-biphenyl-2-carboxylic acid;
2'-(3-benzyl-5-carbamimidoyl-2,3-dihydro-indol-1-ylmethyl)-4'-carbamimidoyl-4-methoxy-biphenyl-2-carboxylic acid;
2'-(5-carbamimidoyl-2,3-dihydro-indol-1-ylmethyl)-4-methoxy-5'-propylcarbamoyl-biphenyl-2-carboxylic acid;
2'-(5-carbamimidoylindol-1-ylmethyl)-4-methoxy-5'-propylcarbamoyl-biphenyl-2-carboxylic acid;
2'-[5-carbamimidoyl-3-(3,5-dimethyl-benzyl)-indol-1-ylmethyl]-4-methoxy-biphenyl-2-carboxylic acid;
4'-aminomethyl-2'-(3-benzyl-5-carbamimidoyl-2,3-dihydro-indol-1-ylmethyl)-4-methoxy-biphenyl-2-carboxylic acid;
2'-[5-carbamimidoyl-3-(3,5-dimethyl-benzyl)-2,3-dihydro-indol-1-ylmethyl]-4-methoxy-biphenyl-2-carboxylic acid;
2'-(5-carbamimidoylindol-1-ylmethyl)-5'-(carboxymethyl-carbamoyl)-4-methoxy-biphenyl-2-carboxylic acid;

2'-(5-carbamimidoyl-2,3-dihydro-indol-1-ylmethyl)-5'-(carboxymethyl-carbamoyl)-4-methoxy-biphenyl-2-carboxylic acid;

2'-(5-carbamimidoylindol-1-ylmethyl)-biphenyl-2,5-dicarboxylic acid;

2'-(5-carbamimidoyl-2,3-dihydro-indol-1-ylmethyl)-biphenyl-2,5-dicarboxylic acid;

5'-benzylcarbamoyl-2'-(5-carbamimidoyl-2,3-dihydro-indol-1-ylmethyl)-4-methyl-biphenyl-2-carboxylic acid;

2'-(5-carbamimidoyl-2,3-dihydro-indol-1-ylmethyl)-4-trifluoromethyl-biphenyl-2-carboxylic acid;

2'-(5-carbamimidoylindol-1-ylmethyl)-4-methoxy-biphenyl-2,5-dicarboxylic acid;

2'-(5-carbamimidoyl-2,3-dihydro-indol-1-ylmethyl)-4-methyl-5'-propylcarbamoyl-biphenyl-2-carboxylic acid;

2'-(5-carbamimidoyl-2,3-dihydro-indol-1-ylmethyl)-5'-(cyclohexylmethyl-carbamoyl)-4-methyl-biphenyl-2-carboxylic acid;

2-[6-amino-2-(5-carbamimidoyl-indol-1-ylmethyl)-pyridin-3-yl]-5-methoxy-benzoic acid;

2-[6-amino-2-(5-carbamimidoyl-2,3-dihydro-indol-1-ylmethyl)-pyridin-3-yl]-5-methoxy-benzoic acid;

2'-(3-benzyl-5-carbamimidoyl-indol-1-ylmethyl)-5'-carbamoyl-4-methoxy-biphenyl-2-carboxylic acid;

2'-(3-benzyl-5-carbamimidoyl-indol-1-ylmethyl)-4-methoxy-5'-methylcarbamoyl-biphenyl-2-carboxylic acid;

2'-(5-carbamimidoyl-2,3-dihydro-indol-1-ylmethyl)-4-methyl-5'-[(pyridin-2-ylmethyl)-carbamoyl]-biphenyl-2-carboxylic acid;

2'-(5-carbamimidoyl-2,3-dihydro-indol-1-ylmethyl)-5'-isobutylcarbonylamino-4-methoxy-biphenyl-2-carboxylic acid;

5'-benzylcarbamoyl 2'-(5-carbamimidoyl-indol-1-ylmethyl)-4-methyl-biphenyl-2-carboxylic acid;

2'-(5-carbamimidoyl-3-methylcarbamoyl-indol-1-ylmethyl)-4-methoxy-biphenyl-2-carboxylic acid;

2'-(5-carbamimidoyl-3-phenylcarbamoyl-indol-1-ylmethyl)-4-methoxy-biphenyl-2-carboxylic acid;

2'-(5-carbamimidoyl-2,3-dihydro-indol-1-ylmethyl)-5'-(3,5-dimethoxy-benzylcarbamoyl)-4-methoxy-biphenyl-2-carboxylic acid;

2'-(5-carbamimidoyl-2,3-dihydro-indol-1-ylmethyl)-4-methoxy-5'-[(naphthalen-1-ylmethyl)-carbamoyl]-biphenyl-2-carboxylic acid;

2'-(5-carbamimidoyl-2,3-dihydro-indol-1-ylmethyl)-5'-(2-carboxy-ethylcarbamoyl)-4-methoxy-biphenyl-2-carboxylic acid;

2'-(5-carbamimidoyl-2,3-dihydro-indol-1-ylmethyl)-4-methoxy-biphenyl-2,5-dicarboxylic acid;

2'-(5-carbamimidoyl-2,3-dihydro-indol-1-ylmethyl)-4-methoxy-5'-(4-methoxy-benzylcarbamoyl)-biphenyl-2-carboxylic acid;

2'-(5-carbamimidoyl-3-hydroxymethyl-indol-1-ylmethyl)-4-methoxy-biphenyl-2-carboxylic acid;

2'-(5-carbamimidoyl-2,3-dihydro-indol-1-ylmethyl)-5'-(cyclopropylmethyl-carbamoyl)-4-methoxy-biphenyl-2-carboxylic acid;

2'-(5-carbamimidoyl-2,3-dihydro-indol-1-ylmethyl)-5'-(4-chloro-benzylcarbamoyl)-4-methoxy-biphenyl-2-carboxylic acid;

2'-(3-benzyl-5-carbamimidoyl-indol-1-ylmethyl)-4-methyl-5'-methylcarbamoyl-biphenyl-2-carboxylic acid;

2'-(3-benzyl-5-carbamimidoyl-indol-1-ylmethyl)-4-carbamoyl-5'-methylcarbamoyl-biphenyl-2-carboxylic acid;

2'-(3-benzyl-5-carbamimidoyl-indol-1-ylmethyl)-4-methoxy-biphenyl-2,5-dicarboxylic acid;

2'-(3-benzyl-5-carbamimidoyl-indol-1-ylmethyl)-4-methoxy-5'-methylcarbamoyl-biphenyl-2,5-dicarboxylic acid;

2'-(5-carbamimidoyl-2,3-dihydro-indol-1-ylmethyl)-4-methoxy-5'-(morpholine-4-carbonyl)-biphenyl-2-carboxylic acid;

2'-(5-carbamimidoyl-2,3-dihydro-indol-1-ylmethyl)-4-methoxy-5'-[4-(2-methoxy-ethyl)-piperazine-1-carbonyl]-biphenyl-2-carboxylic acid;

2'-(5-carbamimidoyl-2,3-dihydro-indol-1-ylmethyl)-5'-isobutylcarbamoyl-4-methoxy-biphenyl-2-carboxylic acid;

2'-(5-carbamimidoyl-2,3-dihydro-indol-1-ylmethyl)-4-methoxy-5'-(3-methyl-butylcarbamoyl) -biphenyl-2-carboxylic acid;

2'-(5-carbamimidoyl-2,3-dihydro-indol-1-ylmethyl)-4-methoxy-5'-[(pyridin-3-ylmethyl)-carbamoyl]-biphenyl-2-carboxylic acid;

2'-(5-carbamimidoyl-2,3-dihydro-indol-1-ylmethyl)-4-methoxy-5'-[(tetrahydropyran-4-ylmethyl)-carbamoyl]-biphenyl-2-carboxylic acid;

2'-(5-carbamimidoyl-2,3-dihydro-indol-1-ylmethyl)-5'-[4-(ethoxycarbonylmethyl)]-piperazine-1-carbonyl-4-methoxy-biphenyl-2-carboxylic acid;

2'-(5-carbamimidoyl-indol-1-ylmethyl)-4-methoxy-biphenyl-2,6-dicarboxylic acid;

2'-(5-carbamimidoyl-2,3-dihydro-indol-1-ylmethyl)-4-methoxy-5'-((S)-1-phenyl-ethylcarbamoyl)-biphenyl-2-carboxylic acid;

2'-(5-carbamimidoyl-2,3-dihydro-indol-1-ylmethyl)-4-methoxy-5'-((R)-1-phenyl-ethylcarbamoyl)-biphenyl-2-carboxylic acid;

2'-(5-carbamimidoyl-2,3-dihydro-indol-1-ylmethyl)-5'-(indan-1-ylcarbamoyl)-4-methoxy-biphenyl-2-carboxylic acid;

2'-(3-benzyl-5-carbamimidoyl-indol-1-ylmethyl)-5'-ethylcarbamoyl-4-methoxy-biphenyl-2-carboxylic acid;

2'-(3-benzyl-5-carbamimidoyl-indol-1-ylmethyl)-4-methoxy-5'-propylcarbamoyl-biphenyl-2-carboxylic acid;

2'-(3-benzyl-5-carbamimidoyl-indol-1-ylmethyl)-5'-(cyclopropylmethyl-carbamoyl)-4-methoxy-biphenyl-2-carboxylic acid;

2'-(3-benzyl-5-carbamimidoyl-indol-1-ylmethyl)-5'-isobutylcarbamoyl-4-methoxy-biphenyl-2-carboxylic acid;

2'-(5-carbamimidoyl-2,3-dihydro-indol-1-ylmethyl)-5'-(3-hydroxypropylcarbamoyl)-4-methoxy-biphenyl-2-carboxylic acid;

2'-(5-carbamimidoyl-2,3-dihydro-indol-1-ylmethyl)-5'-methylcarbamoyl-4-methoxy-biphenyl-2-carboxylic acid;

2'-(5-carbamimidoyl-2,3-dihydro-indol-1-ylmethyl)-5'-(3-carboxypropylcarbamoyl)]-4-methoxy-biphenyl-2-carboxylic acid;

2'-(5-carbamimidoyl-2,3-dihydro-indol-1-ylmethyl)-5'-(4-(2-hydroxyethyl)-piperazine-1-carbonyl)-4-methoxy-biphenyl-2-carboxylic acid;

2'-(5-carbamimidoyl-2,3-dihydro-indol-1-ylmethyl)-5'-[2-(N,N-dimethylamino)ethyl]carbamoyl-4-methoxy-biphenyl-2-carboxylic acid;

2'-(3-benzyl-5-carbamimidoyl-indol-1-ylmethyl)-5'-methylcarbamoyl-4-methoxy-biphenyl-3-carboxylic acid;

2'-(3-(4-carboxybenzyl)-5-carbamimidoyl-indol-1-ylm-ethyl)-4-methoxy-5'-methylcarbamoyl-biphenyl-2-car-boxylic acid;

3-{2-(5-carbamimidoyl-2,3-dihydro-indol-1-ylmethyl)-5-[(pyridin-2-ylmethyl)-carbamoyl]-phenyl}-6-meth-oxy-pyridine-2-carboxylic acid;

2'-(5-carbamimidoyl-3-methylcarbamoylmethyl-indol-1-ylmethyl)-5'-methylcarbamoyl-4-methoxy-biphenyl-2-carboxylic acid;

2'-(5-carbamimidoyl-2,3-dihydro-indol-1-ylmethyl)-5'-[(pyridin-2-ylmethyl)-carbamoyl]-biphenyl-2-car-boxylic acid;

3'-(5-carbamimidoyl-2,3-dihydro-indol-1-ylmethyl)-4-carbamoyl-biphenyl-2-carboxylic acid;

4-{2-[5-carbamimidoylindol-1-ylmethyl)-5-[(pyridin-2-ylmethyl)-carbamoyl]-phenyl}-nicotinic acid;

2'-(5-carbamoyl-2,3-dihydro-indol-1-ylmethyl)-5'-(3-chlorophenethyl-carbamoyl)-4-methoxy-biphenyl-2-carboxylic acid;

5'-benzylcarbamoyl-2'-(5-carbamoyl-2,3-dihydro-indol-1-ylmethyl)-4-methoxy-biphenyl-2-carboxylic acid;

2'-(5-aminomethyl-3-benzyl-indol-1-ylmethyl)-4-me-thyl-5'-methylcarbamoyl-biphenyl-2-carboxylic acid; and 2'-(5-carbamimidoyl-3-benzyl-indol-1-ylmethyl)-5'-dim-ethylcarbamoyl-4-methoxy-biphenyl-2-carboxylic acid;

or a stereoisomer or a pharmaceutically acceptable salt, hydrate or prodrug form thereof.

7. A pharmaceutical composition, comprising: a pharmaceutically acceptable carrier and a therapeutically effective amount of a compound of claim 1 or a pharmaceutically acceptable salt or hydrate thereof.

8. A method for treating thromboembolic disorders, comprising: administering to a patient in need thereof a therapeutically effective amount of a compound of claim 1 or a pharmaceutically acceptable salt or hydrate thereof.

9. A method according to claim 8, wherein the thromboembolic disorder is selected from the group consisting of arterial cardiovascular thromboembolic disorders, venous cardiovascular thromboembolic disorders, and thromboembolic disorders in the chambers of the heart.

10. A method according to claim 9, wherein the thromboembolic disorder is selected from unstable angina, an acute coronary syndrome, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, or (f) other procedures in which blood is exposed to an artificial surface that promotes thrombosis.

11. A pharmaceutical composition, comprising: a pharmaceutically acceptable carrier and a therapeutically effective amount of a compound of claim 2 or a pharmaceutically acceptable salt or hydrate thereof.

12. A pharmaceutical composition, comprising: a pharmaceutically acceptable carrier and a therapeutically effective amount of a compound of claim 3 or a pharmaceutically acceptable salt or hydrate thereof.

13. A pharmaceutical composition, comprising: a pharmaceutically acceptable carrier and a therapeutically effective amount of a compound of claim 4 or a pharmaceutically acceptable salt or hydrate thereof.

14. A pharmaceutical composition, comprising: a pharmaceutically acceptable carrier and a therapeutically effective amount of a compound of claim 5 or a pharmaceutically acceptable salt or hydrate thereof.

15. A pharmaceutical composition, comprising: a pharmaceutically acceptable carrier and a therapeutically effective amount of a compound of claim 6 or a pharmaceutically acceptable salt or hydrate thereof.

16. A method for treating thromboembolic disorders, comprising: administering to a patient in need thereof a therapeutically effective amount of a compound of claim 2 or a pharmaceutically acceptable salt or hydrate thereof.

17. A method according to claim 16, wherein the thromboembolic disorder is selected from the group consisting of arterial cardiovascular thromboembolic disorders, venous cardiovascular thromboembolic disorders, and thromboembolic disorders in the chambers of the heart.

18. A method according to claim 17, wherein the thromboembolic disorder is selected from unstable angina, an acute coronary syndrome, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, or (f) other procedures in which blood is exposed to an artificial surface that promotes thrombosis.

19. A method for treating thromboembolic disorders, comprising: administering to a patient in need thereof a therapeutically effective amount of a compound of claim 3 or a pharmaceutically acceptable salt or hydrate thereof.

20. A method according to claim 19, wherein the thromboembolic disorder is selected from the group consisting of arterial cardiovascular thromboembolic disorders, venous cardiovascular thromboembolic disorders, and thromboembolic disorders in the chambers of the heart.

21. A method according to claim 20, wherein the thromboembolic disorder is selected from unstable angina, an acute coronary syndrome, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, or (f) other procedures in which blood is exposed to an artificial surface that promotes thrombosis.

22. A method for treating thromboembolic disorders, comprising: administering to a patient in need thereof a therapeutically effective amount of a compound of claim 4 or a pharmaceutically acceptable salt or hydrate thereof.

23. A method according to claim 22, wherein the thromboembolic disorder is selected from the group consisting of arterial cardiovascular thromboembolic disorders, venous cardiovascular thromboembolic disorders, and thromboembolic disorders in the chambers of the heart.

24. A method according to claim 23, wherein the thromboembolic disorder is selected from unstable angina, an acute coronary syndrome, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, or (f) other procedures in which blood is exposed to an artificial surface that promotes thrombosis.

25. A method for treating thromboembolic disorders, comprising: administering to a patient in need thereof a therapeutically effective amount of a compound of claim 5 or a pharmaceutically acceptable salt or hydrate thereof.

26. A method according to claim 25, wherein the thromboembolic disorder is selected from the group consisting of arterial cardiovascular thromboembolic disorders, venous cardiovascular thromboembolic disorders, and thromboembolic disorders in the chambers of the heart.

27. A method according to claim 26, wherein the thromboembolic disorder is selected from unstable angina, an acute coronary syndrome, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, or (f) other procedures in which blood is exposed to an artificial surface that promotes thrombosis.

28. A method for treating thromboembolic disorders, comprising: administering to a patient in need thereof a therapeutically effective amount of a compound of claim 6 or a pharmaceutically acceptable salt or hydrate thereof.

29. A method according to claim 28, wherein the thromboembolic disorder is selected from the group consisting of arterial cardiovascular thromboembolic disorders, venous cardiovascular thromboembolic disorders, and thromboembolic disorders in the chambers of the heart.

30. A method according to claim 29, wherein the thromboembolic disorder is selected from unstable angina, an acute coronary syndrome, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, or (f) other procedures in which blood is exposed to an artificial surface that promotes thrombosis.

* * * * *